United States Patent
Swaminathan et al.

(10) Patent No.: US 11,648,275 B2
(45) Date of Patent: May 16, 2023

(54) PROFILING AND TREATMENT OF MYC-ASSOCIATED CANCERS WITH NK CELLS AND TYPE 1 INTERFERON

(71) Applicant: The Board of Trustees of the Leland Stanford Junior University, Stanford, CA (US)

(72) Inventors: Srividya Swaminathan, Santa Clara, CA (US); Dean W. Felsher, San Mateo, CA (US); Holden Terry Maecker, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 395 days.

(21) Appl. No.: 16/771,617

(22) PCT Filed: Dec. 12, 2018

(86) PCT No.: PCT/US2018/065246
§ 371 (c)(1),
(2) Date: Jun. 10, 2020

(87) PCT Pub. No.: WO2019/125868
PCT Pub. Date: Jun. 27, 2019

(65) Prior Publication Data
US 2020/0353000 A1 Nov. 12, 2020

Related U.S. Application Data

(60) Provisional application No. 62/607,501, filed on Dec. 19, 2017.

(51) Int. Cl.
*A61K 35/17* (2015.01)
*A61K 38/21* (2006.01)
*G01N 33/574* (2006.01)

(52) U.S. Cl.
CPC ............ *A61K 35/17* (2013.01); *A61K 38/212* (2013.01); *G01N 33/57426* (2013.01)

(58) Field of Classification Search
CPC .......................... A61K 35/17; G01N 2800/52
See application file for complete search history.

(56) References Cited

U.S. PATENT DOCUMENTS

2013/0129675 A1   5/2013   Priebe et al.

OTHER PUBLICATIONS

Sanchez-Martin et al. The NOTCH1-MYC highway toward T-cell acute lymphoblastic leukemia. Blood, 129, 1124-1133, 2017. (Year: 2017).*
Schlee et al. (2007) "c-MYC activation impairs the NF-kB and the Interferon response: Implications for the pathogenesis of Burkitt's lymphoma" Int J. Cancer, vol. 120, p. 1387-1395.
Swami Nathan et at . . . (2017) "MYC functions as a master switch for natural kilter cell-mediated immune surveillance of lymphoid malignancies" Cancer Research, Abstract.
Hofer et al. (2017) "Natural Killer cell-Based cancer immunotherapies: From immune evasion to Promising targeted cellular therapies" Front Immunog, vol. 8:745. PDF File: p. 1-6.
Lander et al. (2016) "Increased proportion of mature NK cells is associated with successful imatinib discontinuation in chronic myeloid leukemia" Leukemia, vol. 31(5), p. 1108-1116.

* cited by examiner

*Primary Examiner* — Elly-Gerald Stoica
(74) *Attorney, Agent, or Firm* — Pamela J. Sherwood; Bozicevic, Field & Francis LLP

(57) ABSTRACT

Compositions and methods are provided for classification and treatment of MYC-driven cancers, i.e. causally dependent on MYC as a result of, over-expression of MYC, constitutive expression of MYC, chromosomal translocation resulting in overactive MYC, and the like. Specifically, the methods comprising determining the MYC status of the cancer, and in a cancer that is determined to be driven by MYC activation, administering a composition of an effective dose of one or both of activated natural killer (NK) cells and a type 1 interferon.

12 Claims, 48 Drawing Sheets

Specification includes a Sequence Listing.

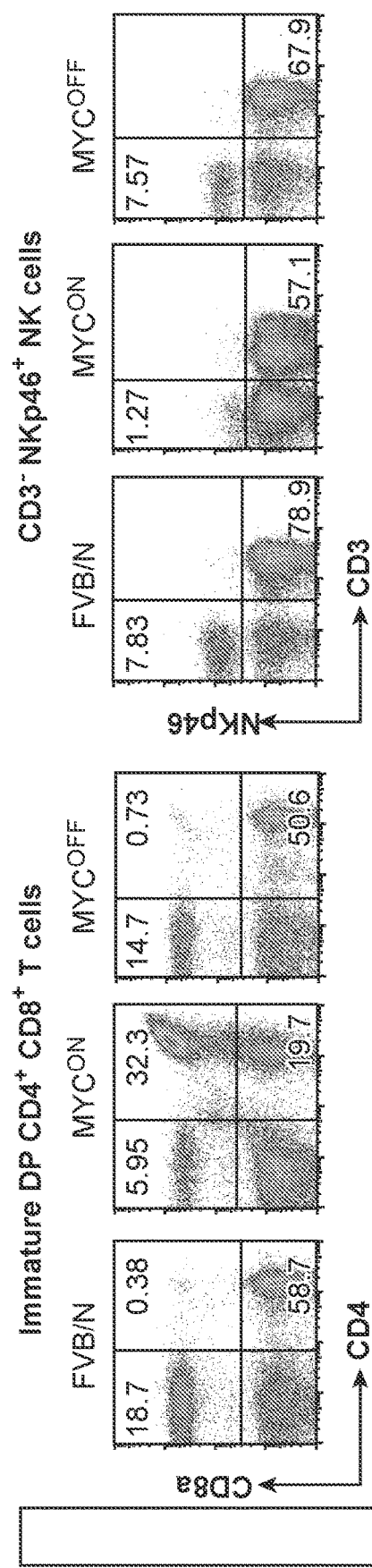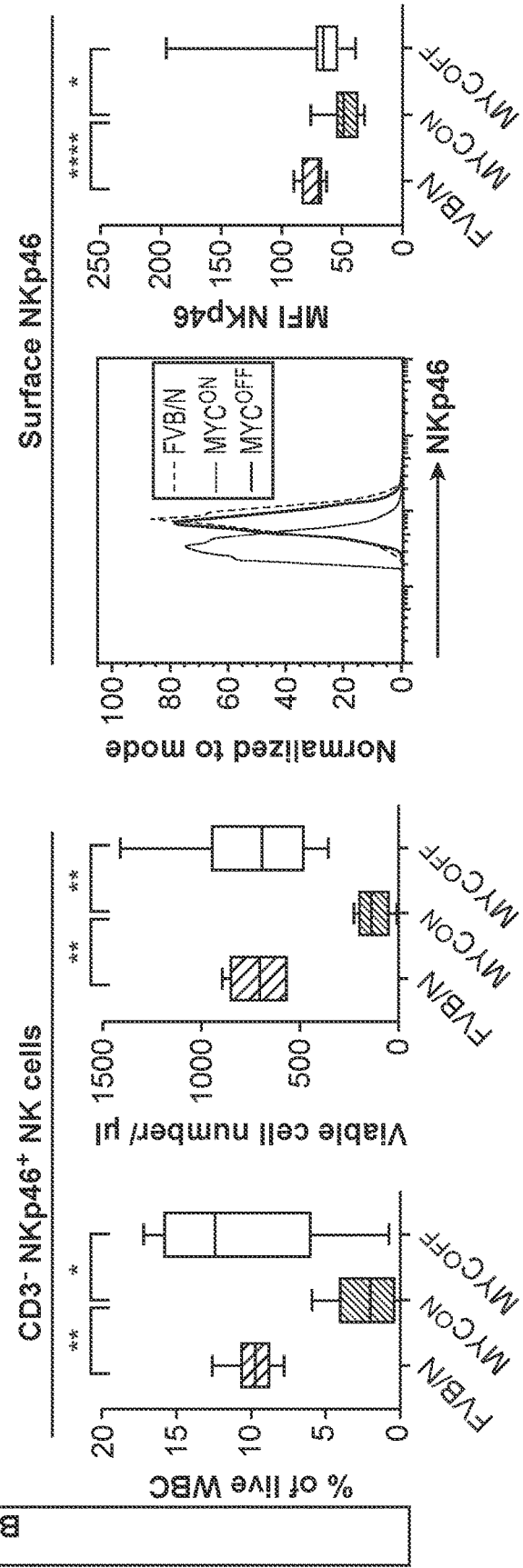
FIG. 2A
FIG. 2B
FIG. 2C
FIG. 2D
FIG. 2E

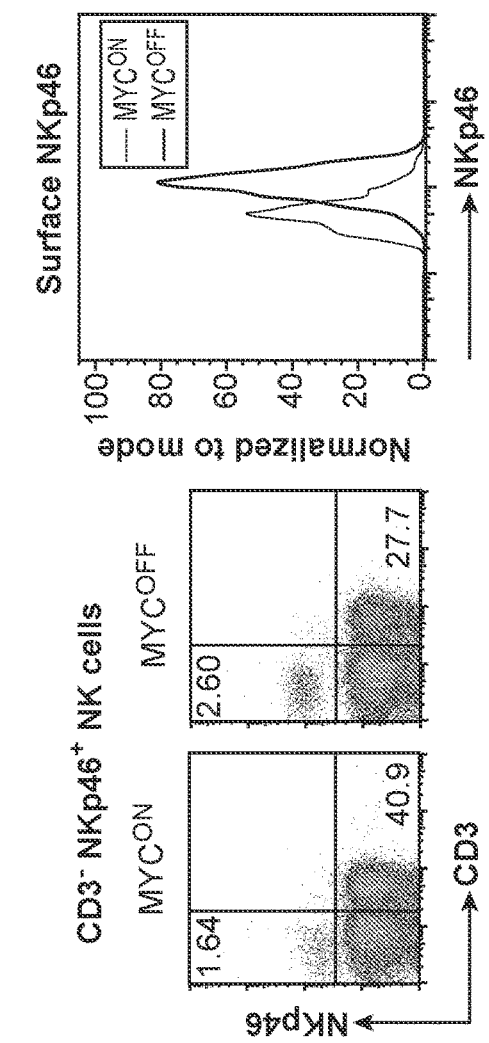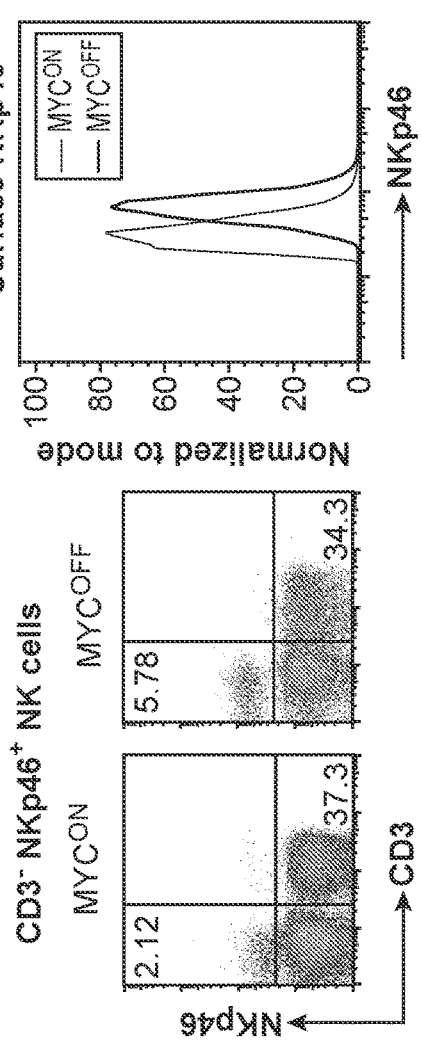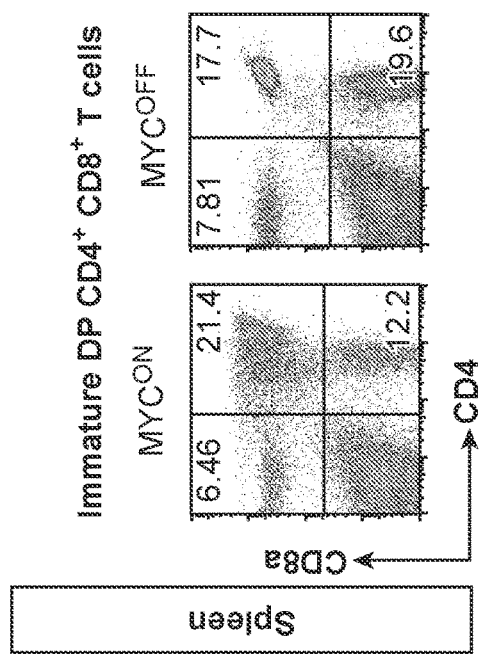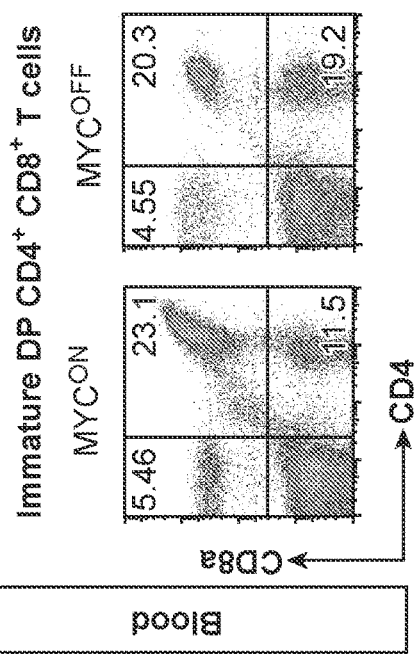

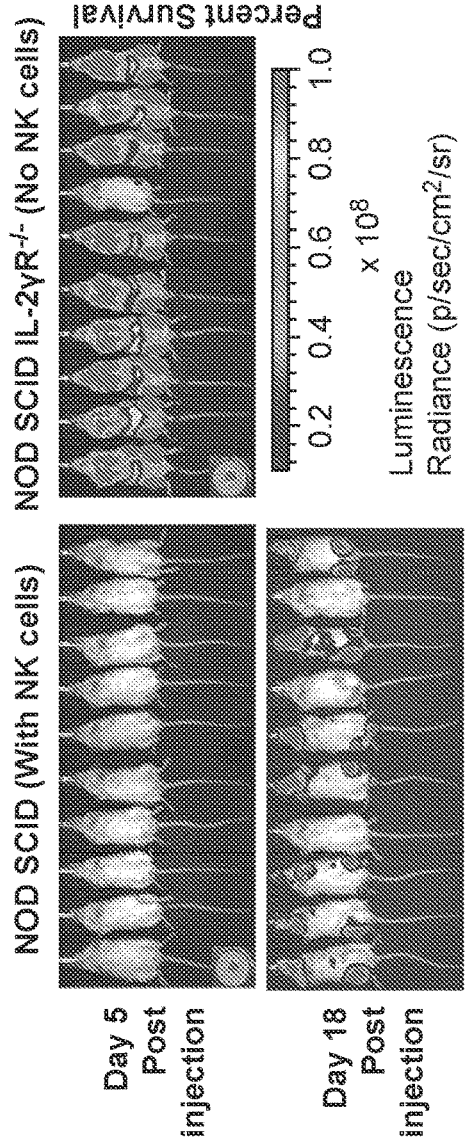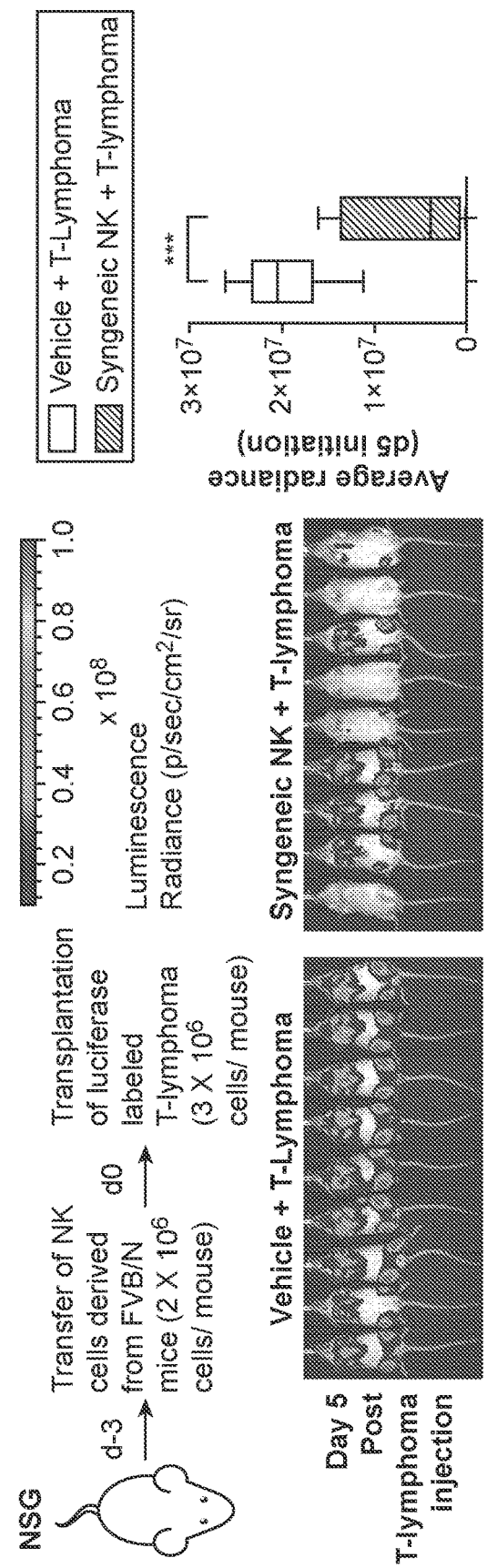
FIG. 3A
FIG. 3B
FIG. 3C
FIG. 3D

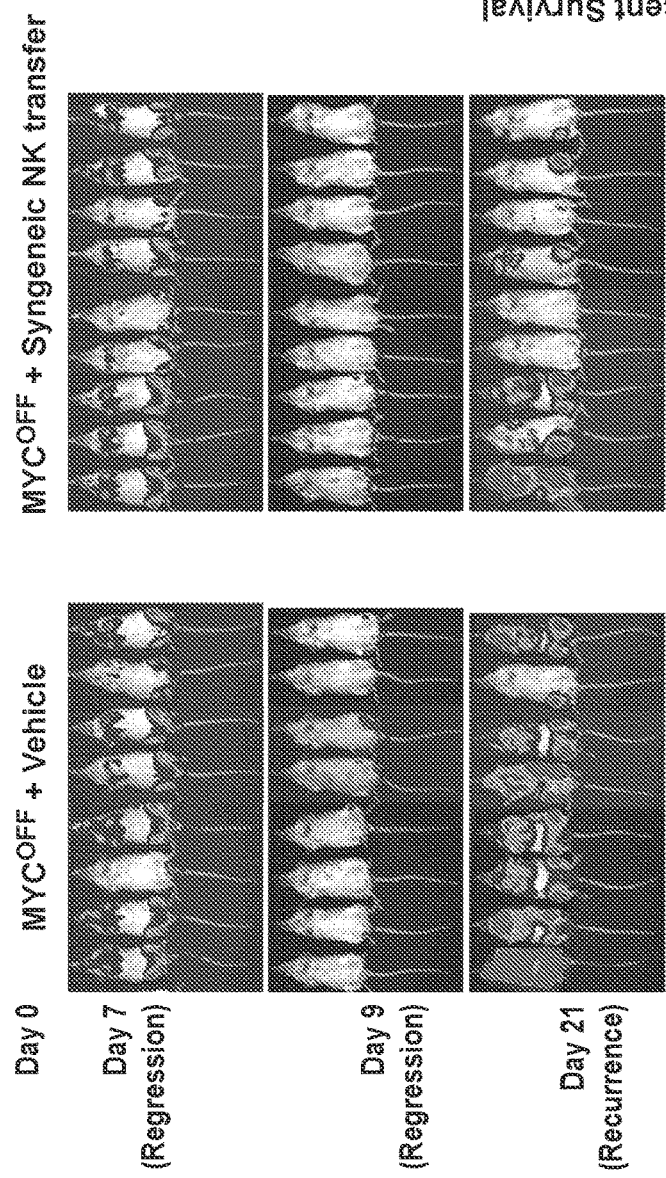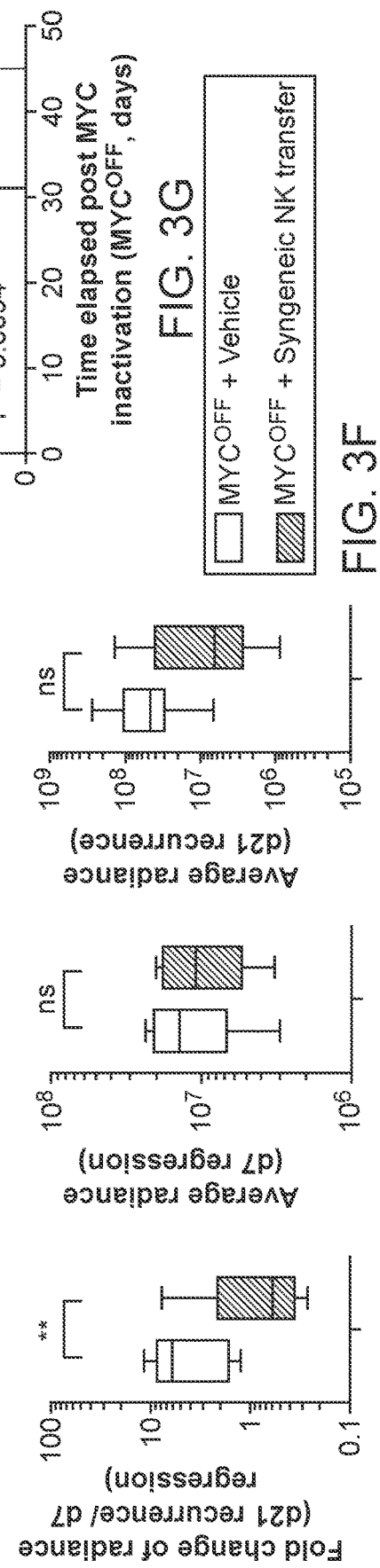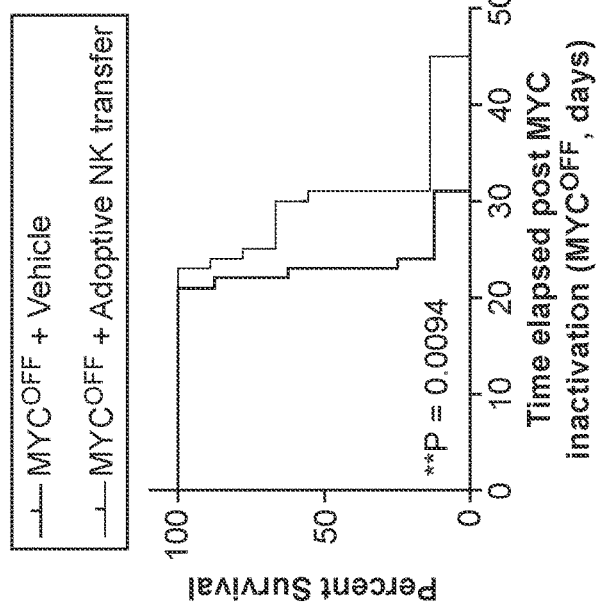

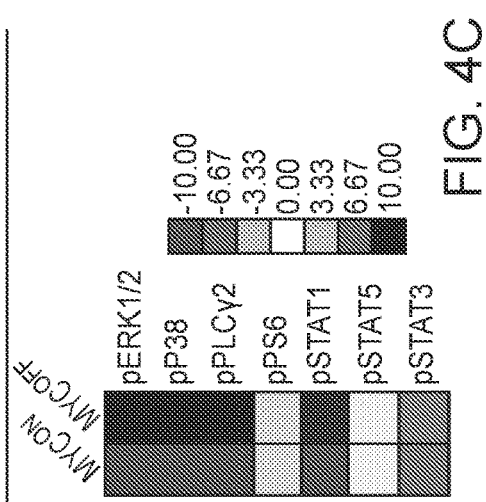
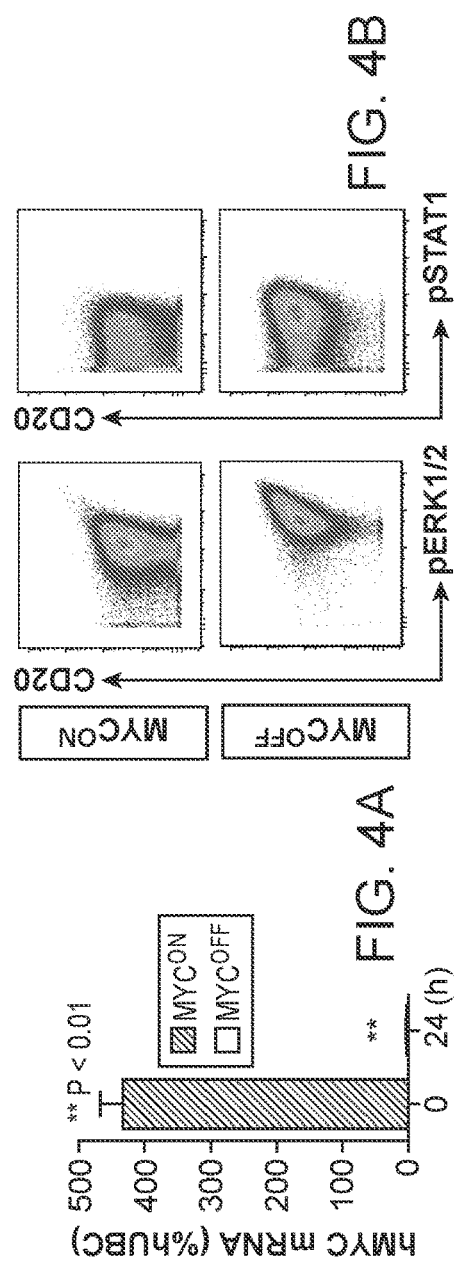
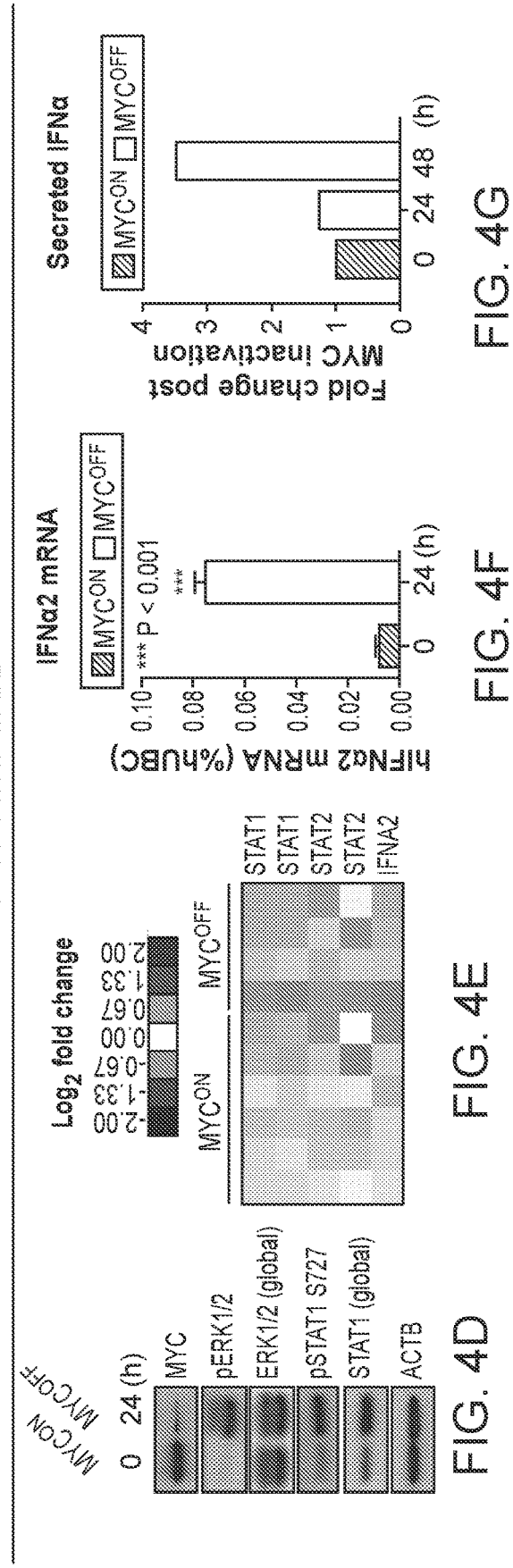
FIG. 4A  FIG. 4B  FIG. 4C  FIG. 4D  FIG. 4E  FIG. 4F  FIG. 4G

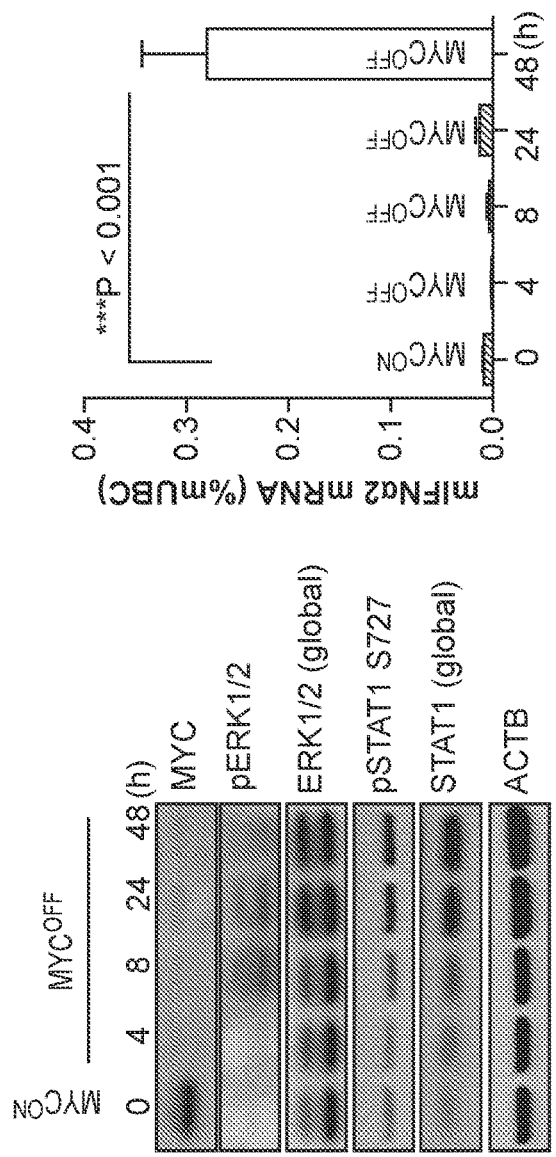
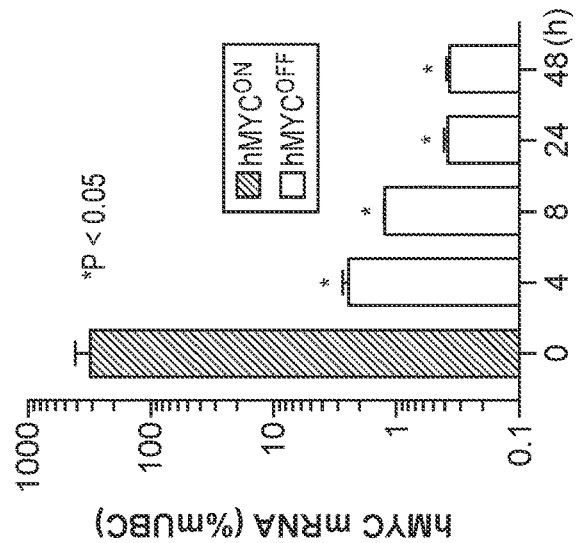
FIG. 4H  FIG. 4I  FIG. 4J

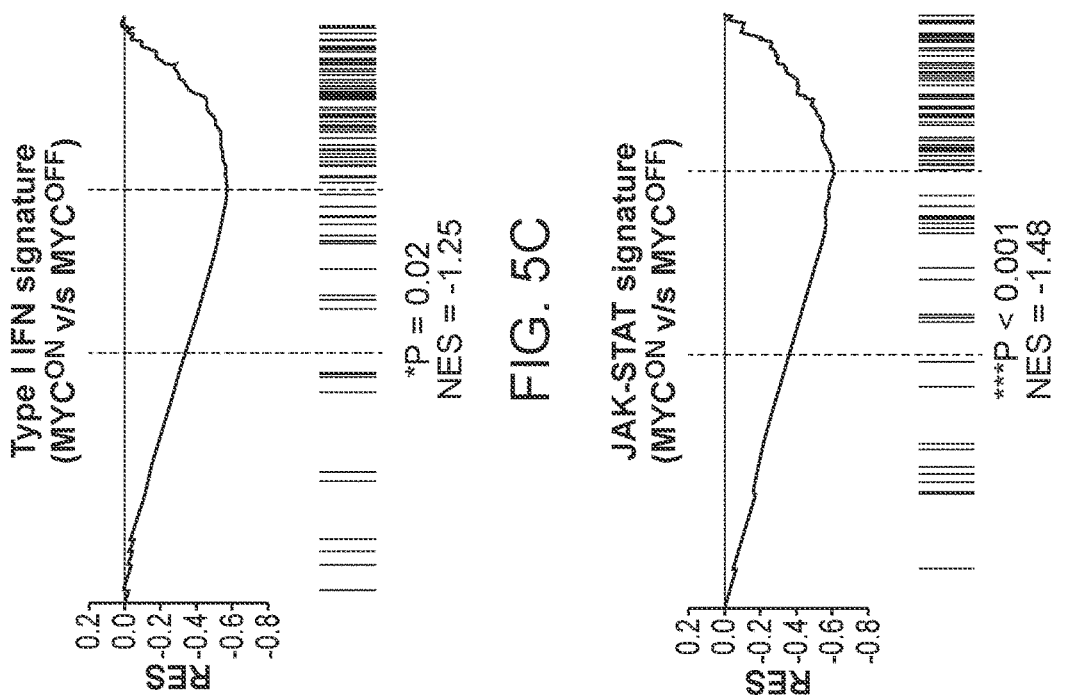
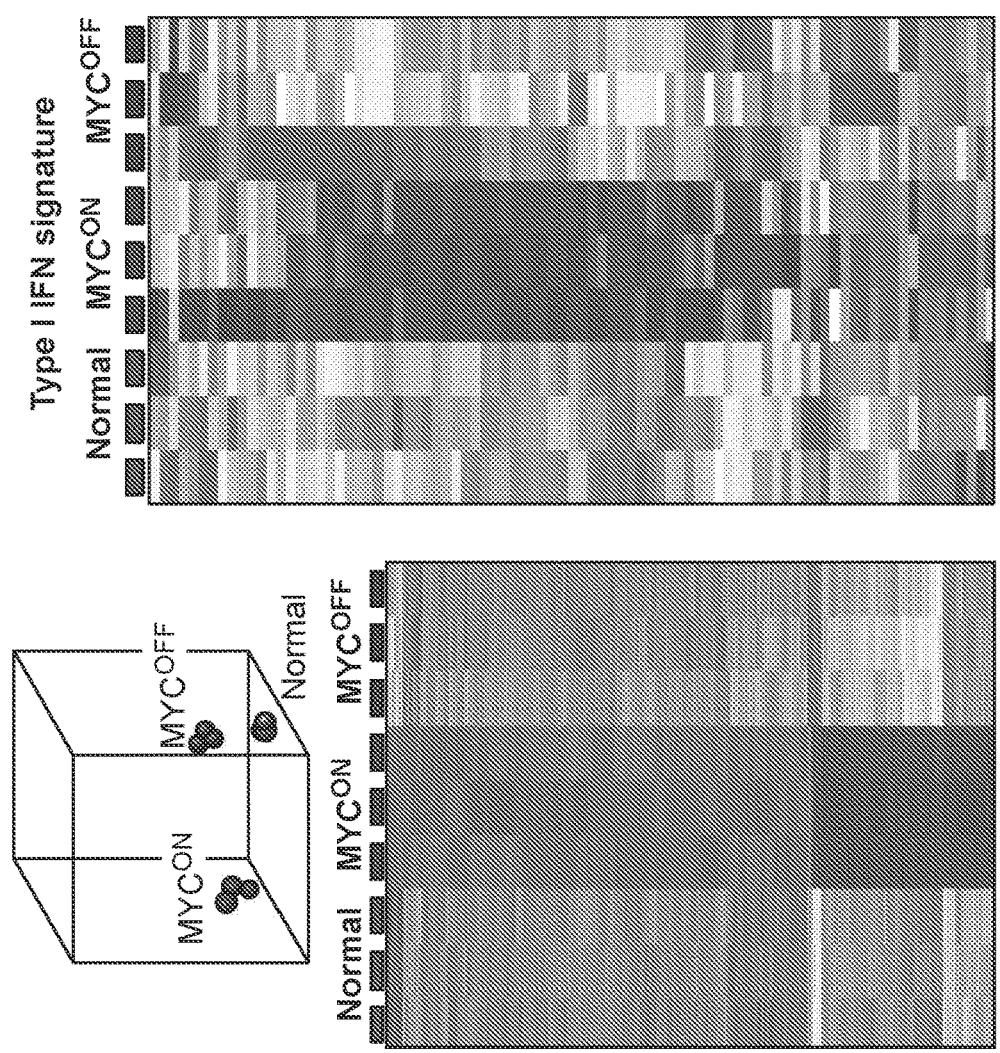
FIG. 5A
FIG. 5B
FIG. 5C
FIG. 5D

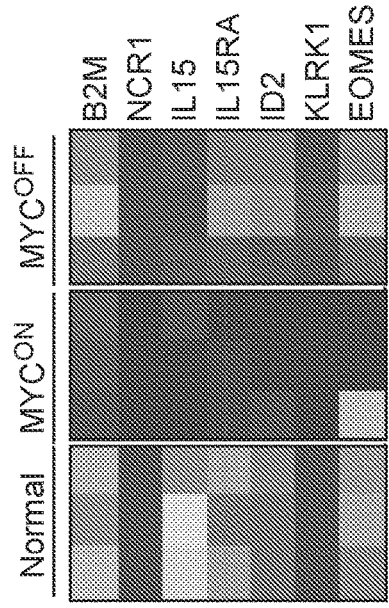
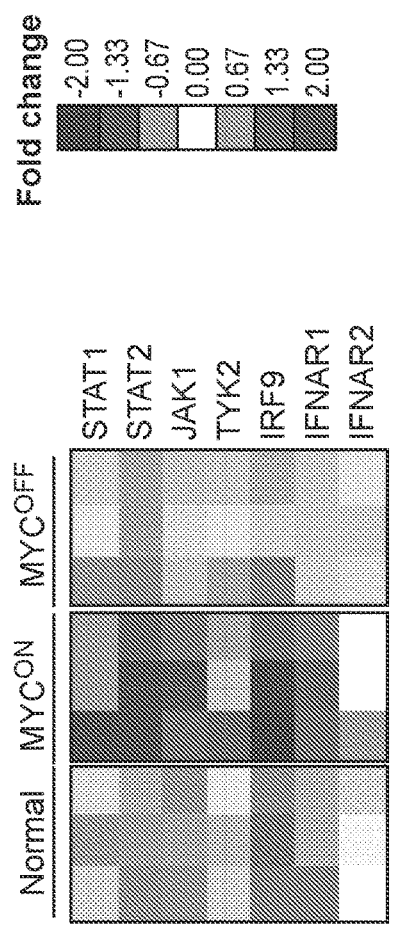
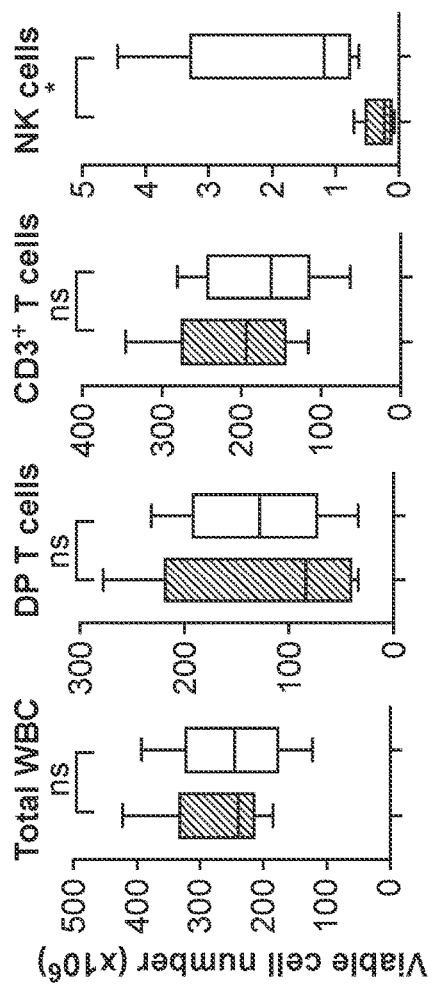
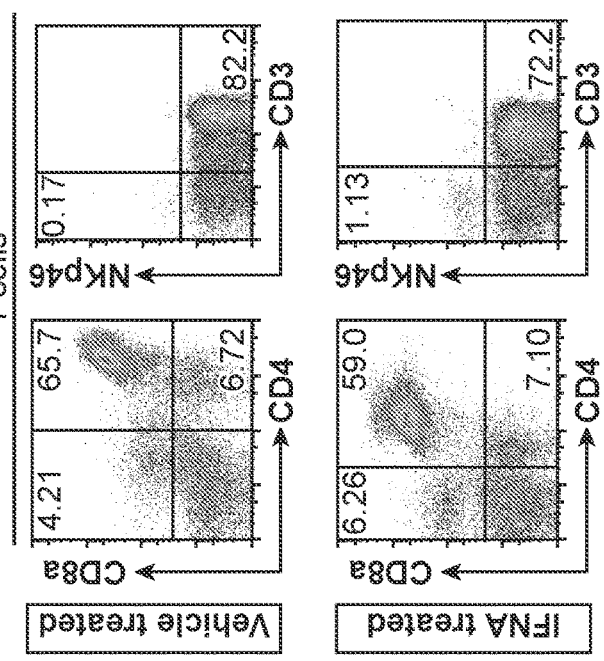
FIG. 5E   FIG. 5F
FIG. 5G   FIG. 5H   FIG. 5I   FIG. 5J   FIG. 5K

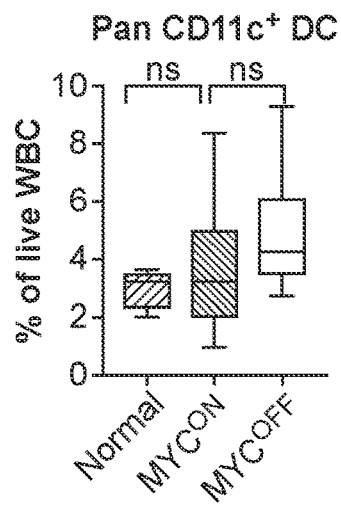
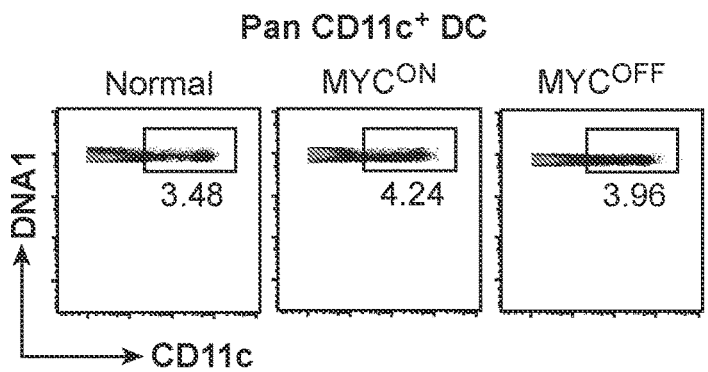
FIG. 10A
FIG. 10B
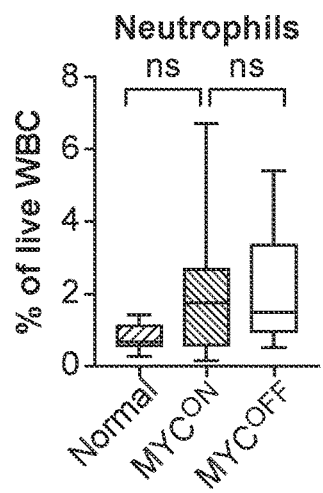
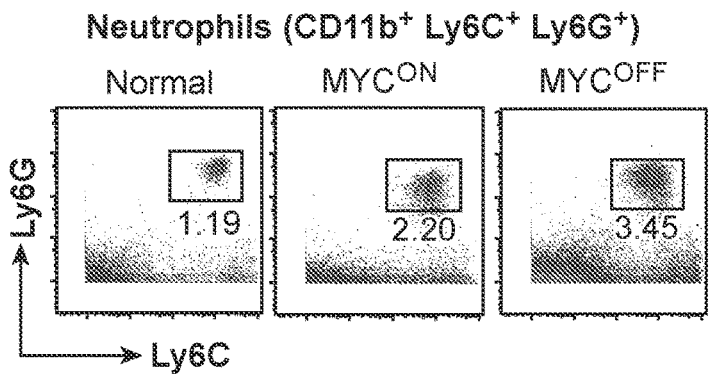
FIG. 10C
FIG. 10D
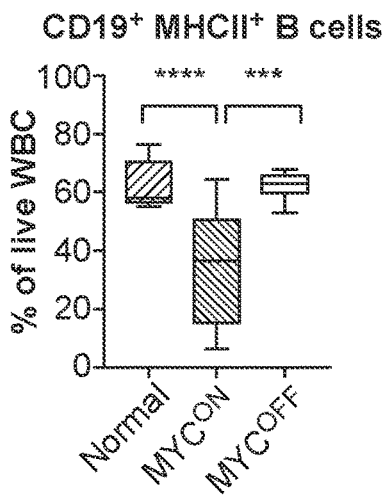
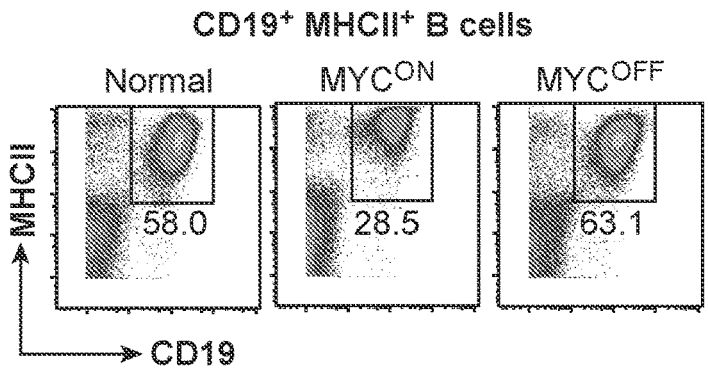
FIG. 10E
FIG. 10F

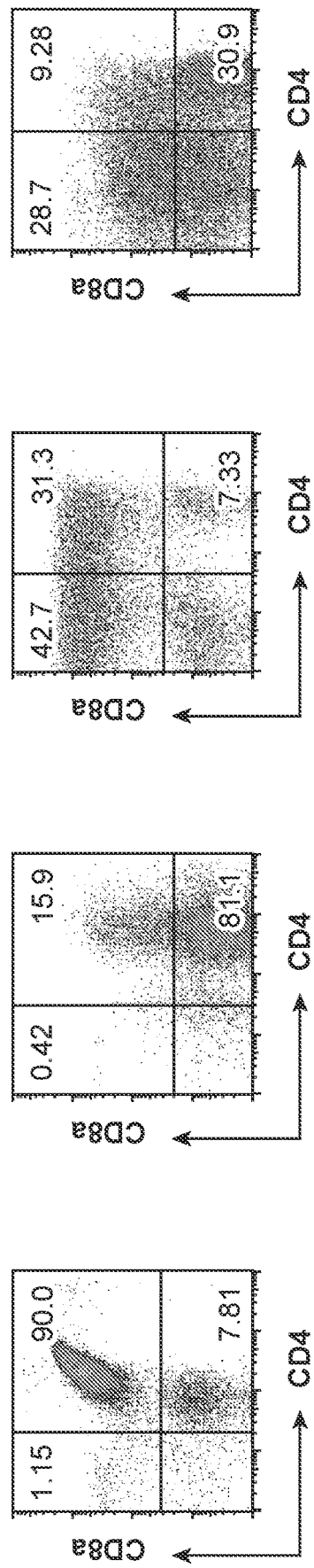

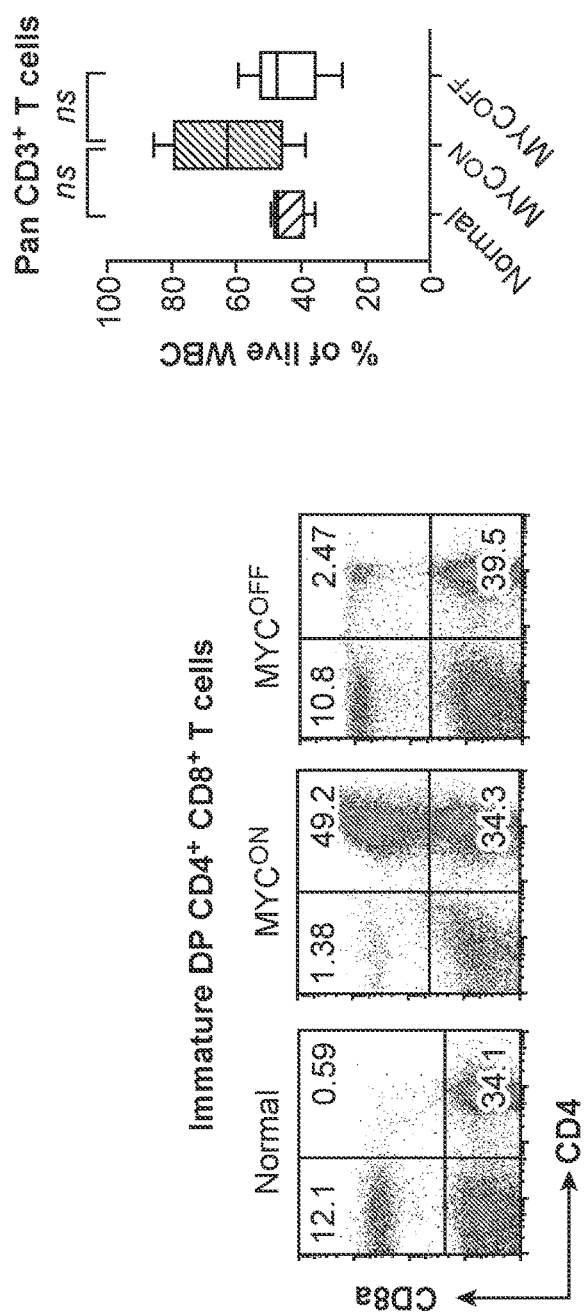
FIG. 14A
FIG. 14B
FIG. 14C
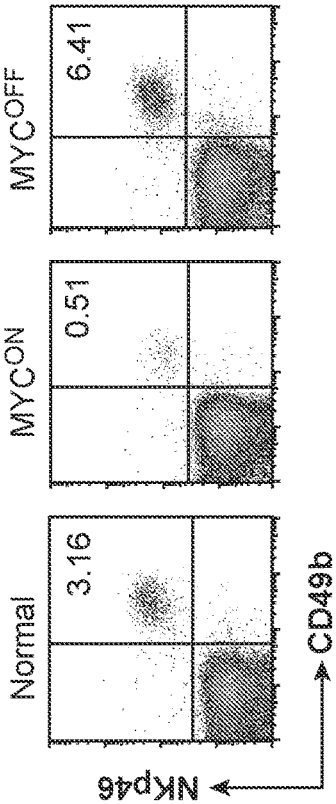
FIG. 14D
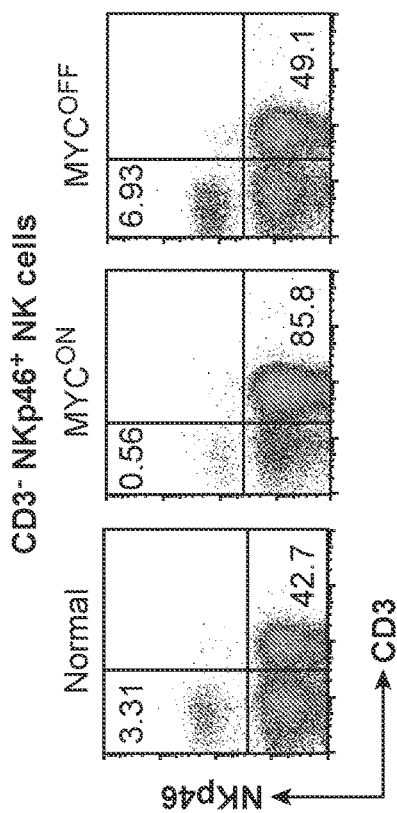
FIG. 14E

| | T cell % | | NK cell % | | B cell % | |
|---|---|---|---|---|---|---|
| | CyTOF | CIBERSORT | CyTOF | CIBERSORT | CyTOF | CIBERSORT |
| Normal 1 | 38.30 | 25.06 | 1.63 | 1.57 | 55.40 | 70.86 |
| Normal 2 | 36.70 | 24.70 | 1.46 | 2.22 | 56.60 | 67.82 |
| Normal 3 | 38.80 | 26.35 | 1.07 | 2.15 | 56.00 | 66.93 |
| MYC ON 1 | 52.90 | 52.73 | 0.043 | 0.76 | 36.50 | 35.18 |
| MYC ON 2 | 90.30 | 73.39 | 0.043 | 0.82 | 6.25 | 19.69 |
| MYC ON 3 | 70.80 | 60.16 | 0.057 | 0.48 | 21.10 | 31.08 |
| MYC OFF 1 | 31.10 | 25.75 | 1.53 | 4.71 | 58.20 | 53.98 |
| MYC OFF 2 | 27.10 | 17.15 | 1.27 | 3.25 | 52.80 | 61.70 |
| MYC OFF 3 | 15.00 | 23.59 | 2.24 | 2.52 | 66.40 | 57.01 |

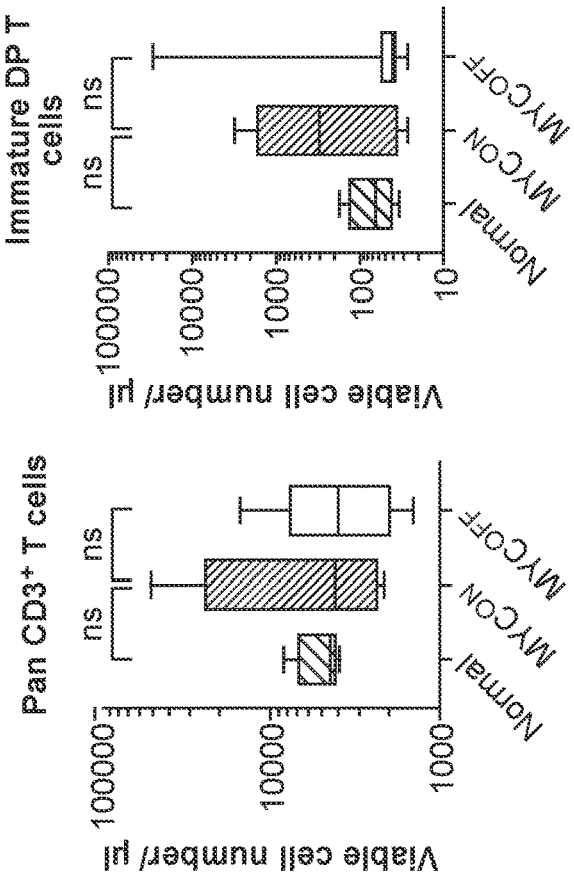
FIG. 16A
FIG. 16B
FIG. 16C
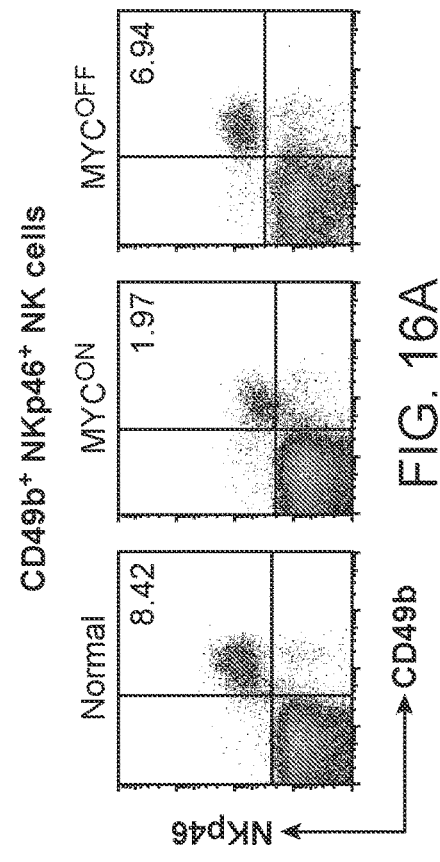
FIG. 16D
FIG. 16E
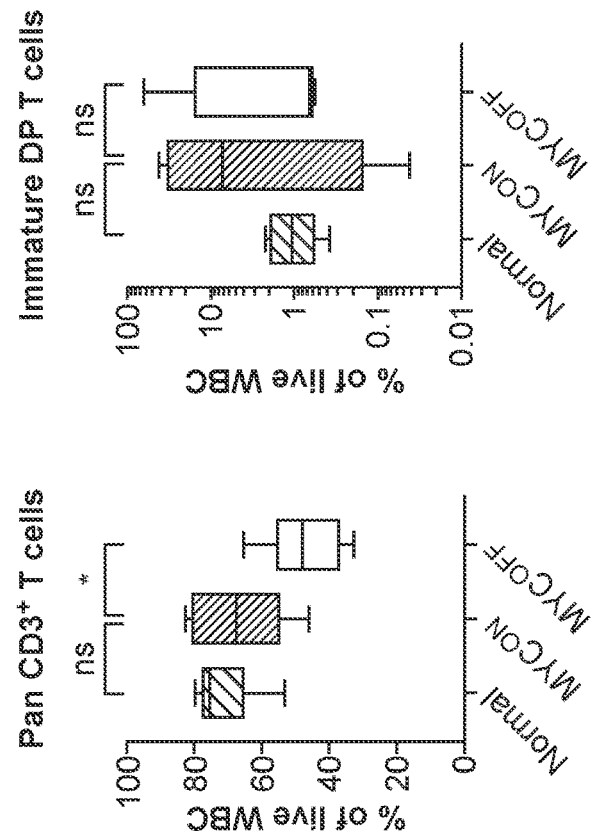
FIG. 16F

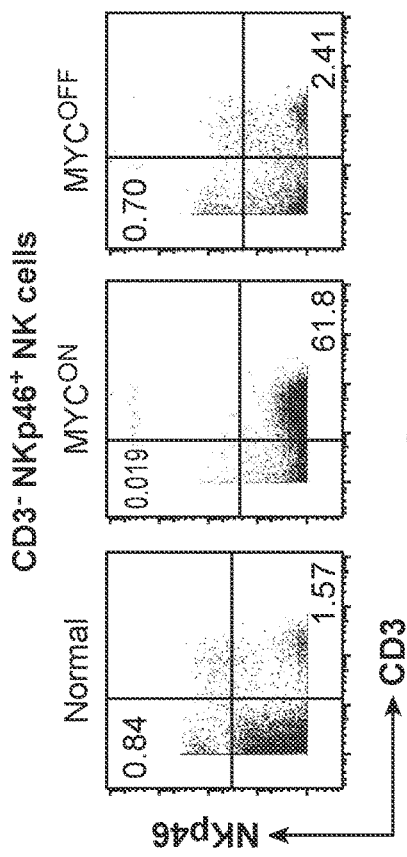
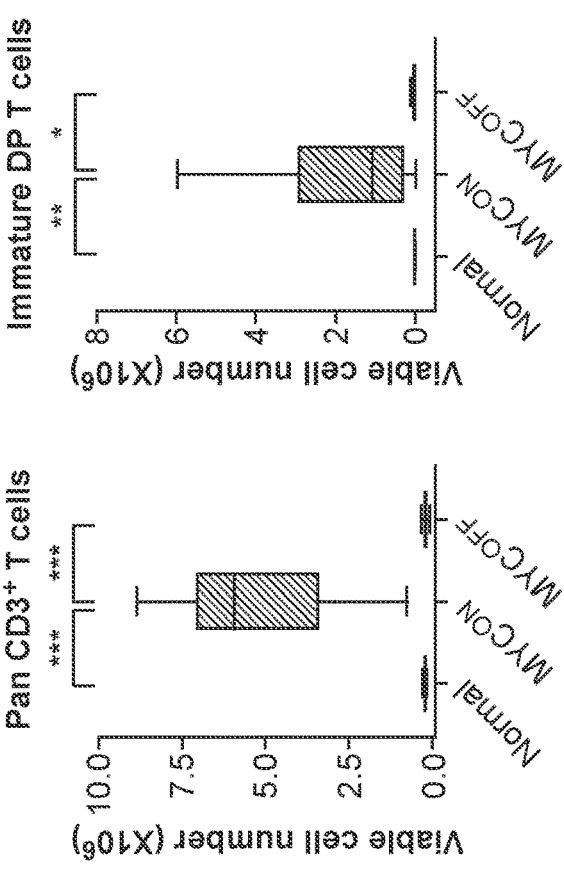
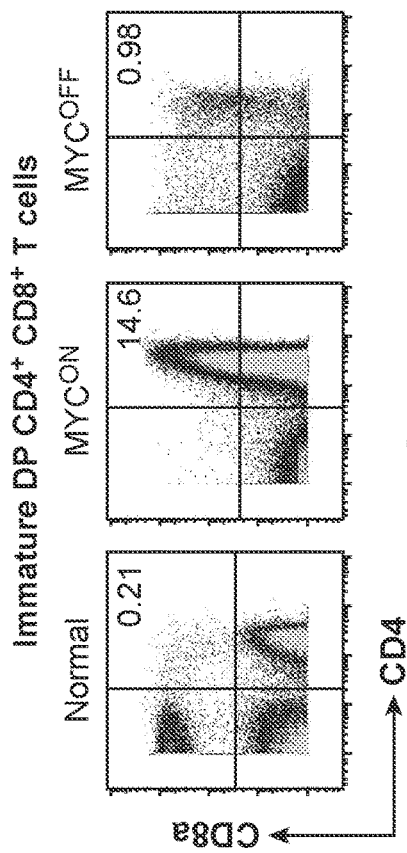
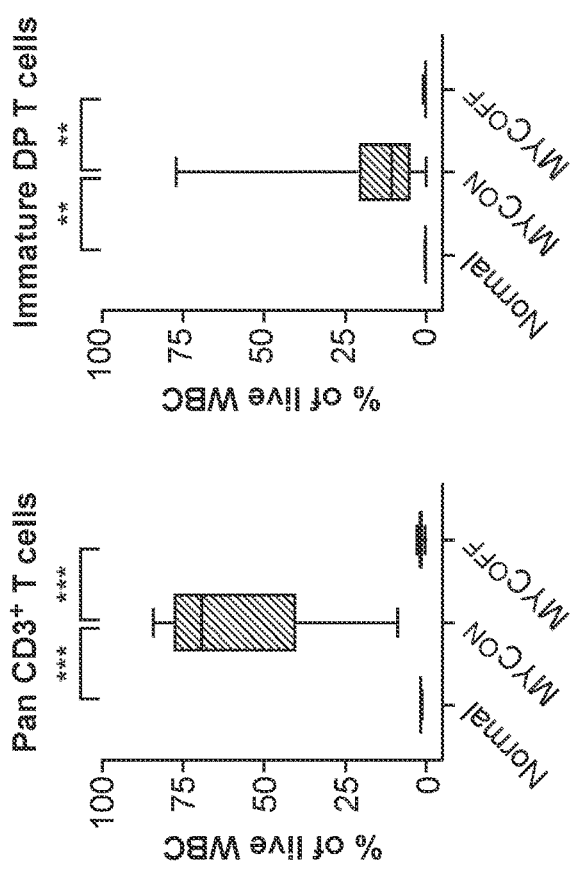
FIG. 17A
FIG. 17B
FIG. 17C
FIG. 17D
FIG. 17E
FIG. 17F

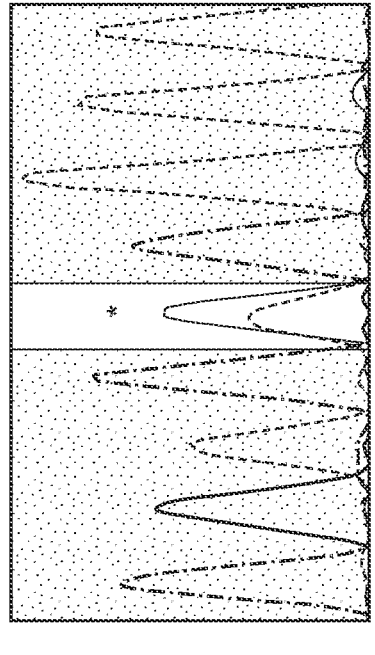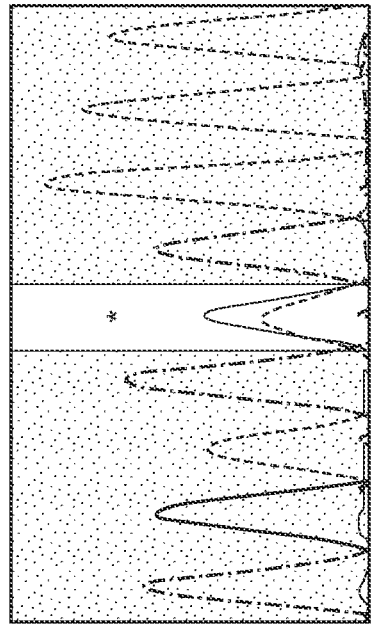
FIG. 20A
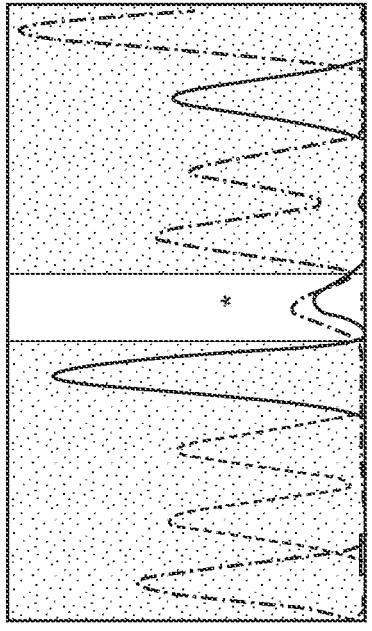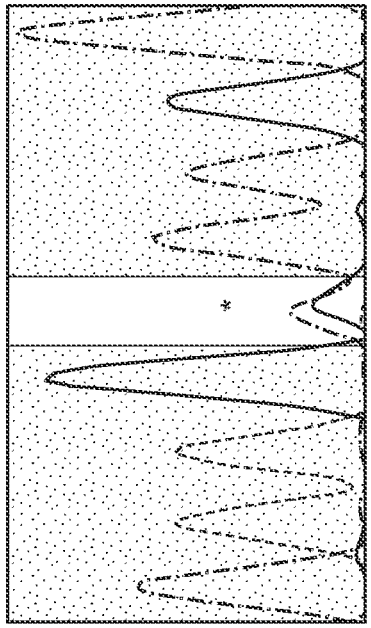
FIG. 20B

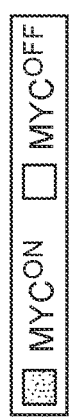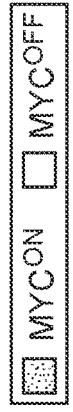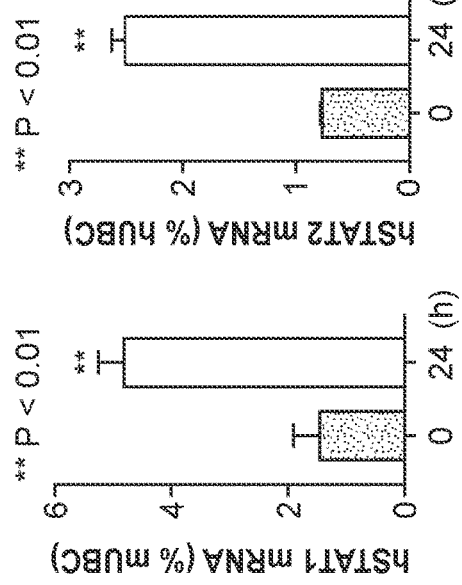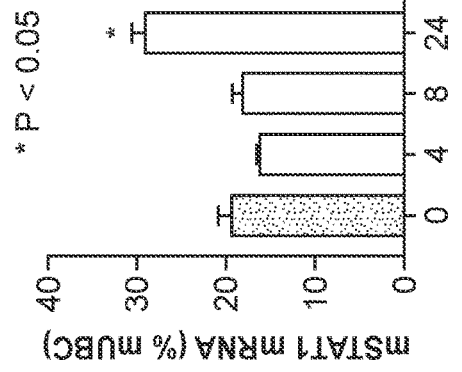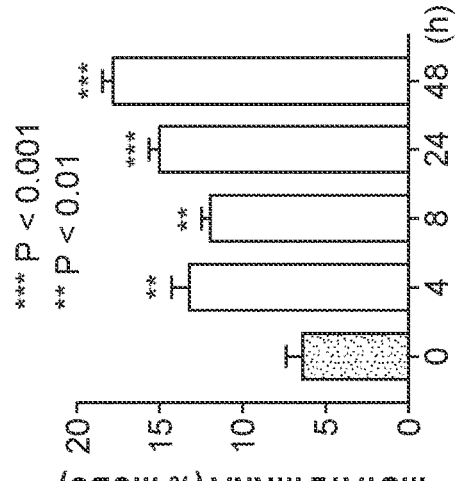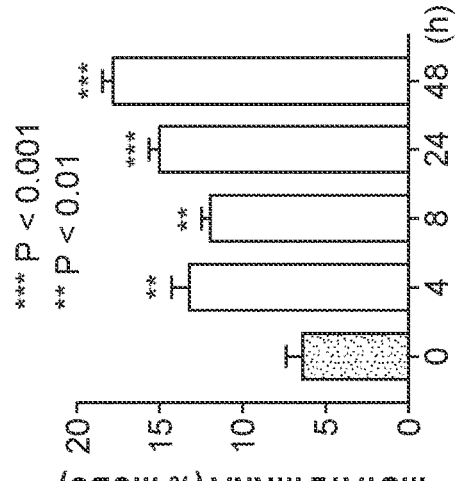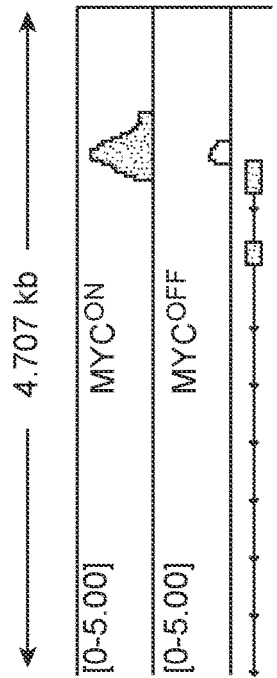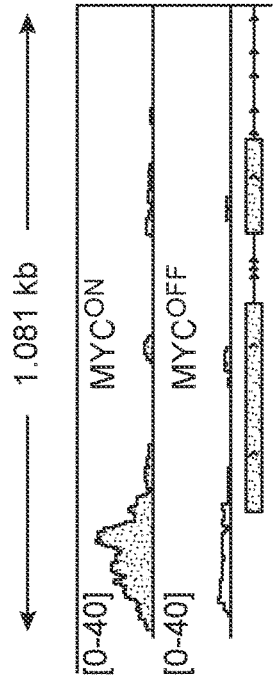
FIG. 22A  FIG. 22B  FIG. 22C  FIG. 22D  FIG. 22E  FIG. 22F

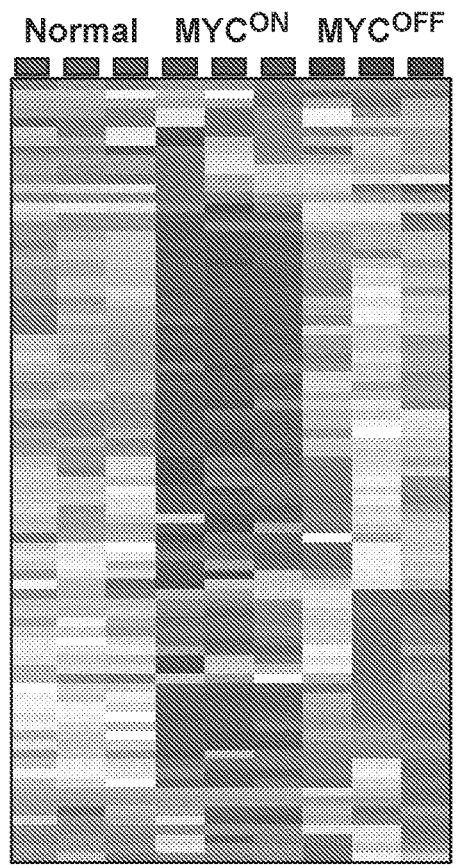
FIG. 25A
JAK-STAT signature
(Normal v/s MYC$^{ON}$)
P value 0.02
NES -1.48
FIG. 25B
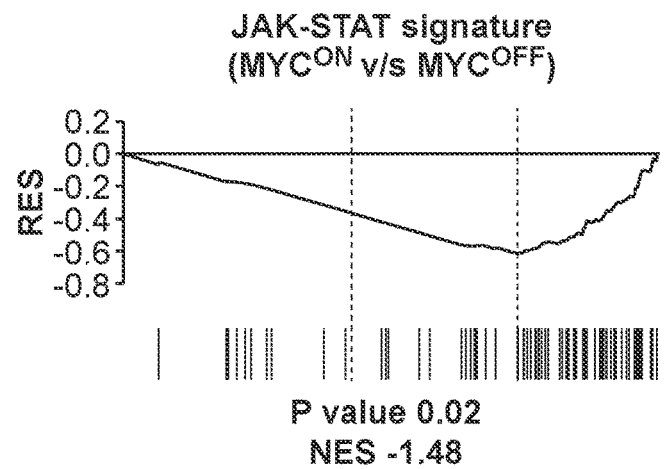
P value 0.02
NES -1.48
FIG. 25C

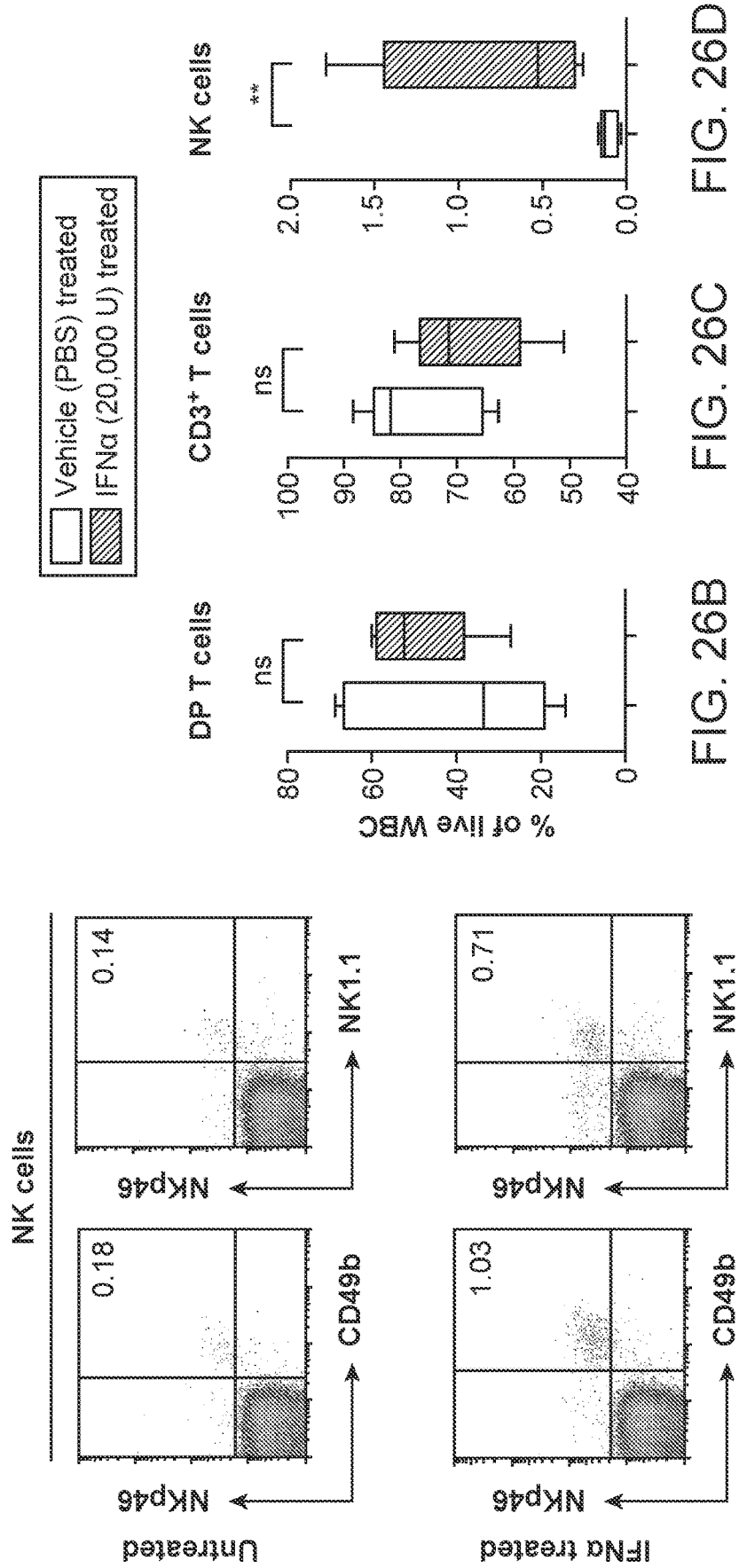

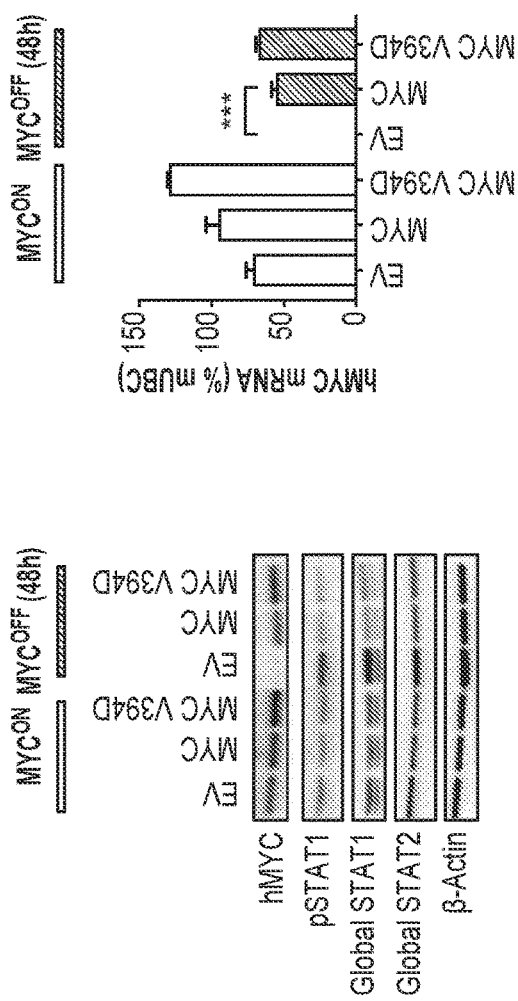
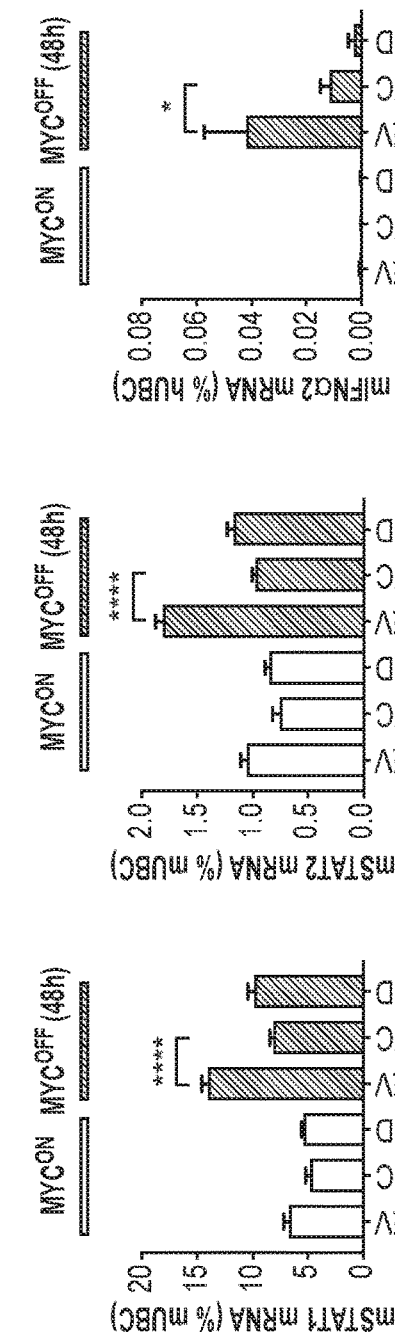
FIG. 28A
FIG. 28B
FIG. 28C
FIG. 28D
FIG. 28E

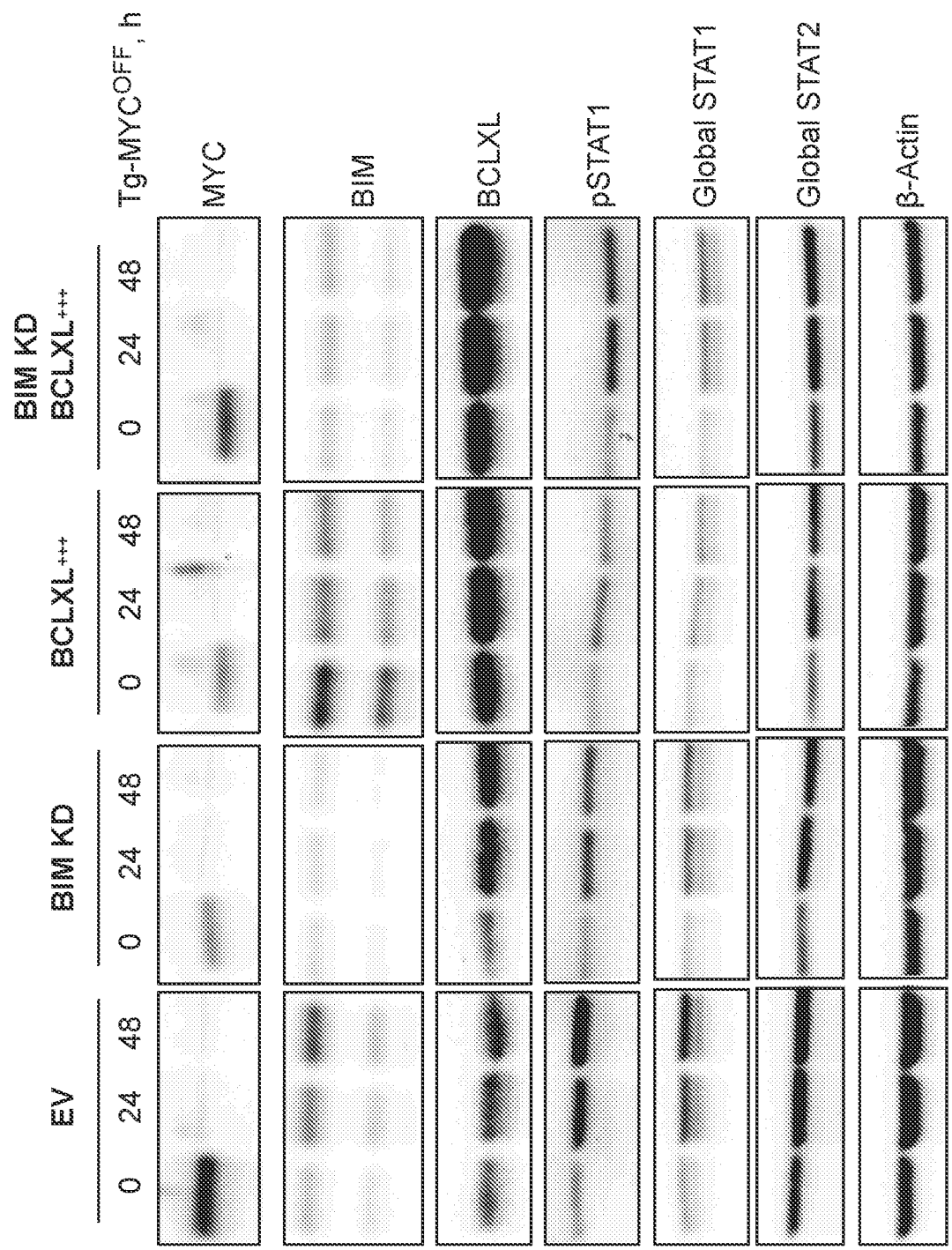

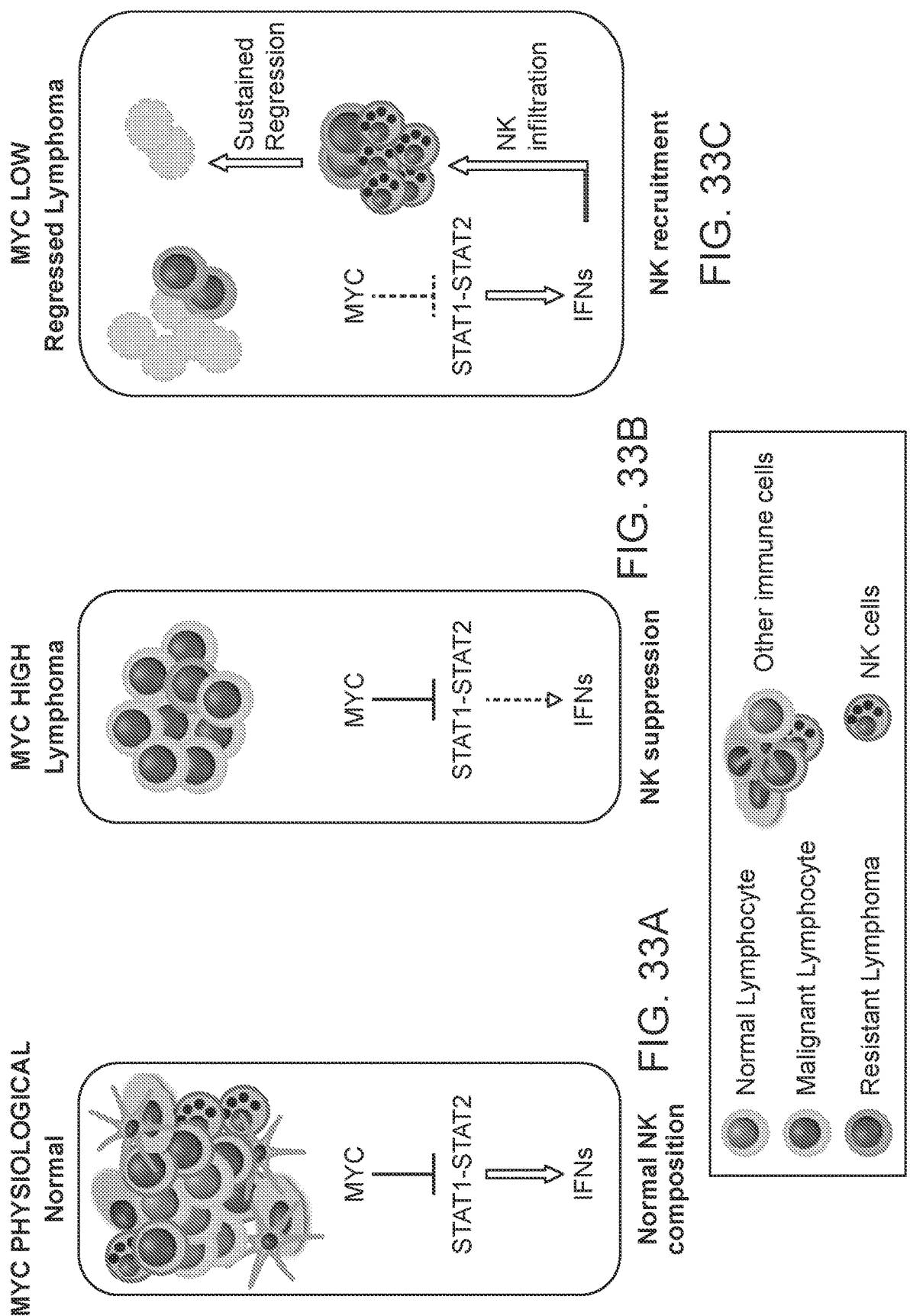

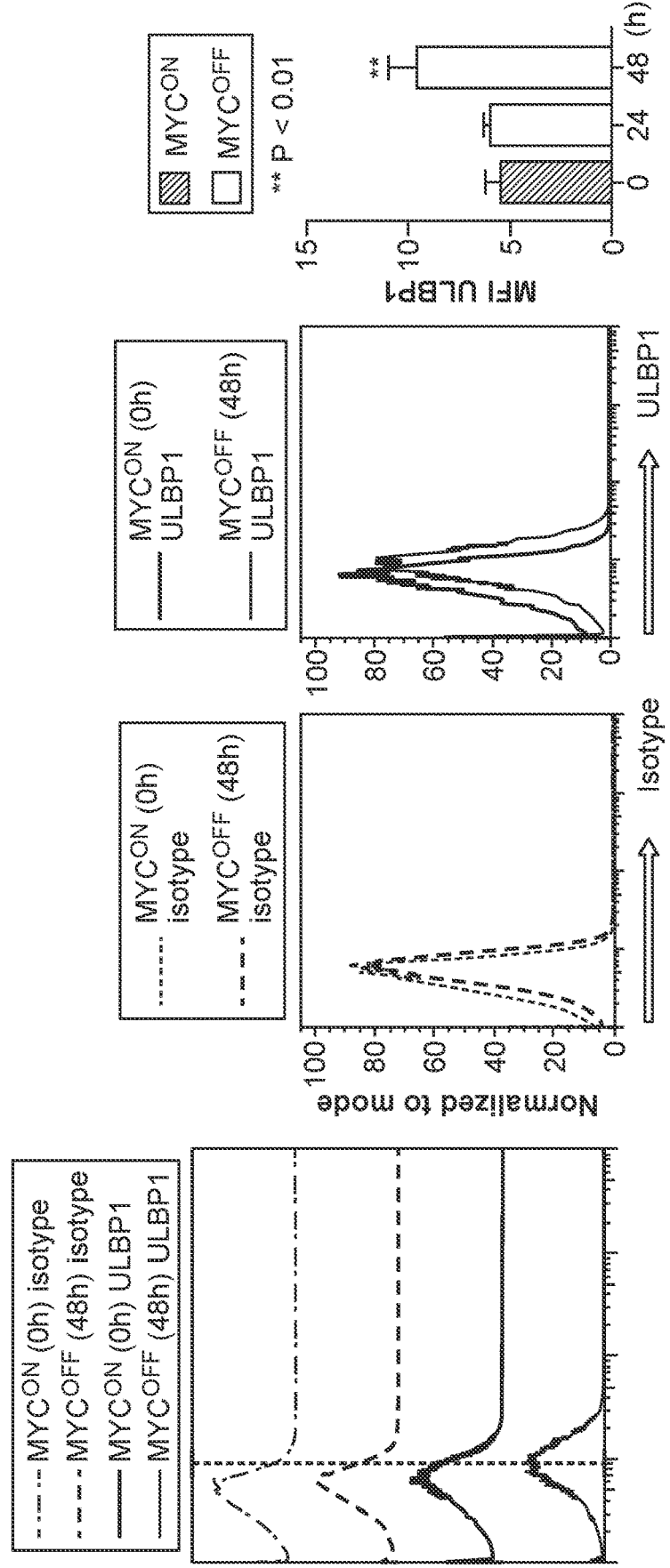

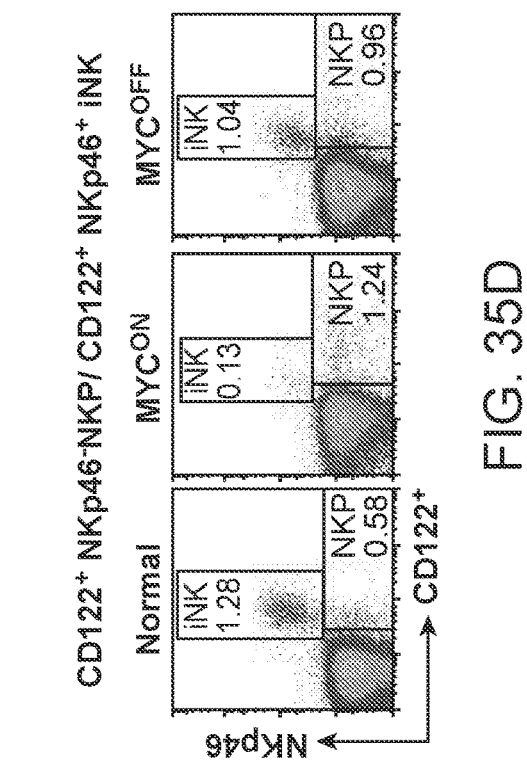
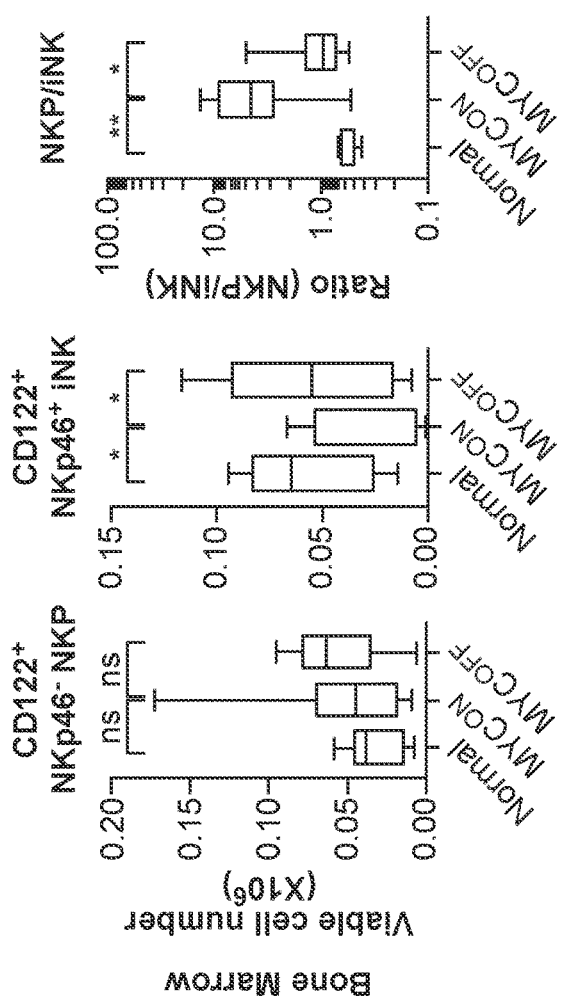
FIG. 35A  FIG. 35B  FIG. 35C  FIG. 35D

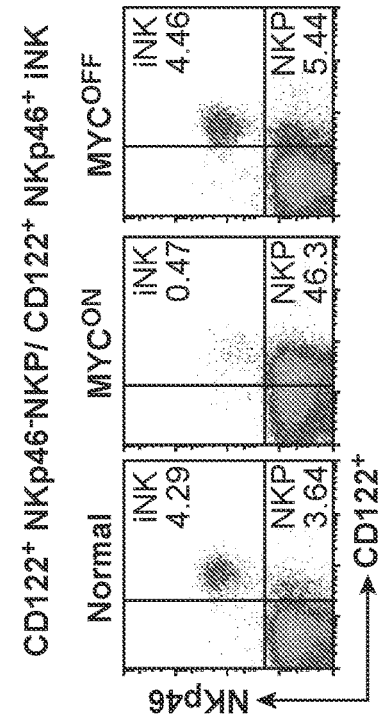
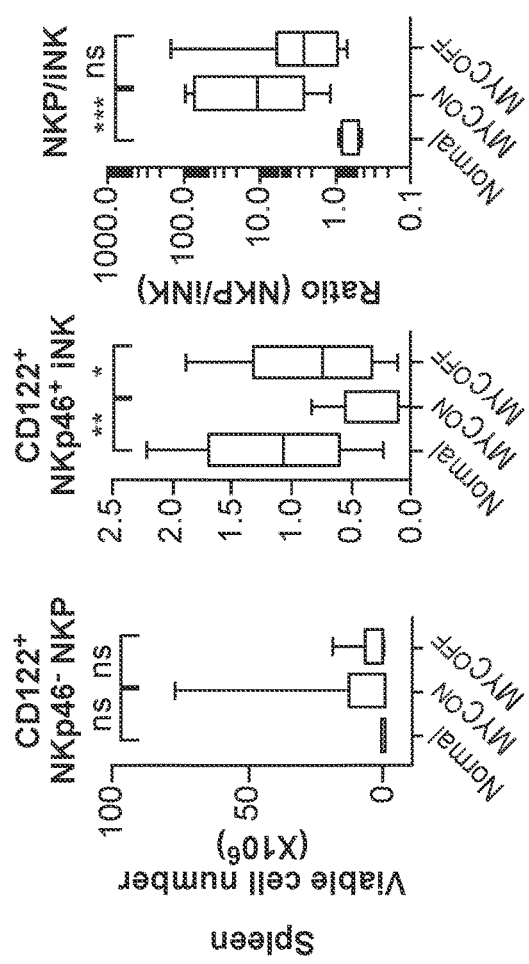
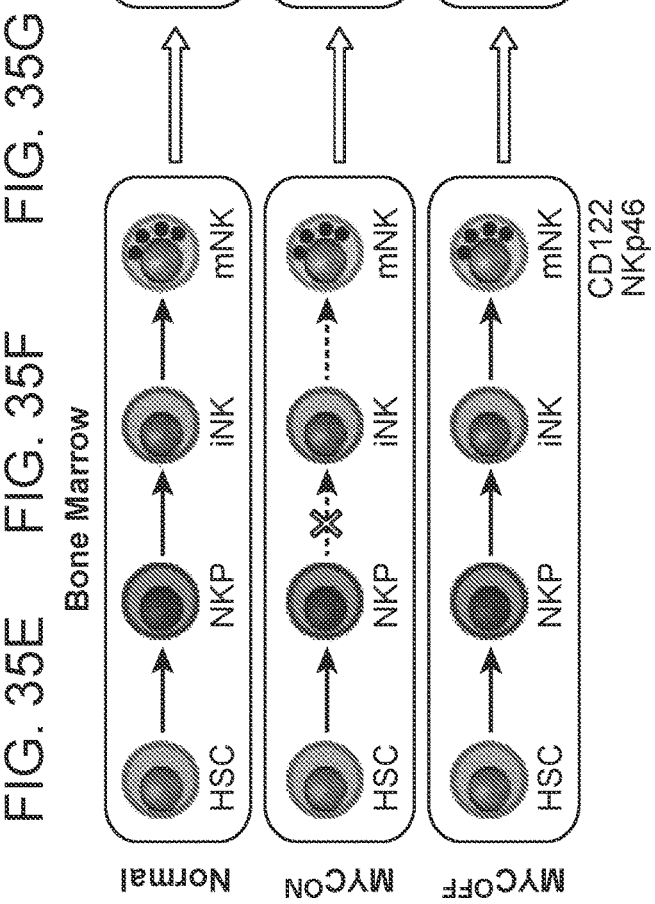
FIG. 35E  FIG. 35F  FIG. 35G  FIG. 35H
FIG. 35I

SEQUENCE LISTING

<160> NUMBER OF SEQ ID NOS: 33

<210> SEQ ID NO 1
<211> LENGTH: 20
<212> TYPE: DNA
<213> ORGANISM: Artificial sequence -continued

```
<220> FEATURE:
<223> OTHER INFORMATION: synthetic sequence

<400> SEQUENCE: 1
gtaacgatga agccctggag                                                   20

<210> SEQ ID NO 2
<211> LENGTH: 20
<212> TYPE: DNA
<213> ORGANISM: Artificial sequence
<220> FEATURE:
<223> OTHER INFORMATION: synthetic sequence

<400> SEQUENCE: 2
aaatgctttc tccgctctga                                                   20

<210> SEQ ID NO 3
<211> LENGTH: 20
<212> TYPE: DNA
<213> ORGANISM: Artificial sequence
<220> FEATURE:
<223> OTHER INFORMATION: synthetic sequence

<400> SEQUENCE: 3
cagccaatgt gaatgcagac                                                   20

<210> SEQ ID NO 4
<211> LENGTH: 20
<212> TYPE: DNA
<213> ORGANISM: Artificial sequence
<220> FEATURE:
<223> OTHER INFORMATION: synthetic sequence

<400> SEQUENCE: 4
ggagtgggat ggatgatgtc                                                   20

<210> SEQ ID NO 5
<211> LENGTH: 20
<212> TYPE: DNA
<213> ORGANISM: Artificial sequence
<220> FEATURE:
<223> OTHER INFORMATION: synthetic sequence

<400> SEQUENCE: 5
gctccaagaa aggacgaaca                                                   20

<210> SEQ ID NO 6
<211> LENGTH: 20
<212> TYPE: DNA
<213> ORGANISM: Artificial sequence
<220> FEATURE:
<223> OTHER INFORMATION: synthetic sequence

<400> SEQUENCE: 6
cccagtgctg gagaaattgt                                                   20

<210> SEQ ID NO 7
<211> LENGTH: 20
<212> TYPE: DNA
<213> ORGANISM: Artificial sequence
<220> FEATURE:
<223> OTHER INFORMATION: synthetic sequence

<400> SEQUENCE: 7
aaggtcctgg cacagatgag                                                   20
```

<210> SEQ ID NO 8
<211> LENGTH: 20
<212> TYPE: DNA
<213> ORGANISM: Artificial sequence
<220> FEATURE:
<223> OTHER INFORMATION: synthetic sequence

<400> SEQUENCE: 8
ggagggttgt attccaagca                                              20

<210> SEQ ID NO 9
<211> LENGTH: 20
<212> TYPE: DNA
<213> ORGANISM: Artificial sequence
<220> FEATURE:
<223> OTHER INFORMATION: synthetic sequence

<400> SEQUENCE: 9
tggtgaaatt gcaagagctg                                              20

<210> SEQ ID NO 10
<211> LENGTH: 20
<212> TYPE: DNA
<213> ORGANISM: Artificial sequence
<220> FEATURE:
<223> OTHER INFORMATION: synthetic sequence

<400> SEQUENCE: 10
cagacttccg ttggtggatt                                              20

<210> SEQ ID NO 11
<211> LENGTH: 20
<212> TYPE: DNA
<213> ORGANISM: Artificial sequence
<220> FEATURE:
<223> OTHER INFORMATION: synthetic sequence

<400> SEQUENCE: 11
gcctccattc tctggttcaa                                              20

<210> SEQ ID NO 12
<211> LENGTH: 20
<212> TYPE: DNA
<213> ORGANISM: Artificial sequence
<220> FEATURE:
<223> OTHER INFORMATION: synthetic sequence

<400> SEQUENCE: 12
tcctccatct tgcagctctt                                              20

<210> SEQ ID NO 13
<211> LENGTH: 21
<212> TYPE: DNA
<213> ORGANISM: Artificial sequence
<220> FEATURE:
<223> OTHER INFORMATION: synthetic sequence

<400> SEQUENCE: 13
tctccatcct atgttgcggt c                                            21

<210> SEQ ID NO 14
<211> LENGTH: 23
<212> TYPE: DNA
<213> ORGANISM: Artificial sequence
<220> FEATURE:
<223> OTHER INFORMATION: synthetic sequence

```
<400> SEQUENCE: 14
tccaagtaac tcggtcatca tct                                             23

<210> SEQ ID NO 15
<211> LENGTH: 20
<212> TYPE: DNA
<213> ORGANISM: Artificial sequence
<220> FEATURE:
<223> OTHER INFORMATION: synthetic sequence

<400> SEQUENCE: 15
agcccagtgt taccaccaag                                                 20

<210> SEQ ID NO 16
<211> LENGTH: 20
<212> TYPE: DNA
<213> ORGANISM: Artificial sequence
<220> FEATURE:
<223> OTHER INFORMATION: synthetic sequence

<400> SEQUENCE: 16
acccaagaac aagcacaagg                                                 20

<210> SEQ ID NO 17
<211> LENGTH: 20
<212> TYPE: DNA
<213> ORGANISM: Artificial sequence
<220> FEATURE:
<223> OTHER INFORMATION: synthetic sequence

<400> SEQUENCE: 17
ggggctgtcc agattatgaa                                                 20

<210> SEQ ID NO 18
<211> LENGTH: 20
<212> TYPE: DNA
<213> ORGANISM: Artificial sequence
<220> FEATURE:
<223> OTHER INFORMATION: synthetic sequence

<400> SEQUENCE: 18
ccaggagtga tccggaaata                                                 20

<210> SEQ ID NO 19
<211> LENGTH: 20
<212> TYPE: DNA
<213> ORGANISM: Artificial sequence
<220> FEATURE:
<223> OTHER INFORMATION: synthetic sequence

<400> SEQUENCE: 19
gcctcaagga caggatgaac                                                 20

<210> SEQ ID NO 20
<211> LENGTH: 20
<212> TYPE: DNA
<213> ORGANISM: Artificial sequence
<220> FEATURE:
<223> OTHER INFORMATION: synthetic sequence

<400> SEQUENCE: 20
tctcattcca gccagtgcta                                                 20

<210> SEQ ID NO 21
```

```
<211> LENGTH: 20
<212> TYPE: DNA
<213> ORGANISM: Artificial sequence
<220> FEATURE:
<223> OTHER INFORMATION: synthetic sequence

<400> SEQUENCE: 21
ctctctgggc tgtgatctcc                                                   20

<210> SEQ ID NO 22
<211> LENGTH: 20
<212> TYPE: DNA
<213> ORGANISM: Artificial sequence
<220> FEATURE:
<223> OTHER INFORMATION: synthetic sequence

<400> SEQUENCE: 22
actggttgcc atcaaactcc                                                   20

<210> SEQ ID NO 23
<211> LENGTH: 20
<212> TYPE: DNA
<213> ORGANISM: Artificial sequence
<220> FEATURE:
<223> OTHER INFORMATION: synthetic sequence

<400> SEQUENCE: 23
gcaagtcaag ctgctctgtg                                                   20

<210> SEQ ID NO 24
<211> LENGTH: 20
<212> TYPE: DNA
<213> ORGANISM: Artificial sequence
<220> FEATURE:
<223> OTHER INFORMATION: synthetic sequence

<400> SEQUENCE: 24
caaactcctc ctggggaaat                                                   20

<210> SEQ ID NO 25
<211> LENGTH: 20
<212> TYPE: DNA
<213> ORGANISM: Artificial sequence
<220> FEATURE:
<223> OTHER INFORMATION: synthetic sequence

<400> SEQUENCE: 25
aaggaggagg gcagaatcat                                                   20

<210> SEQ ID NO 26
<211> LENGTH: 20
<212> TYPE: DNA
<213> ORGANISM: Artificial sequence
<220> FEATURE:
<223> OTHER INFORMATION: synthetic sequence

<400> SEQUENCE: 26
cacacaggat ggcttgaaga                                                   20

<210> SEQ ID NO 27
<211> LENGTH: 20
<212> TYPE: DNA
<213> ORGANISM: Artificial sequence
<220> FEATURE:
<223> OTHER INFORMATION: synthetic sequence

<400> SEQUENCE: 27
```
aacacagcca gtgtgaatgc                                               20

<210> SEQ ID NO 28
<211> LENGTH: 20
<212> TYPE: DNA
<213> ORGANISM: Artificial sequence
<220> FEATURE:
<223> OTHER INFORMATION: synthetic sequence

<400> SEQUENCE: 28
agtgggatgg gtgatgtcag                                               20

<210> SEQ ID NO 29
<211> LENGTH: 20
<212> TYPE: DNA
<213> ORGANISM: Artificial sequence
<220> FEATURE:
<223> OTHER INFORMATION: synthetic sequence

<400> SEQUENCE: 29
ccgttttcat gacctcctgt                                               20

<210> SEQ ID NO 30
<211> LENGTH: 20
<212> TYPE: DNA
<213> ORGANISM: Artificial sequence
<220> FEATURE:
<223> OTHER INFORMATION: synthetic sequence

<400> SEQUENCE: 30
tgaatattcc ccgactgagc                                               20

<210> SEQ ID NO 31
<211> LENGTH: 20
<212> TYPE: DNA
<213> ORGANISM: Artificial sequence
<220> FEATURE:
<223> OTHER INFORMATION: synthetic sequence

<400> SEQUENCE: 31
ggaacagctg gagacatggt                                               20

<210> SEQ ID NO 32
<211> LENGTH: 20
<212> TYPE: DNA
<213> ORGANISM: Artificial sequence
<220> FEATURE:
<223> OTHER INFORMATION: synthetic sequence

<400> SEQUENCE: 32
ggctgggttt ctaccacaaa                                               20

<210> SEQ ID NO 33
<211> LENGTH: 20
<212> TYPE: DNA
<213> ORGANISM: Artificial sequence
<220> FEATURE:
<223> OTHER INFORMATION: synthetic sequence

<400> SEQUENCE: 33
ctgcgacgag gaggagaact                                               20

PROFILING AND TREATMENT OF MYC-ASSOCIATED CANCERS WITH NK CELLS AND TYPE 1 INTERFERON

CROSS-REFERENCE

This application claims benefit and is a 371 application of PCT Application No. PCT/US2018/065246, filed Dec. 12, 2018, which claims benefit of U.S. Provisional Patent Application No. 62/607,501 filed Dec. 19, 2017, which application is incorporated herein by reference in its entirety.

BACKGROUND OF THE INVENTION

The immune system's natural surveillance capacity to detect and destroy abnormal cells may prevent the development of many cancers. However, cancer cells are sometimes able to avoid detection and destruction by the immune system. For example, cancer cells can reduce the expression of tumor antigens on their surface, making it harder for the immune system to detect them; express proteins on their surface that induce immune cell inactivation; and/or induce cells in the microenvironment to release substances that suppress immune responses and promote tumor cell proliferation and survival. Cancer immunotherapies are being developed to enhance immune responses against tumors, by stimulating specific components of the immune system; or by counteracting signals produced by cancer cells that suppress immune responses.

Oncogene addiction is the phenomenon where a cancer becomes causally dependent on a single 'driver' oncogene for the maintenance of its proliferation and survival. Inhibiting the driver is the basis of oncogene targeted therapy. Hence, a potential Achilles' heel of human malignancies lies in their addiction to oncogenes such as MYC, RAS and BCR-ABL1. For example, targeted therapy has been successfully developed against BCR-ABL1 (Philadelphia/Ph$^+$)-induced leukemia. The MYC oncogene drives the pathogenesis of many hematopoietic malignancies, including Burkitt's lymphoma (BL) and Acute Lymphoblastic Leukemia (ALL). These malignancies are often "oncogene-addicted" to MYC, and effective inhibitors against MYC remain to be developed.

As new immunotherapies are developed, the underlying genetic changes of the cancer cell may be important for immunobiology mapping and identifying the most effective combination of agents for treatment.

SUMMARY OF THE INVENTION

Compositions and methods are provided for treatment of cancer, particularly cancers identified as over-expressing MYC. In some embodiments the cancer is MYC-driven, i.e. causally dependent on MYC as a result of, for example, over-expression of MYC, constitutive expression of MYC, chromosomal translocation resulting in overactive MYC; and the like. In some embodiments the MYC-dependent cancer is a hematologic cancer, including without limitation T-acute lymphocytic leukemia (T-ALL), Burkitt's lymphoma (BL), diffuse large B cell lymphoma (DLBCL); etc. It is shown herein that the increased MYC activity associated with these cancers causes down-regulation of STAT1 and STAT2 activity and concomitant decrease in IFNα levels. Importantly, there is a decrease in absolute numbers of mature cytotoxic natural killer (NK) cells in the hematopoietic system. Mature NK cells may be characterized as CD3-NKp46$^+$ cells.

In one embodiment of the invention, a MYC-driven cancer is treated by administration of immunotherapy comprising an effective dose or effective regimen of NK cells. The NK cells may be activated in vitro, or selected for high expression of NKp46. In some embodiments the NK cells are autologous. In other embodiments the NK cells are allogeneic. Repeated administration of NK cells may be required. In another embodiment of the invention, a MYC-driven cancer is treated by administration of immunotherapy comprising of an effective dose or effective regimen of a Type 1 interferon, e.g. IFNα. Administration of NK cells is optionally combined with administration of the interferon.

Cancers are optionally classified prior to treatment to determine suitability of an individual for the treatment. Such methods may include i) classifying a patient according to any of the method described below, and ii) administering immunotherapy to the patient, e.g. one or both of NK cells and Type 1 interferon, wherein the patient is classified as a patient predicted to exhibit a clinically beneficial response to the immunotherapy. A clinically beneficial response may be a longer progression-free survival, a longer overall survival and/or a longer time to subsequent therapy compared to a control subject who has not received the immunotherapy.

Methods of analysis for classification may include, without limitation, cytometry profiling by FACS, mass cytometry, etc.; phospho-cytometry; quantitative PCR, optionally combined with CIBERSORT, sequencing, microarray analysis; and the like, to determine the status of MYC and MYC-related pathways in the cancer cells; and/or to determine the immunobiology status of the patient. MYC status may be monitored by determining expression levels and/or phosphorylation status of MYC, STAT1, STAT2, etc. Immunobiology status parameters may include the number, maturation and cytotoxicity status of immune cells, particularly NK cells. As shown herein, changes in NK cell immunobiology can be systemic in a patient, and suitable biological samples for analysis may include hematopoietic cell samples which include, without limitation, blood, spleen, lymph node, bone marrow and the like. Patient samples may be obtained prior to initiation of immunotherapy.

In some embodiments, the classification step may include analyzing a gene expression profile of the patient sample to obtain the proportion of activated NK cells among the plurality of hematopoietic cells, for example by computing the proportion of activated NK cells based on the patient sample gene expression profile and a plurality of cell type-specific gene expression profiles.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

(FIG. 1A-1E) viSNE of CyTOF data depicting splenic CD3$^+$ T (FIG. 1A), splenic CD4$^+$ T (FIG. 1B), and CD8a$^+$ T (FIG. 1C), NKp46+NK (FIG. 1D), and CD19$^+$ B (FIG. 1E) cell compositions of one representative mouse from FVB/N (n=11), Eμ-tTA MYC$^{ON}$ (n=9), and Eμ-tTA MYC$^{OFF}$ (doxycycline 96 h, n=10) groups. (FIG. 1F-1I) Quantification of absolute counts of total WBC (FIG. 1F), immature CD3$^+$ CD8$^+$ CD4$^+$ DP lymphoma T cells (FIG. 1G), CD3$^-$ NKp46$^+$ mature NK (FIG. 1H), and CD19+ B (FIG. 1I) cells in FVB/N (n=11), Eµ-tTA MYC$^{ON}$ (n=9), and Eµ-tTA MYC$^{OFF}$ (doxycycline 96 h, n=10) mice subjected to CyTOF. (FIG. 1J) Median fluorescence intensity (MFI) of Nkp46 on splenic NK cells from FVB/N (n=11), Eµ-tTA MYC$^{ON}$ (n=9), and Eµ-tTA MYC$^{OFF}$ (doxycycline 96 h, n=10) mice. (FIG. 1K) Schematic depicting the reversible phenomenon of NK exclusion in MYC-driven lymphomas. P-values have been calculated using the Mann-Whitney test. P-values: ns=not significant; *p<0.05; p<0.01; *p<0.001; ****p<0.0001.

FIG. 2A-2K: MYC overexpression in T cell lymphoma systemically suppresses NK-mediated immune surveillance in lymphoid organs. (FIG. 2A-2B) Representative flow cytometry plots depicting percentages of circulating immature CD4+ CD8+ T (FIG. 2A), and CD3− NKp46+ NK (FIG. 2B) cells in FVB/N (n=6), Eµ-tTA MYC$^{ON}$ (n=6), and Eµ-tTA MYC$^{OFF}$ (doxycycline 96 h, n=6) mice. (FIG. 2C-2D) Quantification of percentages (FIG. 2C), and absolute counts per d of blood (FIG. 2D) of CD3− NKp46+ NK cells in FVB/N (n=6), Eµ-tTA MYC$^{ON}$ (n=6), and Eµ-tTA MYC$^{OFF}$ (doxycycline 96 h, n=6) mice. (FIG. 2E) Comparison of MFI of surface NKp46 on circulating NK cells in FVB/N (n=6), Eµ-tTA MYC$^{ON}$ (n=6), and Eµ-tTA MYC$^{OFF}$ (doxycycline 96 h, n=6) mice. (FIG. 2F-2G) Representative flow cytometry plots depicting percentages of splenic immature CD4+ CD8+ T (FIG. 2F), and CD3− NKp46+ NK (FIG. 2G) cells in Eµ-tTA MYC$^{ON}$ and Eµ-tTA MYC$^{OFF}$ (doxycycline 96 h) mice with comparable blast counts. (FIG. 2H) Comparison of surface NKp46 levels (MFI) on splenic NK cells from Eµ-tTA MYC$^{ON}$ and Eµ-tTA MYC$^{OFF}$ (doxycycline 96 h) mice with comparable blast counts. (FIG. 2I-2J) Representative flow cytometry plots depicting percentages of circulating immature CD4+ CD8+ T (FIG. 2I), and CD3− NKp46+ NK (FIG. 2J) cells in Eµ-tTA MYC$^{ON}$ and Eµ-tTA MYC$^{OFF}$ (doxycycline 96 h) mice with comparable blast counts. (FIG. 2K) Comparison of surface NKp46 levels (MFI) on circulating NK cells from Eµ-tTA MYC$^{ON}$ and Eµ-tTA MYC$^{OFF}$ (doxycycline 96 h) mice with comparable blast counts. P-values have been calculated using the Mann-Whitney test. P-values: ns=not significant; *p<0.05; p<0.01; **p<0.0001.

FIG. 3A-3G: NK cells present a barrier for MYC-driven lymphoma initiation and relapse. (FIG. 3A) Bioluminescence imaging (BLI) of NOD-SCID (n=10) and NOD-SCIDIL2Rγ$^{-/-}$ (n=10) mice transplanted with Eµ-tTA MYC mouse T-lymphoma cells post injection to monitor lymphoma engraftment and initiation. (FIG. 3B) Comparison of survival probabilities of NOD-SCID (n=10) and NOD-SCIDIL2Rγ$^{-/-}$ (NSG, n=10) T-lymphoma transplant recipients. (FIG. 3C) BLI of NSG T cell lymphoma transplant recipients comparing relapse rates upon MYC inactivation in the absence (MYC$^{OFF}$+vehicle, n=8) or presence of NK cells (MYC$^{OFF}$+Adoptive NK transfer, n=9). (FIG. 3D) Quantification of changes in BLI signal (left) and absolute signals (middle and right) at the time of lymphoma regression (d7 MYC$^{OFF}$) and lymphoma relapse (d21 MYC$^{OFF}$). (FIG. 3E) Comparison of survival probabilities of NSG T-lymphoma transplant recipients that received either vehicle (n=8) or adoptive NK transfer (n=9) at the time of MYC inactivation (MYC$^{OFF}$). (FIG. 3F) Comparison of survival probabilities of lymphomagenic Eµ-tTA/tet-O-MYC mice that were treated with either control IgG2a (n=12) or NK1.1 antibody (n=12) to deplete NK cells before overt lymphoma onset. (FIG. 3G) Representative flow cytometry plots depicting splenic immature CD4+ CD8+ T, CD3− NKp46+ NK, and NKp46+ NK1.1 NK cells in control antibody (n=12) or NK-depleted (n=12) Eµ-tTA MYC mice. P-values for all survival analyses have been calculated using the log-rank test. P-values for all other analyses have been calculated using Mann-Whitney test. P-values: ns=non-significant; *p<0.05; p<0.01; **p<0.0001.

FIG. 4A-4J: MYC inhibition leads to activation of ERK1/2-STAT1-Type I IFN signaling cascade. (FIG. 4A) Quantitative real time PCR for MYC in P493-6 BL human cells before and after MYC inhibition for 24 h by doxycycline (n=3, mean±s.d). (FIG. 4B) Phospho mass cytometry depicting changes in pERK1/2 and pSTAT1 levels before (MYC$^{ON}$) and after (MYC$^{OFF}$) MYC inactivation for 24 h in P493-6 cells. (FIG. 4C) Heatmap depicting changes in key phosphoproteins in the cell before (MYC$^{ON}$) and after (MYC$^{OFF}$) switching MYC off for 24 h in the P493-6 BL model. (FIG. 4D) Immunoblotting to validate changes in pERK1/2 and pSTAT1 observed by phospho-CyTOF. (FIG. 4E) Heat map depicting transcriptional changes in ERK1/2-STAT1/2 signaling cascade before (MYC$^{ON}$, n=6) and after MYC inactivation (MYC$^{OFF}$, 24 h, n=4) in P493-6 cells using expression arrays. (FIG. 4F) Quantitative real time PCR for Type I IFNα2 in P493-6 BL human cells before and after MYC inactivation for 24 h by doxycycline (n=3, mean±s.d). (FIG. 4G) Luminex assay depicting changes in Type I IFNα in P493-6 cells before and after MYC inactivation for 24 and 48 h. (FIG. 4H) Quantitative real time PCR for human MYC transgene in Eµ-tTA MYC transgenic mouse T-ALL cells before and after MYC inhibition by doxycycline for 4, 8, 24 and 48 h (n=3, mean s.d). (FIG. 4I) Immunoblotting to measure changes in ERK1/2-STAT1 signaling pre- and post-MYC transgene inactivation in Eµ-tTA MYC mouse T-ALL cells. (FIG. 4J) Quantitative real time PCR for Type I IFNα2 in Eµ-tTA MYC mouse T-ALL cells before and after MYC inactivation by doxycycline for 4, 8, 24 and 48 h (n=3, mean±s.d). All p values have been calculated using student t-test. *p<0.05; p<0.01; p<0.001.

FIG. 5A-5K: Activation of Type I IFN signaling leads to increased NK infiltration in MYC driven lymphomas. (FIG. 5A) Principal component analysis (PCA) and heatmap depicting gene expression signatures of bulk splenic samples derived from normal (n=3), Eµ-tTA MYC$^{ON}$ (n=4) and Eµ-tTA MYC (n=3) mice. (FIG. 5B) Heatmap showing suppression of JAK1-STAT1/2-Type I IFN signaling in spleens of Eµ-tTA MYC$^{ON}$ (n=4) mice when compared to normal (n=3) and Eµ-tTA MYC (n=3) mice. (FIG. 5C) Gene Set Enrichment Analysis (GSEA) depicting suppression of Type I IFN signature in spleens of Eµ-tTA MYC$^{OFF}$ (n=4) mice when compared to normal (n=3) mice. (FIG. 5D) GSEA depicting suppression of Type I IFN signature in spleens of Eµ-tTA MYC$^{ON}$ (n=4) mice when compared to Eµ-tTA MYC$^{OFF}$ (n=3) mice. (FIG. SE) Heatmap comparing expression of key genes in STAT1/2-Type I IFN signaling pathway in splenic samples from normal (n=3), Eµ-tTA MYC$^{ON}$ (n=4) and Eµ-tTA MYC$^{OFF}$ (n=3) mice. (FIG. 5F) Heatmap comparing expression of key NK cell genes in splenic samples from normal (n=3), Eµ-tTA MYC$^{ON}$ (n=4) and Eµ-tTA MYC$^{OFF}$ (n=3) mice. (FIG. 5G) Representative flow cytometry plots comparing percentages of CD4+ CD8+ DP T (left) and CD3− NKp46+ NK (right) cells between mice in IFNα-treated and vehicle (PBS)-treated groups with similar WBC counts. (FIG. 5H-5K) Quantification of absolute counts of total WBC (FIG. 5H), CD4+ CD8+ DP T (FIG. 5I), CD3+ pan T (FIG. 5J), and CD3− NKp46+ NK cells (FIG. 5K) in IFNα-treated and vehicle (PBS)-treated Eµ-MYC$^{ON}$ overt lymphoma bearing mice. P-values have been calculated using Mann-Whitney test ns=not significant, *p<0.05.

(FIG. 6A) Schematic describing the possible direct (A) and indirect (B) mechanisms by which MYC regulates STAT1-STAT2 and hence, the production of Type I IFNα. (FIG. 6B-6C) Immunoblotting to evaluate STAT1 and STAT2 before (−MEKi) and after (+MEKi) ERK1/2 inhibition with the MEK inhibitor (MEKi) when combined either with (−Tg-MYC) or without (+Tg-MYC) MYC inactivation, in P493-6 (FIG. 6B) and Eμ-tTA MYC T-lymphoma (FIG. 6C) cell lines. (FIG. 6D-6E) Quantitative real time PCR for Type I IFNα2 in P493-6 (FIG. 6D) and Eμ-tTA MYC T-lymphoma (FIG. 6E) cell lines, before and after combined inactivation of MYC and ERK1/2 (n=3, mean±s.d). (FIG. 6F) Immunoblotting in P493-6 BL cell lines expressing empty vector (EV), MYC overexpression vector (MYC), or a transcriptionally defunct MYC mutant that fails to bind MIZ1 (MYC V394D), pre- (Tg-MYC$^{ON}$) and post (Tg-MYC$^{OFF}$) MYC inactivation. (FIG. 6G-6I) Quantitative real time PCR for STAT1 (FIG. 6G), STAT2 (FIG. 6H), and Type I IFNα2 (FIG. 6I) in P493-6 BL cell lines expressing empty vector (EV), MYC overexpression vector (MYC), or a transcriptionally defunct MYC mutant that fails to bind MIZ1 (MYC V394D), pre- (Tg-MYC$^{ON}$) and post (Tg-MYC$^{OFF}$) MYC inactivation. All p values have been calculated using student t-test. *p<0.05; ***p<0.001.

(FIG. 7A) Comparison of MYC levels in mononuclear cells isolated from healthy human blood (n=20) and from blood of human T-ALL patients (n=48, GSE62156). (FIG. 7B-7E) CIBERSORT was performed using global gene expression profiles of mononuclear cells isolated from healthy human blood (n=20) and from blood of human T-ALL patients (n=48, GSE62156). Using CIBERSORT, we compared the compositions of T cell blasts (FIG. 7B), and different NK subsets in peripheral blood of normal individuals and T-ALL patients, namely, total NK (FIG. 7C), resting NK (FIG. 7D) and activated NK (FIG. 7E). (FIG. 7F-7G) Comparison of STAT1 (FIG. 7F) and STAT2 (FIG. 7G) levels in mononuclear cells isolated from healthy human blood (n=20) and from blood of human T-ALL patients (n=48, GSE62156). P-values were calculated using the Mann-Whitney test. (FIG. 7H-7I) Correlations between mRNA levels of MYC and STAT1 (FIG. 7H), or MYC and STAT2 (FIG. 7I) in classical MYC-driven human lymphoma patient samples (n=187, DLBCL, orange; n=34, BL, blue). (FIG. 7J-7K) Comparison of overall survival probabilities of BL patients (n=34, GSE4475) separated into high and low categories based on the median expression of the NK-associated gene KLRB1 (NK1.1, FIG. 7J) and, higher or lower than median levels of activated NK cells calculated by CIBERSORT (FIG. 7K). (FIG. 7L) Bivariate analysis comparing overall survival probabilities of BL (n=34, GSE4475) patients when divided into 4 groups based on combined levels of STAT1 and STAT2. P-values for all survival analyses have been calculated using the log-rank test. P-values for all other analyses have been calculated using Mann-Whitney test. P-values: ns=not significant; *p<0.05; p<0.01;**p<0.0001.

(FIG. 9A) Quantification of CD3$^+$ T and CD4$^+$ CD8$^+$ immature DP T cell percentages in normal (n=11), Eμ-tTA MYC$^{ON}$ (n=9), and Eμ-tTA MYC$^{OFF}$ (doxycycline 96 h, n=10) mice by CyTOF. (FIG. 9B) CyTOF dot plots showing percentages of DP T cells in one representative spleen from normal, Eμ-tTA MYC$^{ON}$, and Eμ-tTA MYC$^{OFF}$ mice. (FIG. 9C) Quantification of TCRαβ$^+$ and TCRγδ$^+$ T cell percentages in normal, Eμ-tTA MYC$^{ON}$, and Eμ-tTA MYC$^{OFF}$ mice. (FIG. 9D) CyTOF dot plots showing percentages of TCRαβ$^+$ and TCRγδ$^+$ T cells in one representative spleen from normal, Eμ-tTA MYC$^{ON}$, and Eμ-tTA MYC$^{OFF}$ mice. (FIG. 9E) Quantification of NK cell percentages in normal, Eμ-tTA MYC$^{ON}$, and Eμ-tTA MYC$^{OFF}$ mice. (FIG. 9F) CyTOF dot plots showing NK cell percentages in one representative spleen from normal, Eμ-tTA MYC$^{ON}$, and Eμ-tTA MYC$^{OFF}$ mice. All populations have been gated on live intact singlets. P-values were calculated using the Mann-Whitney test (ns=not significant, *p<0.05, *p<0.01, p<0.001, **p<0.0001).

FIG. 10A-10F: MYC hyperactivation in T-ALL disturbs splenic immune composition. (FIG. 10A) Quantification of CD11c+ DCs in normal (n=11), Eμ-tTA MYC$^{ON}$ (n=9), and Eμ-tTA MYC$^{OFF}$ (doxycycline 96 h, n=10) mice by CyTOF. (FIG. 10B) CyTOF dot plots showing percentages of DCs in one representative spleen from normal, Eμ-tTA MYC$^{ON}$, and Eμ-tTA MYC$^{OFF}$ mice. (FIG. 10C) Quantification of neutrophil percentages in normal, Eμ-tTA MYC$^{ON}$, and Eμ-tTA MYC$^{OFF}$ mice. (FIG. 10D) CyTOF dot plots showing percentages of neutrophils in one representative spleen from normal, Eμ-tTA MYC$^{ON}$, and Eμ-tTA MYC$^{OFF}$ mice. (FIG. 10E) Quantification of B cell percentages in normal, Eμ-tTA MYC$^{ON}$, and Eμ-tTA MYC$^{OFF}$ mice. (FIG. 10A) CyTOF dot plots showing B cell percentages in one representative spleen from normal, Eμ-tTA MYC$^{ON}$, and Eμ-tTA MYC$^{OFF}$ ice. All populations have been gated on live intact singlets. P-values were calculated using the Mann-Whitney test (ns=not significant *p<0.05, *p<0.01, *p<0.001, **p<0.0001).

FIG. 12A-12D: Phenotypes of MYC-driven malignant T-lymphocytes in primary Eμ-tTA MYC$^{ON}$ mice. Flow cytometry plots depicting the 4 common phenotypes of T cells in overt lymphoma-bearing Eμ-tTA MYC$^{ON}$ mice, namely, CD4$^+$ CD8$^+$ DP T (FIG. 12A), CD4$^+$ SP T (FIG. 12B), CD8$^+$ SP T cells (FIG. 12C), and mixed T cells (FIG. 12D).

FIG. 14A-14I: Alterations of splenic NK compositions in MYC-driven T cell lymphoma. (FIG. 14A) Representative flow cytometry plots depicting splenic T cell distributions in normal (n=4), Eµ-tTA MYC$^{ON}$ (n=6), and Eµ-tTA MYC$^{OFF}$ (doxycycline 96 h, n=6) mice. (FIG. 14B-14C) Quantification of pan CD3+ T cells (FIG. 14B), and immature DP T cell (FIG. 14C) populations in normal, Eµ-tTA MYC$^{ON}$, and Eµ-tTA MYC$^{OFF}$F spleens by flow cytometry. (FIG. 14D-14H) Representative flow cytometry plots depicting splenic NK percentages (FIGS. 14D-14F) and quantification of NK percentages (FIG. 14G-14H) in normal, Eµ-tTA MYC$^{ON}$, and Eµ-tTA MYC$^{OFF}$ mice. (FIG. 14I) Representative MFI of surface NKp46 in splenic NK cells from normal, Eµ-tTA MYC$^{ON}$, and Eµ-tTA MYC$^{OFF}$ mice. All populations are depicted as percentages of live cells (FSC+ PI−). P-values have been calculated using the Mann-Whitney test (ns=not significant, *p<0.05, **p<0.01).

FIG. 16A-16H: Suppression of circulating NK cells during MYC-driven lymphomagenesis. (FIG. 16A) Representative flow cytometry plots depicting blood T cell distributions in normal (FVB/N, n=6), Eµ-tTA MYC$^{ON}$ (n=6), and Eµ-tTA MYC$^{OFF}$ (doxycycline 96 h, n=6) mice. (FIG. 16B-16C) Quantification of percentages of circulating CD3+ T (FIG. 16B), and immature DP T (FIG. 16C) cell in blood of normal (FVB/N, n=6), Eµ-tTA MYC$^{ON}$ (n=6), and Eµ-tTA MYC$^{OFF}$ (doxycycline 96 h, n=6) mice by flow cytometry. (FIG. 16D-16E) Quantification of viable cell numbers of circulating CD3+ T (FIG. 16D), and immature DP T (FIG. 16E) cell per µl of blood in normal (FVB/N, n=6), Eµ-tTA MYC$^{ON}$ (n=6), and Eµ-tTA MYC$^{OFF}$ (doxycycline 96 h, n=6) mice by flow cytometry. (FIG. 16F-16H) Representative flow cytometry plots depicting splenic NK cell distributions (FIG. 16F) and quantification of NK cell percentages (FIG. 16G-16H) in blood of normal (FVB/N, n=6), Eµ-tTA MYC$^{ON}$ (n=6), and Eµ-tTA MYC$^{OFF}$ (doxycycline 96 h, n=6) mice. All populations are depicted as percentages of live cells (FSC+PI−). P-values have been calculated using the Mann-Whitney test (ns=not significant, *p<0.05, **p<0.01).

FIG. 17A-17I: Suppression of bone marrow NK cells during MYC-driven lymphomagenesis. (FIG. 17A) Representative CyTOF plots depicting T cell distributions in normal (n=7), Eµ-tTA MYC$^{ON}$ (n=9), and Eµ-tTA MYC$^{ON}$ (doxycycline 96 h, n=7) bone marrow. (FIG. 17B-17F) Quantification of percentages and absolute numbers of pan CD3+ T Ecells (FIG. 17B), and immature DP T cell (FIG. 17C, 17F) populations in normal, MYC$^{ON}$, and MYC$^{OFF}$ bone marrows by CyTOF. (FIG. 17D-17H) Representative plots depicting NK percentages (FIG. 17G), and quantification of NK percentages (FIG. 17H), and viable NK cell number (FIG. 17I) in bone marrows of normal, MYC$^{ON}$, and MYC mice. (FIG. 17I) Representative MFI of surface NKp46 in bone marrow NK cells from normal, MYC$^{ON}$, and MYC$^{OFF}$ mice. All populations are depicted as percentages of live intact singlets. P-values have been calculated using the Mann-Whitney test (ns=not significant, *p<0.05, p<0.01, *p<0.001, ****p<0.0001).

FIG. 20A-20B: Mutations in tTA element cause reactivation of MYC transgene in lymphomas that relapse post MYC inactivation. Genomic DNA was isolated from spleens and bone marrow of NSG transplant recipients bearing relapsed lymphomas post MYC inactivation (FIG. 3, and tTA element was cloned and sequenced.

FIG. 2I: Signaling and surface receptor changes after MYC inactivation in human BL model. Dot plots of Phospho-CyTOF depicting the global changes in surface receptors and signaling pathways after turning MYC off for 24 h in P493-6 cells.

FIG. 22A-22F: High MYC levels block transcription of STAT1 and STAT2. (a-b) Quantitative real time PCR for hSTAT1 (FIG. 22A) and, hSTAT2 (FIG. 22B) in P493-6 human BL cell line before and after MYC inactivation by doxycycline for 24 hours (n=3, mean±s.d). (FIG. 22C-22D) Quantitative real time PCR for mSTAT1 (FIG. 22C) and, mSTAT2 (FIG. 22D) in a T-lymphoma cell line derived from an Eµ-tTA/tet-O-MYC mouse before and after MYC inactivation by doxycycline for 4, 8, 24 and 48 hours (n=3, mean±s.d). P-values have been calculated using the Student's t-test (*p<0.05, p<0.01, *p<0.001). (e-f) ChIP sequencing depicting binding of MYC to STAT1 promoter in P493-6 (FIG. 22E) and Eµ-tTA MYC T-ALL (FIG. 22F) cell lines before and after MYC inactivation.

FIG. 25A-25C: JAK/STAT signatures.

FIG. 26A-26D: Type I IFN promotes NK infiltration into spleens of Eµ-tTA MYC$^{ON}$ mice with overt T cell lymphoma. (FIG. 26A) Representative flow cytometry plots comparing percentages of CD49b+ NKp46+ and NK1.1+ NKp46+NK cells between mice in IFNα-treated and vehicle (PBS)-treated groups with similar WBC counts. (FIG. 26B-26D) Quantification of percentages of DP T (FIG. 26B), CD3+ pan T (FIG. 26C), and NK cells (FIG. 26D) in IFNα-treated and vehicle (PBS)-treated Eµ-MYC$^{ON}$ overt lymphoma bearing mice.

(FIG. 27A-27B) Quantitative real time PCR for hMYC in P493-6 human BL (FIG. 27A), and Eµ-tTA MYC T-ALL (FIG. 27B) cell lines before and after combined inactivation of MYC and MEK (n=3, mean±s.d). ns=not significant.

FIG. 28A-28E: Transcriptional activation of VEGF is MYC-dependent. (FIG. 28A) Immunoblotting in MYC-driven Eµ-tTA T-lymphoma cell lines expressing empty vector (EV), MYC overexpression vector (MYC), or a transcriptionally defunct MYC mutant that fails to bind MIZ1 (MYC V394D) before (Tg-MYC$^{ON}$) and after (Tg-MYC$^{OFF}$) MYC inactivation. (FIG. 28B-28E) Quantitative real time PCR for hMYC (FIG. 28B), mSTAT1 (FIG. 28C), mSTAT2 (FIG. 28D), and mIFNa2 (FIG. 28E) in MYC-driven Eµ-tTA T-lymphoma cell lines expressing empty vector (EV), MYC overexpression vector (MYC), or a transcriptionally defunct MYC mutant that fails to bind MIZ1 (MYC V394D) before (Tg-MYC$^{ON}$) and after (Tg-MYC$^{OFF}$) MYC inactivation (n=3, mean±s.d). All p values have been calculated using student t-test. *p<0.05; *p<0.001; **p<0.0001.

FIG. 29A-29D: MYC-mediated regulation of STAT1 and STAT2 is independent of the apoptotic functions of MYC. (FIG. 29A-29D) Immunoblotting for STAT1 and STAT2 in Em-tTA MYC T lymphoma cell line before (FIG. 29A) after (FIG. 29B-29D) blocking apoptosis induced by MYC inactivation by BIM knockdown (BIM KD, FIG. 29B), BCLXL overexpression (BCLXL+++, FIG. 29C) and, combined knockdown of BIM and overexpression of BCLXL (BIM KD, BCLXL+++, FIG. 29D)

(FIG. 30A-30C) Correlation between disease burden (T-lymphoblast ratio) and ratios of total NK (FIG. 30A), resting NK (FIG. 30B) and, activated NK cells (FIG. 30C) in T-ALL patient samples (n=49, GSE62156). ns=not significant

(FIG. 32A) Comparison of overall survival probabilities of BL patients (n=34, GSE4475) stratified based on disease burden into high (B cell ratio High) and low (B cell ratio Low) categories. P-values have been calculated using the log-rank test. (FIG. 32B-32D) Correlation between disease burden (B-lymphoblast ratio) and ratios of total NK (FIG. 32B), resting NK (FIG. 32C) and, activated NK cells (FIG. 32D) in BL patient samples. ns=not significant FIG. 33A-33C: Oncogenic MYC suppresses NK cell-mediated surveillance of lymphoid malignancies. (FIG. 33A) Normal distribution of splenic immune compartments in the absence of lymphoma. (FIG. 33B) MYC-induced lymphomagenesis is associated with the modulation of cytokines and immune subsets in the tumor microenvironment. Activation of oncogenic MYC induces prolymphomagenic cytokines such as, VEGF and reduces the secretion of anti-lymphomagenic cytokines, such as Type I IFNs. The altered cytokine milieu excludes NK cells reducing immune surveillance of the lymphoma. (FIG. 33C) MYC inactivation triggers Type I IFN secretion by the lymphoma and NK-mediated immune surveillance. Hyperactivated signaling arms under each condition are depicted in bold black.

FIG. 34A-34C: Regulation of NKG2DL before and after MYC inactivation in MYCdriven lymphoma. (FIG. 34A) Representative histograms demonstrating changes in surface expression of NKG2DL ULBP1 before and after MYC inactivation in P493-6 BL cell line. (FIG. 34B) Histogram overlays comparing isotype controls (left) and surface ULBP1 (right) before and after MYC inactivation in P493-6 cells. (FIG. 34C) Quantification of MFI of ULBP1 in P493-6 before and after MYC inactivation. P values were calculated using Mann-Whitney test. ** p<0.01.

FIG. 35. Maturation of NK cells is arrested during MYC-driven lymphomagenesis. (a-b) Quantification of viable cell numbers of NK precursor cells (NKP, CD122+ NKp46−, (a)), and immature NK cells (iNK, CD122$^+$ NKp46$^-$, (b)) in normal (n=8), SRα-tTA MYC$^{ON}$ (n=8), and SRα-tTA MYC$^{OFF}$ (doxycycline 96 h, n=8) bone marrow measured by flow cytometry. (c) Comparison of proportions of numbers of NKP and iNK cells (NKP/iNK) between normal (n=8), SRα-tTA MYC$^{ON}$ (n=8), and SRα-tTA MYC$^{OFF}$ (doxycycline 96 h, n=8) bone marrow. (d) Representative flow cytometry plots depicting NK precursor cells (NKP, CD122+ NKp46-), and immature NK cells (iNK, CD122+ NKp46+) in normal (n=8), SRα-tTA MYC$^{ON}$ (n=8), and SRα-tTA MYC$^{OFF}$ (doxycycline 96 h, n=8) bone marrow. (e-f) Quantification of viable cell numbers of NK precursor cells (NKP, CD122+ NKp46−, (d)), and immature NK cells (iNK, CD122+ NKp46+, (e)) in normal (n=8), SRα-tTA MYC$^{ON}$ (n=8), and SRα-tTA MYC$^{OFF}$ (doxycycline 96 h, n=8) spleens measured by flow cytometry. (g) Comparison of proportions of numbers of NKP and iNK cells (NKP/iNK) between normal (n=8), SRα-tTA MYC$^{ON}$ (n=8), and SRα-tTA MYC$^{OFF}$ (doxycycline 96 h, n=8) spleens. (h) Representative flow cytometry plots depicting NK precursor cells (NKP, CD122+ NKp46−), and immature NK cells (iNK, CD122+ NKp46+) in normal (n=8), SRα-tTA MYC$^{ON}$ (n=8), and SRα-tTA MYC$^{OFF}$ (doxycycline 96 h, n=8) bone marrow. (i) Model depicting the arrest in differentiation from NK precursor (NKP) stage to immature NK (iNK) stage during MYC-driven lymphomagenesis. Arrested step in NK cell differentiation is indicated by a red cross. Dashed arrows indicate stages of NK cell differentiation that do not occur because of the arrest. All p values have been calculated using Mann-Whitney test. P-values: ns=not significant; *p<0.05; p<0.01;*p<0.001.

DETAILED DESCRIPTION OF THE INVENTION

Figure 1A:
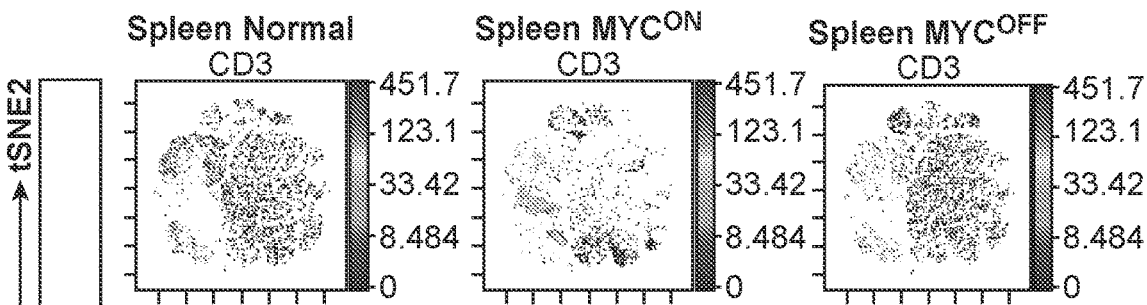
FIG. 1A-1K: MYC overexpression in T cell lymphoma disturbs splenic NK composition.
Figure 1B:
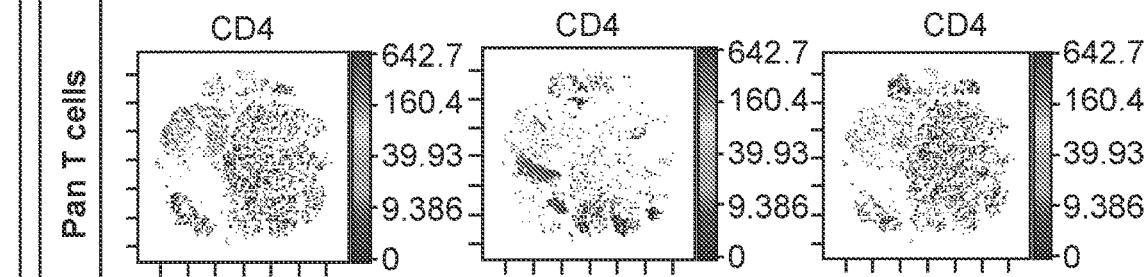
Figure 1C:
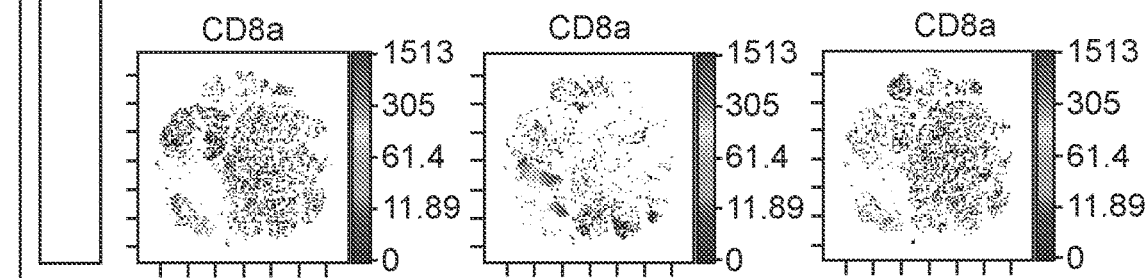

Compositions and methods are provided for the treatment of cancer with NK cells. Cancers may be diagnosed for aberrant patterns of NK cell distribution, which patterns are indicative of a MYC-driven cancer. Such cancers are treated with NK cells engineered to express high levels of cytotoxicity marker NKp46, alone or in combination with a Type I interferon.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

Natural killer (NK) cells are a type of cytotoxic lymphocyte that constitute a major component of the innate immune system. NK cells play a major role in the rejection of tumors and cells infected by viruses. They usually express the surface markers CD16 (FcγRIII) and CD56 in humans. Given their strong cytolytic activity and the potential for auto-reactivity, NK cell activity is tightly regulated. For example, NK cells must receive an activating signal, which can come in a variety of forms, e.g. interferons or macrophage-derived cytokines. Cytokines involved in NK activation include IL-12, IL-15, IL-18, IL-2, and CCL5.

NK cells recognize infected or transformed cells through multiple cell surface receptors including NKG2D, CD16, and natural cytotoxicity receptors (NCRs) such as NKp44, NKp46, and NKp30. These receptors activate signaling adapter proteins such as DAP10, DAP12, and CD34, which contain immuno-tyrosine activation motifs (ITAMs) that initiate the release of cytolytic granules containing perforin and granzymes, as well as mediate production and release of cytokines and chemokines such as IFN-γ and TNF-α.

Importantly, NK cell-mediated cytotoxicity does not rely on the presentation of self HLA. Therefore, NK cells hold significant clinical interest as a cell-based therapy for cancer because of their ability to be used in an allogeneic setting and provide an off-the-shelf cellular product. Clinical trials of adoptively transferred allogeneic NK cells demonstrate these cells can survive in patients for several weeks to months.

NK cells may be isolated by negative or positive selection using methods and reagents known in the art. For example negative selection may utilize commercially available antibodies that bind to NK1.1, CD3, CD4, CD19, CD66b, glycophorin, NKG2D, NKp46, etc. Alternatively NK cells may be positively selected for expression of CD56, and/or CD16.

Expression of NKp46 is of particular interest. NKp46 is expressed on all NK cell subsets. NKp46 is a 46 kDa type 1 transmembrane glycoprotein characterized by a 30 aa intracellular tail, 20 aa transmembrane domain, and two extracellular Ig-like domains that are contacted through a 25 aa short peptide. The transmembrane domain contains an Arg residue that can bind the signal adapter proteins FcεRI and CD3ζ. The membrane-proximal domain (D2) was identified as the ligand-binding domain of NKp46 receptor. Target cell-expressed heparan sulfate (HS) can bind with NKp46 and other NK receptors and serves as an accessory molecule for the recognition of cellular ligand(s) by NKp46. NKp46 is also unique because it is specifically expressed on NK cells and not on other immune subsets with cytotoxic capabilities such as, CD8+ T cells.

In some embodiments the NK cells are autologous. In some embodiments the cells are allogeneic, for example see Hermanson et al. (2016), Induced Pluripotent Stem Cell-Derived Natural Killer Cells for Treatment of Ovarian Cancer. Stem Cells, 34: 93-101; Chabannon et al. (2016) Manufacturing Natural Killer Cells as Medicinal Products. Frontiers in Immunology. 7:504; Suck et al. (2016) NK-92: an 'off-the-shelf therapeutic' for adoptive natural killer cell-based cancer immunotherapy, Cancer Immunology, Immunotherapy 65(4):485-492, Yang et al. (2016) Phase I Study of Random Healthy Donor-Derived Allogeneic Natural Killer Cell Therapy in Patients with Malignant Lymphoma or Advanced Solid Tumors, Cancer Immunol Res; 4(3); 215-24; Redner et al. (2017) Phase 1 clinical trial of adoptive immunotherapy using "off-the-shelf" activated natural killer cells in patients with refractory and relapsed acute myeloid leukemia, Cytotherapy 19(10):1225-1232; each herein specifically incorporated by reference.

NK cells collected from a subject may be separated from a mixture of cells by techniques that enrich for desired cells, or may be engineered and cultured without separation. An appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Techniques for affinity separation may include magnetic separation, using antibody-coated magnetic beads such as Magnetic Activated Cell Sorting (MACS) from Miltenyi Biotech, affinity chromatography, cytotoxic agents joined to a monoclonal antibody or used in conjunction with a monoclonal antibody, e.g., complement and cytotoxins, and "panning" with antibody attached to a solid matrix, e.g., a plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g., propidium iodide). Any technique may be employed which is not unduly detrimental to the viability of the selected cells. The affinity reagents may be specific receptors or ligands for the cell surface molecules indicated above. In addition to antibody reagents, peptide-MHC antigen and T cell receptor pairs may be used; peptide ligands and receptor effector and receptor molecules, and the like.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum (FCS).

The collected and optionally enriched cell population may be used immediately for genetic modification, or may be frozen at liquid nitrogen temperatures and stored, being thawed and capable of being reused. The cells will usually be stored in 10% DMSO, 50% FCS, 40% RPMI 1640 medium. The cells may also be cultured in vivo, e.g. in the presence of cytokines such as Type 1 interferon, IL-2, IL-12, and/or IL-15.

The cells may be infused to the subject in any physiologically acceptable medium by any convenient route of administration, normally intravascularly, although they may also be introduced by other routes, where the cells may find an appropriate site for growth. Usually, at least $1\times100$ cells/kg will be administered, at least $1\times10^7$ cells/kg, at least $1\times10^8$ cells/kg, at least $1\times10^9$ cells/kg, at least $1\times10^{10}$ cells/kg, or more, usually being limited by the number of NK cells that are obtained during collection.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

As used herein, a "therapeutically effective amount" refers to that amount of the therapeutic agent, e.g. an infusion of NK cells and optionally exogenous interferon, sufficient to treat or manage a disease or disorder. A therapeutically effective amount may refer to the amount of therapeutic agent sufficient to delay or minimize the onset of disease, e.g., to delay or minimize the spread of cancer, or the amount effective to decrease or increase signaling from a receptor of interest. A therapeutically effective amount may also refer to the amount of the therapeutic agent that provides a therapeutic benefit in the treatment or management of a disease. Further, a therapeutically effective amount with respect to a therapeutic agent of the invention means the amount of therapeutic agent alone, or in combination with other therapies, that provides a therapeutic benefit in the treatment or management of a disease.

Type I IFN.

The human type I IFN family consists of multiple IFNα members, single IFNβ, epsilon, kappa, and omega subtypes. These cytokines induce antiviral responses by binding a common receptor, the IFNAR1/IFNAR2, expressed on a wide variety of cell types. IFNα proteins are produced by leukocytes. They are mainly involved in innate immune response against viral infection. The genes responsible for their synthesis come in 13 subtypes that are called IFNA1, IFNA2, IFNA4, IFNA5, IFNA6, IFNA7, IFNA8, IFNA10, IFNA13, IFNA14, IFNA16, IFNA17, IFNA21. These genes are found together in a duster on chromosome 9. IFN-s proteins are produced in large quantities by fibroblasts. They have antiviral activity that is involved mainly in innate immune response. Two types of IFN-β have been described, IFN-β1 (IFNB1) and IFN-β3 (IFNB3). IFNε, κ, ω appear to come in a single isoform in humans. IFN-ω is released by leukocytes at the site of viral infection or tumors. It is shown herein that inactivation of MYC in lymphomas can trigger the production of Type I IFNs from the tumor cells themselves.

The type I interferon (IFN) receptor (IFNAR) is comprised, as other cytokine receptors, of two components, designated IFNAR1 and IFNAR2. It is unique among cytokine receptors in the number of cognate ligands. The type I IFN receptors are distinct from those required for the type II IFNγ (IFNGR1 and IFNGR2) and type III IFNs (IFNλR and IL10Rβ). Most cell types bind IFNs, with large variation in the number of binding sites (200-10,000/cell) and binding affinities. Various type I IFNs bind to IFNAR2 with Kd values mostly in the nM range (from 0.1 to 1000 nM) and bind to IFNAR1 with Kd mostly in the µM range (from 0.05 to 10 µM). The type I IFN receptor, typical of class II hCR, lack intrinsic kinase activity and thus rely on associated Janus kinases (JAKs) to phosphorylate receptors and signal transducing molecules, such as STAT proteins, after ligand-induced receptor clustering. IFNAR1 is preassociated with Tyk2, which also stabilizes IFNAR1 cell surface expression levels.

Human interferon alpha (hIFNα), particularly hIFN-2a (Roferon-A, Hoffmann-La Roche) and hIFN-2b (Intron A, Schering-Plough) are clinically used in hepatitis and cancer treatments. The antiproliferative activity occurs through cancer cell growth inhibition by cell cycle arrest, apoptosis, or differentiation. Indirect activity occurs through activation of immune cells such as T cells and natural killer cells, inhibition of vascularization (anti-angiogenesis), and induction of cytokines. Current oncology indications include hairy cell leukemia, melanoma, follicular lymphoma, renal cell carcinoma, AIDS-related Kaposi's sarcoma, and chronic myelogenous leukemia.

In some embodiments, IFN-α is administered to a patient, alone or in combination with an effective dose of NK cells. The IFN can be administered at a dose similar to, or lower than conventional dosing, including without limitation, wherein hIFN-2a or hIFN-2b is administered at a dose of from about $0.5 \times 10^6$ IU/m$^2$, up to about $50 \times 10^6$ IU/m$^2$; where the dose may be at least about $10^6$ IU/m$^2$, at least about $2 \times 10^6$ IU/m$^2$, at least about $3 \times 10^6$ IU/m$^2$, at least about $5 \times 10^6$ IU/m$^2$, and not more than about $30 \times 10^6$ IU/m$^2$, not more than about $20 \times 10^6$ IU/m$^2$, not more than about $10 \times 10^6$ IU/m$^2$, delivered intramuscular, intravenous, subcutaneous, and intraperitoneal routes, daily, 2 times weekly, 3 times weekly, weekly, etc. A low dose may be from around about $0.5 \times 10^6$ IU/m$^2$, up to about $5 \times 10^6$ IU/m$^2$.

Type 1 Interferon may be administered in combination with NK cells. "In combination with", "combination therapy" and "combination products" refer, in certain embodiments, to the concurrent administration to a patient of an interferon and cells described herein. When administered in combination, each component, i.e. cell or protein, can be administered at the same time or sequentially in any order at different points in time. Thus, each component can be administered separately but sufficiently closely in time so as to provide the desired therapeutic effect. Alternatively, the NK cells may be combined with the interferon for a period of time prior to administration, e.g. for about 1 hour, about 4 hours, about 1 day, about 2 days, about 3 days, about 1 week, or more.

"Concomitant administration" means administration of one or more components, such as engineered proteins and cells, known therapeutic agents, etc. at such time that the combination will have a therapeutic effect. Such concomitant administration may involve concurrent (i.e. at the same time), prior, or subsequent administration of components. A person of ordinary skill in the art would have no difficulty determining the appropriate timing, sequence and dosages of administration.

The use of the term "in combination" does not restrict the order in which agents are administered to a subject with a disorder. A first agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent or cells to a subject with a disorder. For example, a dose of exogenous Type 1 IFN is optionally administered in combination with a population of NK cells.

MYC is a master transcription factor that can regulate the expression of up to 15% of genes in the genome. Overexpression of MYC is thought to contribute to the pathogenesis of over 50% of human cancers. Experimentally, the inhibition of MYC reverses tumorigenesis in transgenic mouse models. Therapeutically targeting MYC would have broad clinical impact across multiple cancer types. However, identifying small molecules that directly target MYC has been extremely challenging.

The gene encoding MYC, refseq NG_007161 on chromosome 8, encodes the proto-oncogene, which is a nuclear phosphoprotein that plays a role in cell cycle progression, apoptosis and cellular transformation. The encoded protein forms a heterodimer with the related transcription factor MAX. This complex binds to the E box DNA consensus sequence and regulates the transcription of specific target genes. Amplification of this gene is frequently observed in numerous human cancers. Translocations involving this gene are associated with Burkitt lymphoma and multiple myeloma in human patients. There is evidence to show that translation initiates both from an upstream, in-frame non-AUG (CUG) and a downstream AUG start site, resulting in the production of two isoforms with distinct N-termini. See, for example, NP_001341799 for the protein sequence; and Hann et al. (1988) Cell 52 (2), 185-195.

The MYC oncogene drives the pathogenesis of many hematopoietic malignancies, including Burkitt's lymphoma (BL), Diffuse large B cell lymphoma (DLBCL) and Acute Lymphoblastic Leukemia (ALL). These malignancies are often "oncogene-addicted" to MYC. Treating subjects having cancers that are specifically identified as MYC-addicted with new therapeutic modalities circumvents the issues associated with the undruggability of MYC.

As shown herein, cancer cells suspected of being associated with MYC can be assessed for over-expression of MYC, for MYC translocations, for suppression of STAT1 and STAT2 expression; and the like. Global signaling changes can be assessed with phosphor-CyTOF for phosphorylation changes to MAPK, pERK1/2, pP38, pLCγ2, etc. as shown in the Examples. Changes indicative of MYC-driven tumorigenesis, such as increased levels of MYC and decreased expression of STAT1 and STAT2, are used to classify a cancer as potentially responsive to adoptive NK cell transfer and treatment with Type 1 interferon. Alternatively, common gene Myc core signatures have been identified in the art and can be used in cancer classification.

Signal transducer and activator of transcription 1 (STAT1) and STAT2 are transcription factors which in humans are encoded by the STAT1 and STAT2 genes. All STAT molecules are phosphorylated by receptor associated kinases, that causes activation, dimerization by forming homo- or heterodimers and finally translocate to nucleus to work as transcription factors. Specifically STAT1 can be activated by several ligands such as Interferon alpha (IFNα), Interferon gamma (IFNg), Epidermal Growth Factor (EGF), Platelet Derived Growth Factor (PDGF) or Interleukin 6 (IL-6).

Type I interferons activate signaling pathways that lead to phosphorylation and activation of the Jak kinases TYK2 and JAK and also STAT1 and STAT2. STAT molecules form dimers and bind to ISGF3G/IRF-9, which is Interferon stimulated gene factor 3 complex with Interferon regulatory Factor 9. This allows STAT1 to enter the nucleus. STAT1 has a key role in many gene expressions that cause survival of the cell, viability or pathogen response. In response to either IFN-α or IFN-β stimulation, STAT1 forms a heterodimer with STAT2 that can bind the ISRE (Interferon-Stimulated Response Element) promoter element. Binding of the promoter element leads to an increased expression of ISG (Interferon-Stimulated Genes).

As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

As used herein, the terms "cancer" (or "cancerous"), or "tumor" are used to refer to cells having the capacity for autonomous growth (e.g., an abnormal state or condition characterized by rapidly proliferating cell growth). Hyperproliferative and neoplastic disease states may be categorized as pathologic (e.g., characterizing or constituting a disease state), or they may be categorized as non-pathologic (e.g., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. Pathologic hyperproliferative cells occur in disease states characterized by malignant tumor growth. Examples of non-pathologic hyperproliferative cells include proliferation of cells associated with wound repair. The terms "cancer" or "tumor" are also used to refer to malignancies of the various organ systems, including those affecting the lung, breast, thyroid, lymph glands, blood and lymphoid tissue, gastrointestinal organs, and the genitourinary tract, as well as to adenocarcinomas which are generally considered to include malignancies such as most colon cancers, renal-cell carcinoma, prostate cancer and/or testicular tumors, non-small cell carcinoma of the lung, cancer of the small intestine and cancer of the esophagus.

Exemplary cancer types include but are not limited to hematologic cancers, adrenal cortical cancer, anal cancer, aplastic anemia, bile duct cancer, bladder cancer, bone cancer, bone metastasis, brain cancers, central nervous system (CNS) cancers, peripheral nervous system (PNS) cancers, breast cancer, cervical cancer, childhood Non-Hodgkin's lymphoma, colon and rectal cancer, endometrial cancer, esophagus cancer, Ewing's family of tumors (e.g., Ewing's sarcoma), eye cancer, gallbladder cancer, gastrointestinal carcinoid tumors, gastrointestinal stromal tumors, gestational trophoblastic disease, Hodgkin's lymphoma, Kaposi's sarcoma, kidney cancer, laryngeal and hypopharyngeal cancer, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcomas, melanoma skin cancer, non-melanoma skin cancers, stomach cancer, testicular cancer, thymus cancer, thyroid cancer, uterine cancer (e.g. uterine sarcoma), transitional cell carcinoma, vaginal cancer, vulvar cancer, mesothelioma, squamous cell or epidermoid carcinoma, bronchial adenoma, choriocarinoma, head and neck cancers, teratocarcinoma, or Waldenstrom's macroglobulinemia. For example, MYC has been shown to drive tumorigenesis in, for example, lymphoma, leukemia, osteosarcoma, hepatocellular carcinoma, squamous carcinoma, and pancreatic carcinoma.

Hematologic cancers include lymphomas, e.g. Non-Hodgkin lymphomas (NHL); and leukemias, and multiple myelomas. NHL are a heterogeneous group of disorders involving malignant monoclonal proliferation of lymphoid cells in lymphoreticular sites, including lymph nodes, bone marrow, the spleen, the liver, and the GI tract. Presenting symptoms usually include peripheral lymphadenopathy. Compared with Hodgkin lymphoma, there is a greater likelihood of disseminated disease at the time of diagnosis. Diagnosis is usually based on lymph node or bone marrow biopsy or both. Conventional treatment involves radiation therapy, chemotherapy, or both.

Most (80 to 85%) NHLs arise from B cells; the remainder arise from T cells or natural killer cells. Either precursor or mature cells may be involved. Overlap exists between leukemia and NHL because both involve proliferation of lymphocytes or their precursors. A leukemia-like picture with peripheral lymphocytosis and bone marrow involvement may be present in up to 50% of children and in about 20% of adults with some types of NHL. A prominent leukemic phase is less common in aggressive lymphomas, except Burkitt's and lymphoblastic lymphomas.

Specific diseases include, without limitation, precursor B-lymphoblastic leukemia/lymphoma; B-cell chronic lymphocytic leukemia/small lymphocytic lymphoma; B-cell prolymphocytic leukemia; lymphoplasmacytic lymphoma; splenic marginal zone B-cell lymphoma (±villous lymphocytes); hairy cell leukemia; plasma cell myeloma/plasmacytomas; extranodal marginal zone B-cell lymphoma of the MALT type; nodal marginal zone B-cell lymphoma (monocytoid B cells); follicular lymphoma; mantle cell lymphoma; diffuse large B-cell lymphomas (including mediastinal large B-cell lymphoma and primary effusion lymphoma); and Burkitt's lymphoma, and particularly DLCBCL.

Acute leukemias are rapidly progressing leukemia characterized by replacement of normal bone marrow by blast cells of a clone arising from malignant transformation of a hematopoietic cell. The acute leukemias include acute lymphoblastic leukemia (ALL) and acute myelogenous leukemia (AML). ALL often involves the CNS, whereas acute monoblastic leukemia involves the gums, and AML involves localized collections in any site (granulocytic sarcomas or chloromas).

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom (s) but has not yet been diagnosed as having it; (b) inhibiting the disease and/or symptom(s), i.e., arresting development of a disease and/or the associated symptoms; or (c) relieving the disease and the associated symptom(s), i.e., causing regression of the disease and/or symptom(s). Those in need of treatment can include those already inflicted (e.g., those with cancer, e.g. those having tumors) as well as those in which prevention is desired (e.g., those with increased susceptibility to cancer; those with cancer; those suspected of having cancer; etc.).

"Diagnosis" as used herein generally includes determination of a subject's susceptibility to a disease or disorder, determination as to whether a subject is presently affected by a disease or disorder, prognosis of a subject affected by a disease or disorder (e.g., classification according to effects of MYC signaling on NK cell levels and activation, responsiveness of cancer to therapy), and use of therametrics (e.g., monitoring a subject's condition to provide information as to the effect or efficacy of therapy).

"Predicting," as used herein, refers to the process of establishing that a specific event will, or is likely to, occur, or an outcome will be, or is likely to be, achieved, prior to the event or outcome taking place. In some cases, where the prediction is related to a patient's response to therapy, predicting the outcome of therapy may include establishing that the patient will respond in one way if the patient satisfies a set of patient-specific conditions, or that the patient will respond in another way if the patient does not satisfy at least some conditions in the set of patient-specific conditions. In some cases, predicting an outcome to therapy is done before the therapy is administered to the patient.

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples. A hematopoietic sample may comprise any biological sample in which a population of hematopoietic cells are present, for example including blood samples, spleen, lymph node, bone marrow, and the like, where blood samples provide a convenient source of cells.

The term "normal" as used in the context of "normal cell," is meant to refer to a cell of an untransformed phenotype or exhibiting a morphology of a non-transformed cell of the tissue type being examined. The terms "control", "control reaction", "control assay", and the like, refer to a reaction, test, or other portion of an experimental or diagnostic procedure or experimental design for which an expected result is known with high certainty, e.g., in order to indicate whether the results obtained from associated experimental samples are reliable, indicate to what degree of confidence associated experimental results indicate a true result, and/or to allow for the calibration of experimental results. For example, in some instances, a control may be a "negative control" such that an essential component of the assay is excluded from the negative control reaction such that an experimenter may have high certainty that the negative control reaction will not produce a positive result. In some instances, a control may be "positive control" such that all components of a particular assay are characterized and known, when combined, to produce a particular result in the assay being performed such that an experimenter may have high certainty that the positive control reaction will not produce a negative result.

Method of Classifying Cancers

In the present method, a clinical response of a cancer to NK cell based immunotherapy, e.g., one or both of NK cell administration and administration of Type 1 interferon, is predicted using a model that evaluates one or more patient-specific parameters of the cancer, including parameters related to the makeup of immune cell subtypes in a patient sample, and the status of MYC pathway activation in a patient sample. The specific input parameters to the model may include a reduced proportion of activated NK cells among a plurality of lymphocytes, e.g., among the overall lymphocyte population in a patient sample; reduced levels of αIFN in the sample; and upregulation of MYC activity levels with concomitant down-regulation of signaling pathways that can activate immune surveillance, including suppression of STAT1, STAT2 and Type I IFN expression. It is predicted that the patient will exhibit a clinically beneficial response to administration of one or both of NK cells and Type 1 interferon based on the evaluation that the patient's parameter values satisfy predetermined criteria for activation of MYC and subsequent suppression of Type 1 interferon synthesis and NK cell activation. In some embodiments, if the patient's parameter values does not satisfy the corresponding predetermined criteria in the evaluation, it is predicted that the patient will not exhibit a clinically beneficial response to the immunotherapy. A patient predicted to respond to immunotherapy may be treated with one or both of NK cell administration and administration of Type 1 interferon. Optionally an inhibitor of MYC is administered in combination.

The patient-specific parameter used in the present method may include the makeup of immune cell subtypes in a hematopoietic sample from the patient, i.e. a reduced proportion of activated NK cells. Immune cell subtypes of interest may be distinguished using any method, as described herein, e.g., flow cytometry, sequence analysis, etc. In certain embodiments, the lymphocyte subtypes are classified based on the types of cell surface receptors expressed by a lymphocyte, e.g., using flow cytometry or mass cytometry. In some embodiments, the lymphocyte subtypes are classified based on the gene expression profile (GEP) of the sample and deconvoluting the GEP using a computational algorithm that enables identification of the different lymphocyte subtypes in the sample, e.g., using CIBERSORT, as described in Newman et al., Nat Methods. 201512:453, which is incorporated herein by reference.

In certain embodiments, the makeup of immune cell subtypes is the proportion or absolute number of NK cells; or the proportion or absolute number of mature and activated NK cells among the overall lymphocyte population. Thus, the proportion may be a ratio between an estimate of the amount of biological material, e.g., individual cells or mRNA, attributable to NK cells, or activated NK cells. and the total amount of individual cells or mRNA, attributable to any immune cell in the sample. The decrease of activated mature NK cells among the overall lymphocyte population in a sample may vary depending on the patient, and may be in the range at least about 10%, at least about 25%, at least about 50% or more, relative to a control, normal population.

The proportion of activated NK cells among the overall immune cell population may be positively correlated with a patient's clinical response to adoptive NK cell and/or Type 1 interferon therapy. Thus, a patient that is predicted to exhibit a clinically beneficial response to such therapy will have a decrease in the number of activated NK cells that is equal to or higher than a threshold proportion.

The predetermined criteria may include a predetermined threshold value set based on levels of mature NK cells in healthy individuals. In some embodiments, the threshold value is chosen based on an analysis of tumor samples from a reference population of patients, wherein the patients are diagnosed with MYC-driven cancers, particularly MYC-driven hematopoietic cancers.

The patient-specific immunobiology analysis may be obtained by analyzing a sample of immune cells obtained from the patient. Samples can be obtained from the tissues or fluids of an individual. For example, samples can be obtained from whole blood, lymph or bone marrow biopsy, etc. The samples are collected any time after an individual is suspected of or diagnosed to have a MYC-driven cancer or has exhibited symptoms diagnostic of such a disease.

As the present method for classifying a patient is a predictive method, the sample from the patient who is to be classified according to the present method may be obtained before the patient starts therapy, e.g., before administration of NK cells or interferon.

Alternatively, analyzing a tumor sample may be performed to determine the status of MYC pathway genes and proteins. The tumor sample may be analyzed histologically using any suitable histology stain and/or immunohistochemical methods. The sample may be dissociated, e.g., using a protease such as trypsin, and individual cells of the sample may be analyzed, e.g., using flow cytometry or mass cytometry. Methods of preparing a sample of cells for flow cytometry analysis is described in, e.g., books such as Carey et al (*Flow Cytometry in Clinical Diagnosis*, 4⁺ Edition ASCP Press, 2007), Ormerod (*Flow Cytometry—A practical approach* 3rd Edition. Oxford University Press, Oxford, U K 2000), Ormerod (*Flow Cytometry* 2nd Edition. BIOS Scientific Publishers, Oxford, U K 1999) and Ormerod (*Flow Cytometry—A basic introduction* 2009 Cytometry Part A 75A, 2009), each of which are incorporated by reference herein.

Analysis may be performed, for example, by determining the expression or activity of MYC in cancer cells. Determining the presence of MYC translocations may also be performed. Where MYC is upregulated, the level of protein or level of protein activity may be at least about 10% greater than the level in a comparable normal cell population, at least about 20% higher, at least about 50% higher or more. As shown herein, upregulation of MYC leads to down-regulation of STAT1 and/or STAT2 expression, for example a decrease in phosphorylation or a decrease in protein levels of up to about 10% of the level in a comparable normal cell population, up to about 20%, up to about 50%, or more. There is also a decrease in Type I interferon, e.g. IFNα or IFNβ resulting from the MYC activity.

The clinical response to an immunotherapy may include any suitable measure of clinical outcome/endpoint in response to immunotherapy. In some embodiments, the clinical outcome is measured by progression-free survival (PFS), time to progression (TTP), time to subsequent therapy, response rate (complete or partial response), overall survival, disease free survival, and/or an immunological response to the immunotherapy. Suitable clinical outcomes/endpoints are described in, e.g., Johnson et al. (2003) J. Clin. Oncol. 21(7):1404; U.S. Food and Drug Administration guidance titled "Clinical Trial Endpoints for the Approval of Cancer Drugs and Biologics", published May 2007 (UCM071590.pdf); and Cheson et al., J Clin Oncol. 2007.25:579, which are incorporated herein by reference. Progression of disease may be measured by any convenient method, including measuring the size of a tumor using positron emission tomography (PET) or computed tomography (CT) scan, magnetic resonance imaging (MRI), etc., lymph node biopsy, and bone marrow evaluation, as summarized in, e.g., Cheson et al., J Clin Oncol. 1999. 17:1244, which is incorporated herein by reference.

In some embodiments, the clinically beneficial response of a patient who receives an immunotherapy may be a clinical outcome that is better than the clinical outcome of a patient who does not receive the therapy. Thus, in some embodiments, the clinically beneficial response of a patient who receives the immunotherapy may be a progression-free survival of the treated patient that is longer than the progression-free survival of a patient who does not receive the therapy. Progression may be local progression, regional progression, locoregional progression, or metastatic progression. The clinically beneficial response may be a progression-free survival for the treated patient that is longer by 6 months or more, e.g., 9 months or more, 12 months or more, 24 months or more, 36 months or more, or 48 months or more, than the progression-free survival for the untreated patient. The clinically beneficial response may be a progression-free survival for the treated patient that is longer by a range of 6 months to 10 years, e.g., 9 months to 5 years, or 1 to 4 years, compared to the progression-free survival for the untreated patient.

Methods of Treatment

Compositions and methods are provided for treatment of cancer by administration of a composition of an effective dose of one or both of natural killer cells and a type 1 interferon. In some embodiments the NK cells are contacted with the interferon prior to administration. In some embodiments the NK cells, which may be activated prior to administration, are administered in combination with the type 1 interferon. In some embodiments the interferon is human IFNα. Cancers are optionally classified prior to treatment to determine the presence of myc-driven cancer cells and probability of responding to the interferon and NK cell therapy, where the presence of MYC-driven cancer is indicative that the individual is suited for treatment by the methods of the invention.

NK cells are delivered to the tumor site, e.g. by localized injection at the site of cancer or in close proximity to the site of cancer, although systemic administration may find use, e.g. when the cancer is metastatic, for leukemias, for lymphomas, etc. In some embodiments the NK cells are autologous. In other embodiments the NK cells are allogeneic. Repeated administration of NK cells to lyse cancer cells may be required. The effective dose of NK cells may be at least about $10^5$ cells, at least about $10^6$ cells, at least about $10^7$ cells, or more.

Generally the NK cells for use in the methods of the invention have been selected, e.g. by positive or negative selection, from an appropriate cell source, e.g. peripheral blood monocytes (PBMC), etc. Methods and markers for the enrichment of NK cells are known in the art. The NK cells may be selected for expression of NKp46. After isolation from the host or a donor, the NK cells may be activated, e.g. with an effective dose of IL-2, e.g. at least about 10 units/ml, at least about 100 units/ml, at least about 1000 units/ml or more, which increases the cytotoxic function of NK cells and expands the numbers of NK cells. Cells may also be cultured with one or both of IL12 and interferon alpha, optionally combined with the IL-2. Cells may be cultured with cytokines for a period of time sufficient for activation, e.g. at least about 12 hours, at least about 24 hours, at least about 48 hours and not more than about 4 days, usually not more than about 3 days. Prior to use the NK cells may be typically washed free of excess cytokines. The cells are typically resuspended in an pharmaceutically acceptable excipient, and injected into the patient at an intra-tumoral or systemic site, e.g. i.v., sub-cutaneous, intramuscular, etc.

The methods of the invention may be combined with therapy designed to eliminate the cancer cells present in a tumor, e.g. in a combination therapy with Type I interferon, or various other conventional methods of treating cancer cells, for example chemotherapy, radiation therapy, etc. Chemotherapeutic agents may include, for example, cyclophosphamide, vincristine, doxorubicin, methotrexate, ifosfamide, etoposide, and cytarabine (CODOX-M/IVAC) plus rituximab; rituximab plus etoposide, prednisone, vincristine (Oncovin), and doxorubicin (R-EPOCH) and rituximab plus cyclophosphamide, vincristine, doxorubicin (Adriamycin), and dexamethasone (R-Hyper CVAD). Typically chemotherapeutic drugs will not be administered in a manner that causes lymphocytotoxicity and loss of the NK cells that are administered. An effective amount of such agents can readily be determined by routine experimentation, as can the most effective and convenient route of administration and the most appropriate formulation. Various formulations and drug delivery systems are available in the art. (See, e.g., Remington's Pharmaceutical Sciences, supra.)

Suitable routes of administration may, for example, include oral, rectal, transmucosal, transdermal, nasal, or intestinal administration and parenteral delivery, including intramuscular, subcutaneous, intramedullary injections, as well as intrathecal, direct intraventricular, intravenous, intraperitoneal, intranasal, or intraocular injections. The agent or composition thereof may be administered in a local rather than a systemic manner. For example, a suitable agent can be delivered via injection or in a targeted drug delivery system, such as a depot or sustained release formulation.

The pharmaceutical compositions may be manufactured by any of the methods well-known in the art, such as by conventional mixing, dissolving, granulating, dragee-making, levigating, emulsifying, encapsulating, entrapping, or lyophilizing processes. The compositions can include one or more physiologically acceptable carriers such as excipients and auxiliaries that facilitate processing of active molecules into preparations for pharmaceutical use. Proper formulation is dependent upon the route of administration chosen.

For example, for injection, a cell composition may be formulated in aqueous solutions, preferably in physiologically compatible buffers such as Hanks's solution, Ringer's solution, or physiological saline buffer.

Compositions formulated for parenteral administration by injection, e.g., by bolus injection or continuous infusion can be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Formulations for parenteral administration include aqueous solutions of the compound or agent to be administered, including in water-soluble form.

Suspensions of the active agents may also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the agents to allow for the preparation of highly concentrated solutions. Alternatively, the active ingredient may be in powder form for constitution with a suitable vehicle, e.g., sterile pyrogen-free water, before use.

For any composition employed herein, a therapeutically effective dose can be estimated initially using a variety of techniques well-known in the art. For example, in a cell culture assay, a dose can be formulated in animal models to achieve a circulating concentration range that includes the $IC_{50}$ as determined in cell culture. Dosage ranges appropriate for human subjects can be determined, using data obtained from cell culture assays and other animal studies.

A therapeutically effective dose of an agent refers to that amount of the agent that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods known in the art, in view of the specifics of a subject's condition.

The MEC will vary but can be estimated from, for example, in vitro data, such as the concentration necessary to achieve 50-90% inhibition of activity using the assays described herein. Dosages necessary to achieve the MEC will depend on individual characteristics and route of administration. Agents or compositions thereof should be administered using a regimen which maintains plasma levels above the MEC for about 10-90% of the duration of treatment, preferably about 30-90% of the duration of treatment, and most preferably between 50-90%. In cases of local administration or selective uptake, the effective local concentration of the drug may not be related to plasma concentration.

The amount of agent or composition administered will, of course, be dependent on a variety of factors, including the sex, age, and weight of the subject being treated, the severity of the affliction, the manner of administration, and the judgment of the prescribing physician.

The present compositions may, if desired, be presented in kit, such as a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a agent of the invention formulated in a compatible pharmaceutical carrier may also be prepared, placed in an appropriate container, and labeled for treatment of an indicated condition. Suitable conditions indicated on the label may include treatment of disorders or diseases.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

MYC Functions as a Master Switch for Natural Killer Cell-Mediated Immune Surveillance of Lymphoid Malignancies The MYC oncogene drives the pathogenesis of many hematopoietic malignancies, including Burkitt's lymphoma (BL) and Acute Lymphoblastic Leukemia (ALL). These malignancies are often "oncogene-addicted" to MYC. Using CyTOF, flow cytometry, and CIBERSORT we demonstrate a systemic reduction in numbers and activation of natural killer (NK) cells in Eµ-tTA/Tet-O-MYC mice predisposed to developing MYC-driven T cell lymphomas. MYC inhibition clears malignant T-lymphocytes and restores normal NK composition of lymphoid organs including the spleen, blood and bone marrow. We observe that NK cells present a barrier to the systemic engraftment of T cell lymphomas. Moreover, adoptively transferred NK cells alone significantly prolong regression of lymphoma after MYC inactivation in lymphoma bearing immune deficient mice. We identified that MYC overexpression in both murine and human T-lymphoma cells represses STAT1 and STAT2, and subsequent of secretion of Type I IFNs required for splenic NK homeostasis. Even brief treatment with Type I interferon restored recruitment and activation of NK cells in lymphoma-bearing Eµ-tTA/Tet-O-MYC mice. In humans with BL, MYC expression and associated STAT1 and STAT2 expression was associated with a significantly favorable clinical outcome. Hence, MYC causally and reversibly suppress NK-mediated immune surveillance during lymphomagenesis. Our study provides methods for the use of NK cell-based therapies to treat MYC-driven lymphomas.

We hypothesized that oncogenic MYC may directly perturb the global immune composition and architecture at sites of lymphomagenesis, to evade immune surveillance. To address this, we have used mass cytometry (CyTOF) and CIBERSORT to examine specific changes in the host immune composition both upon MYC activation and after MYC inactivation in transgenic mice predisposed to developing MYC-driven T cell lymphoblastic lymphoma. We found that MYC activation during lymphomagenesis specifically results in marked suppression of the activated natural killer (NK) subset from the tumor microenvironment and have identified a direct mechanism by which MYC regulates NK-mediated immune surveillance.

MYC Overexpression During Lymphomagenesis Disrupts Splenic Architecture.

Figures 8A, 8B, 8C:
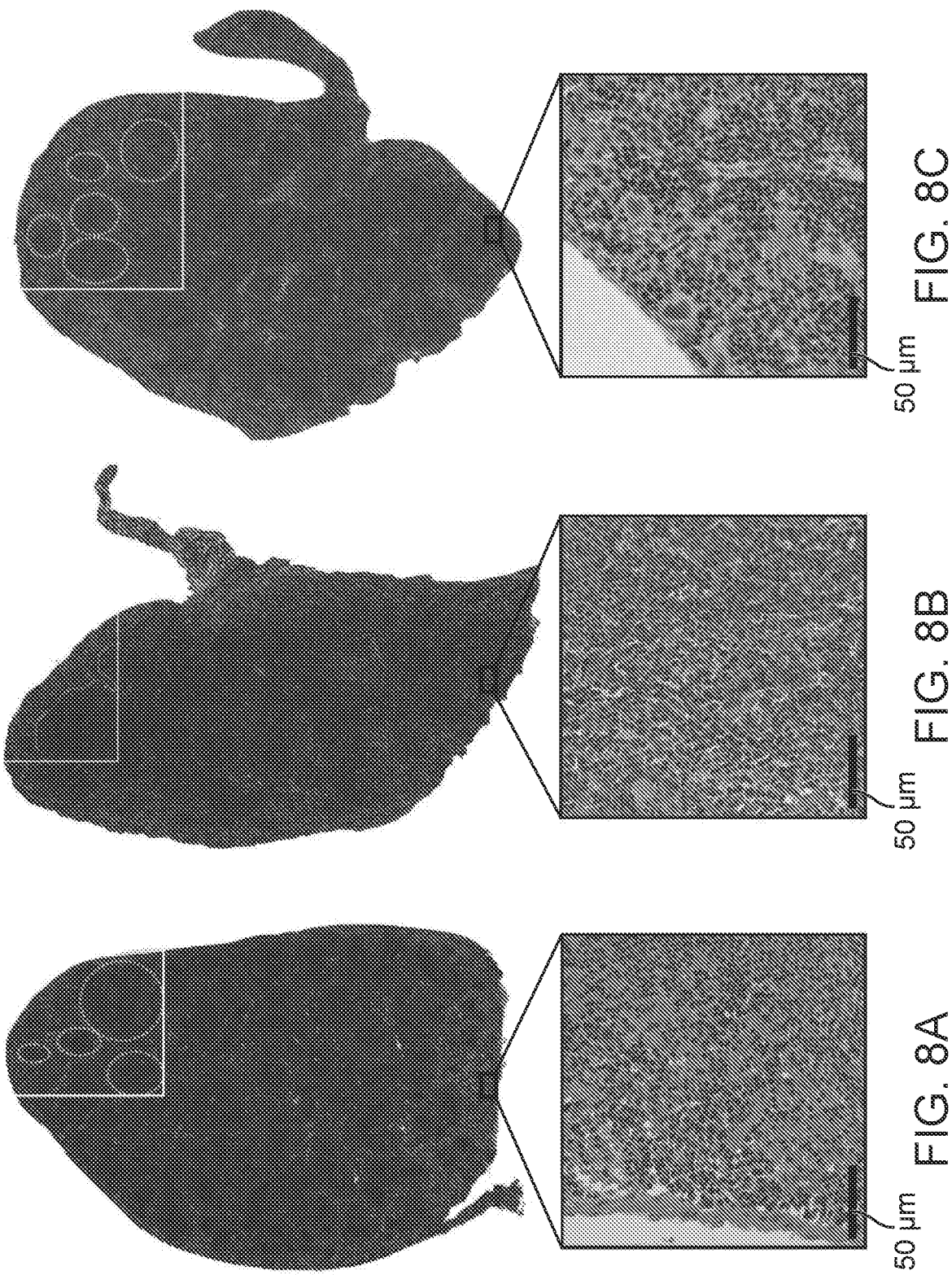
FIG. 8A-8C: MYC-driven T cell lymphomagenesis disturbs splenic architecture. Hematoxylin and Eosin (H&E) staining of spleens isolated from age and sex matched healthy (n=3, FIG. 8A), Eμ-tTA MYC$^{ON}$ (n=3, FIG. 8B) and Eμ-tTA MYC$^{OFF}$ (doxycycline 96 h, n=3, FIG. 8C) mice. White dotted circles depict an intact germinal center in healthy and Eμ-tTA MYC$^{OFF}$ mice (top). Magnification=4×, Scale bars=50 μm.

We evaluated the gross changes in lymphoid organs during overt MYC-driven T lymphomagenesis in Eµ-tTA/tet-O-MYC mice. Eµ-tTA/tet-O-MYC mice succumbed to lymphoma at 2-3 months of age with thymic and splenic involvement. Splenic involvement was associated with splenomegaly in most cases. Irrespective of the presence or absence of splenomegaly, lymphomagenic mice displayed splenic germinal center disruption (white dotted circles, FIG. 8). Inhibition of MYC partially rescued the germinal center architecture of the spleen (FIG. 8). These findings suggested that MYC overexpression in T cell lymphoma might remodel the splenic immune architecture.

Oncogenic MYC Perturbs Normal Composition of Splenic Immune Subsets.

To visualize changes in the immune composition of lymphoid organs during overt lymphomagenesis, we utilized CyTOF. Primary splenic T-lymphoma samples derived from Eµ-tTA/tet-O-MYC mice before ($MYC^{ON}$, n=9) and after ($MYC^{OFF}$, 96 h, n=10) MYC inactivation were examined for immune subsets; and compared to age-matched normal wildtype spleens (FVB/N, n=11). Spleen was chosen for CyTOF experiments for two reasons. First, the spleen contains a diverse immune population including T and B-lymphocytes, natural killer (NK) cells, dendritic cells (DCs), and myeloid cells that help us study interactions between lymphoma cells and their immune microenvironment in situ. Second, the lack of immature pre-T cells in the spleen makes it easier to distinguish between immature leukemic T cells and normal T cells.

Normal spleens contain mature single positive (SP) helper CD4 (CD3+ CD4+ CD8−) and cytotoxic CD8 (CD3+ CD4− CD8+) T cells, and are nearly devoid of the immature DP (CD3+ CD4+CD8+) and immature double negative (DN, CD3+ CD4− CD8-) subsets. Consistent with the phenotype of a T cell lymphoma, the distribution of T cell subsets was altered in the $MYC^{ON}$ cohort with an increase in the percentages of immature CD4+ CD8+ double positive (DP) CD3+ T-cell leukemic blasts as compared to normal mice (FIGS. 1a-c, FIGS. 9a-d). MYC inactivation ($MYC^{OFF}$) resulted in elimination of most DP T cell blasts and restored the distribution of splenic T subsets to normal levels, validating MYC-addiction, as previously described (FIGS. 1a-c, FIGS. 9a-d).

Figure 1D:
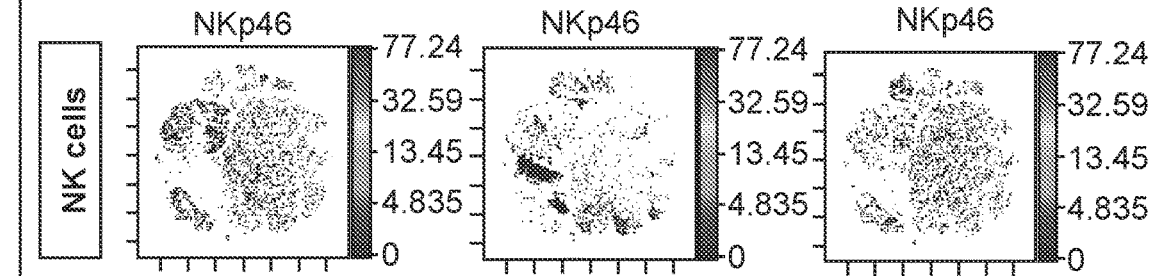
Figure 9A:
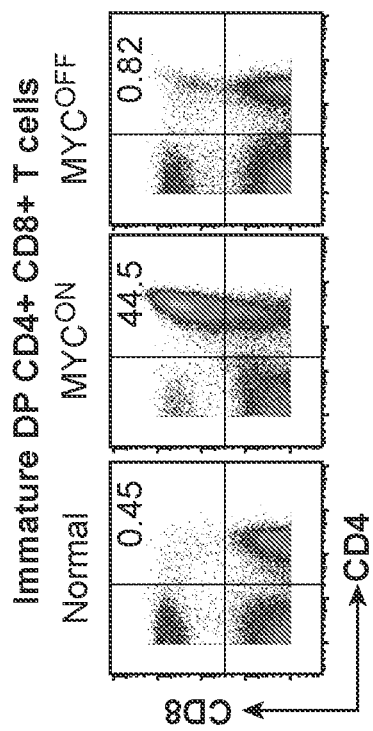
FIG. 9A-9F: MYC hyperactivation in T-lymphoma disturbs splenic immune composition.
Figure 9B:
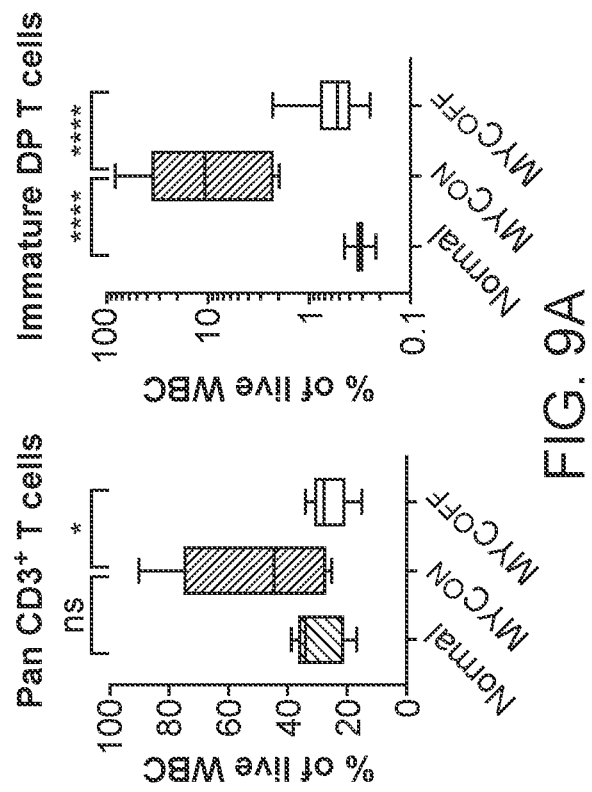
Figure 9C:
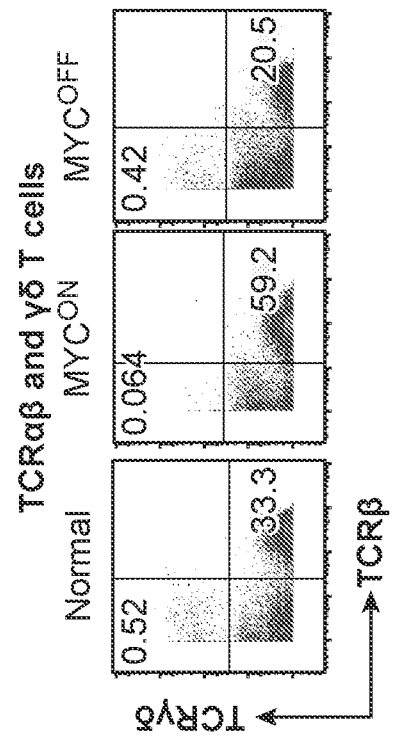
Figure 9D:
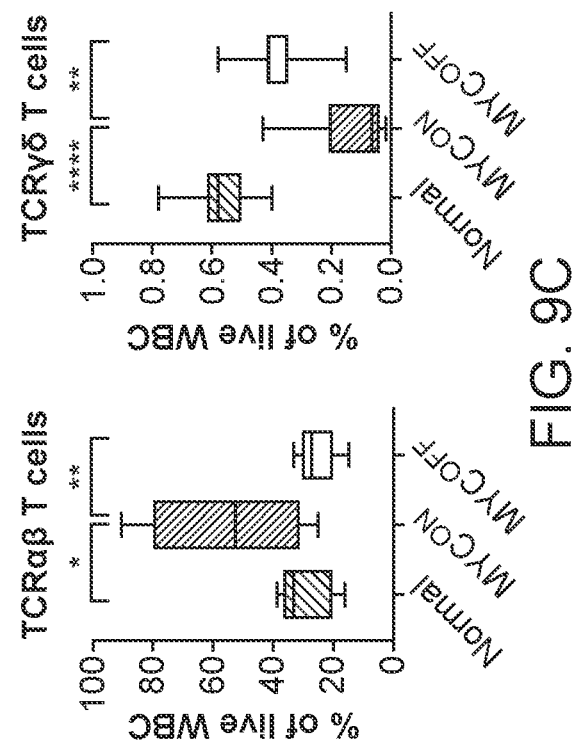
Figures 9E, 9F:
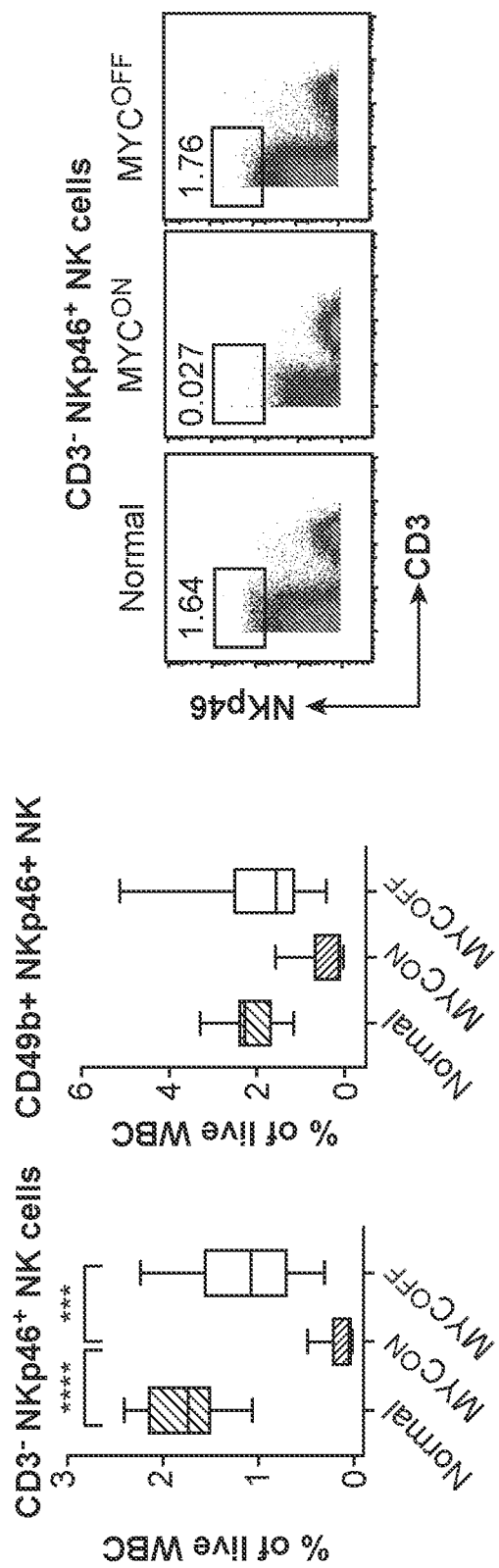

We noted changes in specific immune compartments during MYC-driven T lymphomagenesis by CyTOF. For example, percentages of NK (CD3− NKp46+, FIG. 1d, FIGS. 9e-f), γδ T cell (CD3+ TCRγδ+, FIGS. 9 c-d), and B cell (CD19+, FIGS. 10a-b) subsets were significantly lowered. Yet, NK (FIG. 1d, FIGS. 9e-f), γδ T cell (FIGS. 9c-d) and B cell (FIG. 1e, FIGS. 10a-b) percentages were restored close to normal levels in $MYC^{OFF}$ mice. Other immune compartments including myeloid compartments such as dendritic cells (DCs) and neutrophils were unaltered by the activation of oncogenic MYC (FIGS. 10c-f).

MYC-Driven Lymphomagenesis Specifically Suppresses the Splenic NK Surveillance.

Figure 1E:
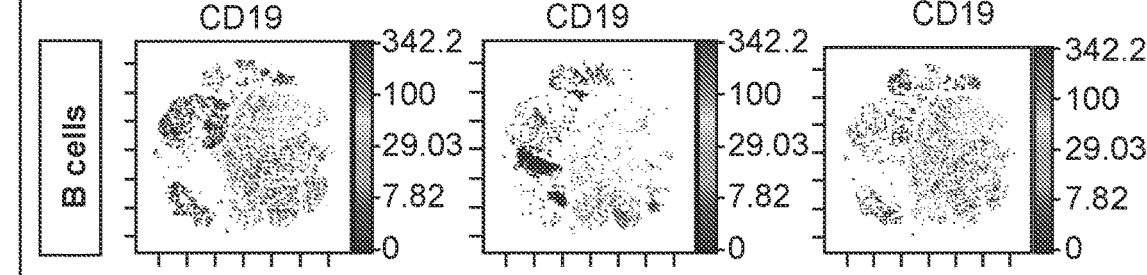
Figure 1F:
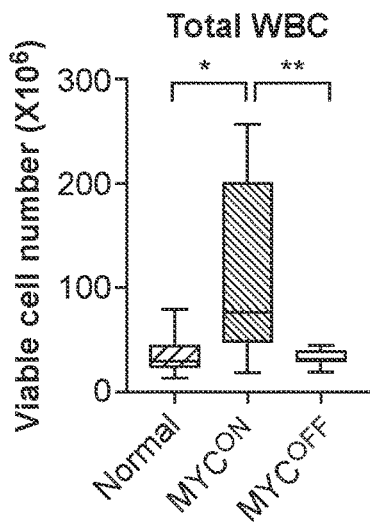
Figure 1G:
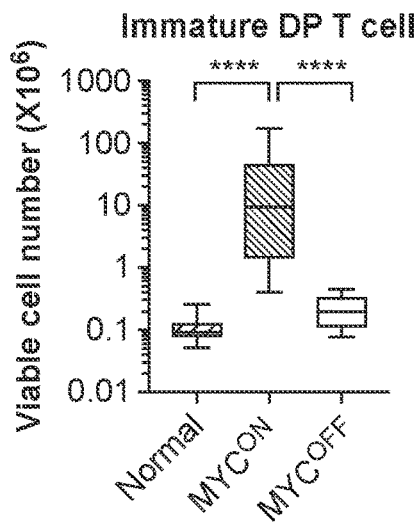
Figure 1H:
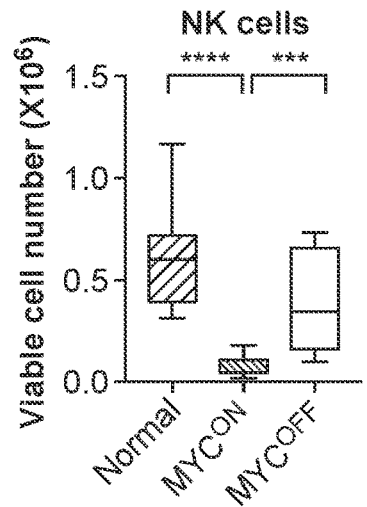
Figure 1I:
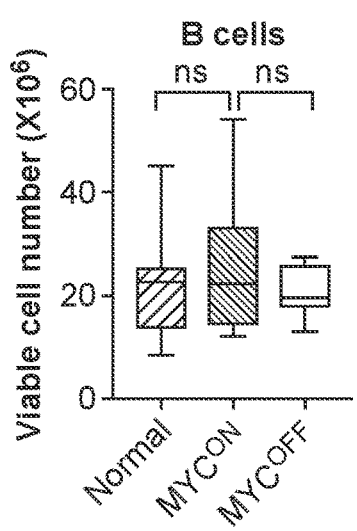
Figure 11A:
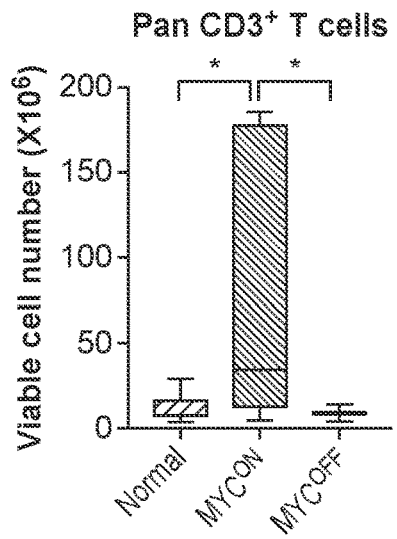
FIG. 11A-11E: Changes in absolute numbers of splenic immune subsets during MYC-driven lymphomagenesis. Quantification of absolute cell numbers of immune compartments in spleens of normal (n=11), Eμ-tTA MYC$^{ON}$ (n=9), and Eμ-tTA MYC$^{OFF}$ (doxycycline 96 h, n=10) mice subjected to mass cytometry. P-values have been calculated using the Mann-Whitney test (ns=not significant, *p<0.05, *p<0.01, p<0.001, p<0.0001).
Figure 11B:
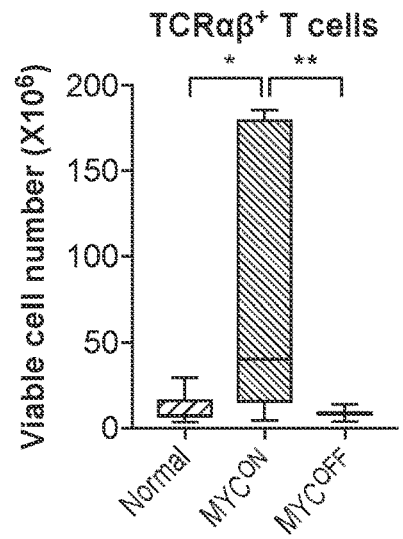
Figure 11C:
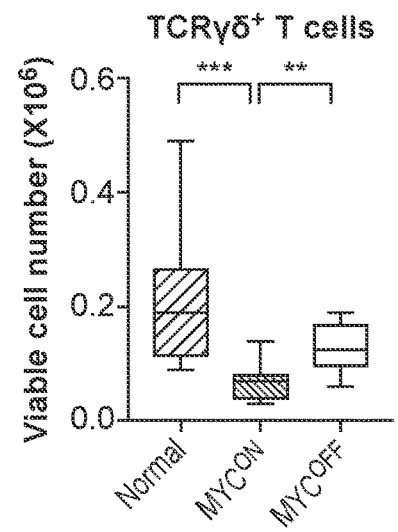

Lymphomagenesis is often associated with splenomegaly and increased splenic cellularity. Therefore, we had to rule out the possibility that apparent reduction in NK cells was because they were passively outnumbered by invading MYC-driven malignant lymphocytes. To address this, we employed two approaches. First, we measured the absolute cell numbers of the immune subsets in the splenic samples subjected to CyTOF. Notably, we observed a statistically significant increase in the cellularity of lymphoma spleens (FIG. 1f). As expected, the absolute cell counts of CD3+ pan T (FIG. 11a), TCRβ+ CD3+ T (FIG. 11b) and, immature CD4+ CD8+ double positive (DP) CD3+ leukemic T cells (FIG. 1g) were increased in $MYC^{ON}$ mice as compared to FVB/N controls. The increase in TCRβ+ CD3+ T compartment was accompanied by a significant reduction in numbers of CD3+ TCRγδ+ γδ T cells (FIG. 11c) in $MYC^{ON}$ mice. Oncogenic MYC significantly lowered absolute cell numbers of CD3− NKp46+ NK cells, whereas MYC inhibition significantly reversed this effect (FIG. 1h). However, absolute numbers of B cells were unaltered in MYC-driven lymphomas as compared to healthy controls (FIG. 1i), although B cell percentages had been significantly reduced in lymphoma-bearing mice (FIG. 1e, FIGS. 10a-b).

Figure 11D:
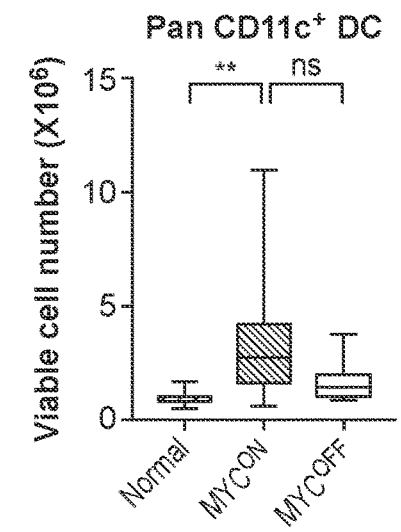
Figure 11E:
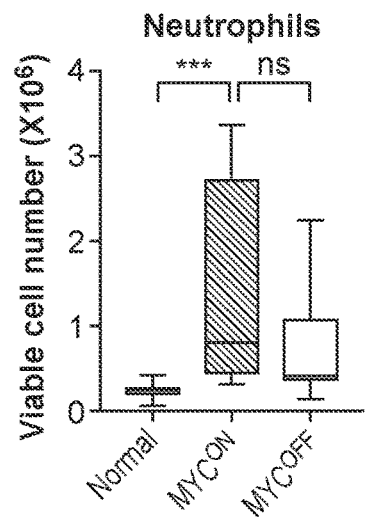

MYC-driven lymphomagenesis significantly increased numbers of pan CD11c+ DCs and neutrophils (FIGS. 11d-e). Second, we calculated the relative composition of every immune subset after gating out all T cells (CD3+ or TCRβ+). Our rationale behind gating out pan T and not just the malignant T fraction was two fold: (1) T-lymphoma results in the developmental blockade during normal T lymphopoiesis, thus disturbing relative distribution of all normal T cells, and (2) We observed that T-lymphoma assumes four major phenotypes (CD3+ CD4+ CD8+ DP, CD3+ CD4+ SP, CD3+ CD8+ SP and CD3+ CD4− CD8− DN), although it arises from the DP T cell fraction (FIG. 12). After gating out T cells, we observed a significant reduction in NK percentages and, an increase in DCs and neutrophils in $MYC^{ON}$ mice (FIG. 13), thus corroborating results obtained after measuring the absolute counts of the immune subsets (FIG. 11). NK cells were the sole immune compartment altered in absolute cell numbers (FIG. 1h) and percentages (FIG. 1d, FIGS. 9e-f) by both MYC induction and inactivation.

Figure 1J:
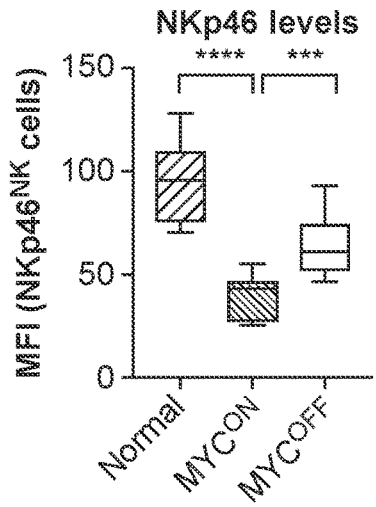
Figure 1K:
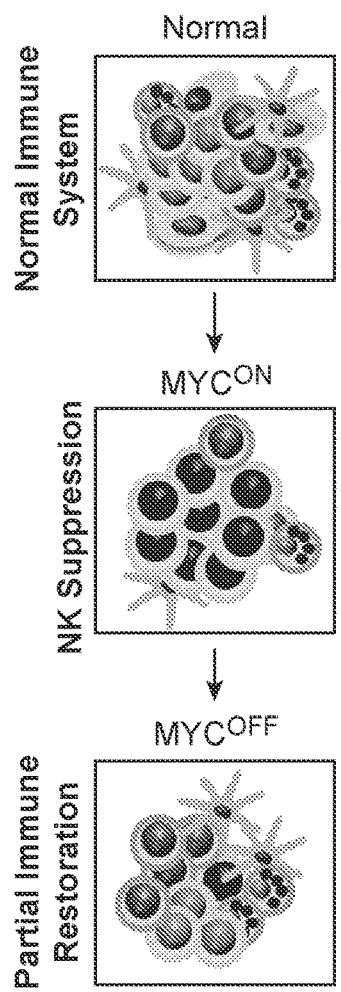

We next interrogated whether oncogenic MYC alters the surface expression of the cytotoxicity and activation marker NKp46 on the residual NK cells in $MYC^{ON}$ mice. Indeed, we observed a significant suppression of surface NKp46 on residual NK cells in $MYC^{ON}$ spleens that was rescued post MYC inactivation (FIG. 1j). Based on these findings, we hypothesized that oncogenic MYC may causally and reversibly suppresses NK cells during MYC-driven lymphomagenesis (FIG. 1k). We focused on the effects of oncogenic MYC on NK-mediated immune surveillance of lymphomas. Our CyTOF results were confirmed by measuring NK cell composition upon MYC activation and inactivation by conventional flow cytometry (FIG. 14). MYC activation significantly lowered the CD3− Nkp46+/CD3− CD49b+ NKp46+/NK1.1+ NKp46+NK fraction (FIGS. 14d-i).

Figure 13:
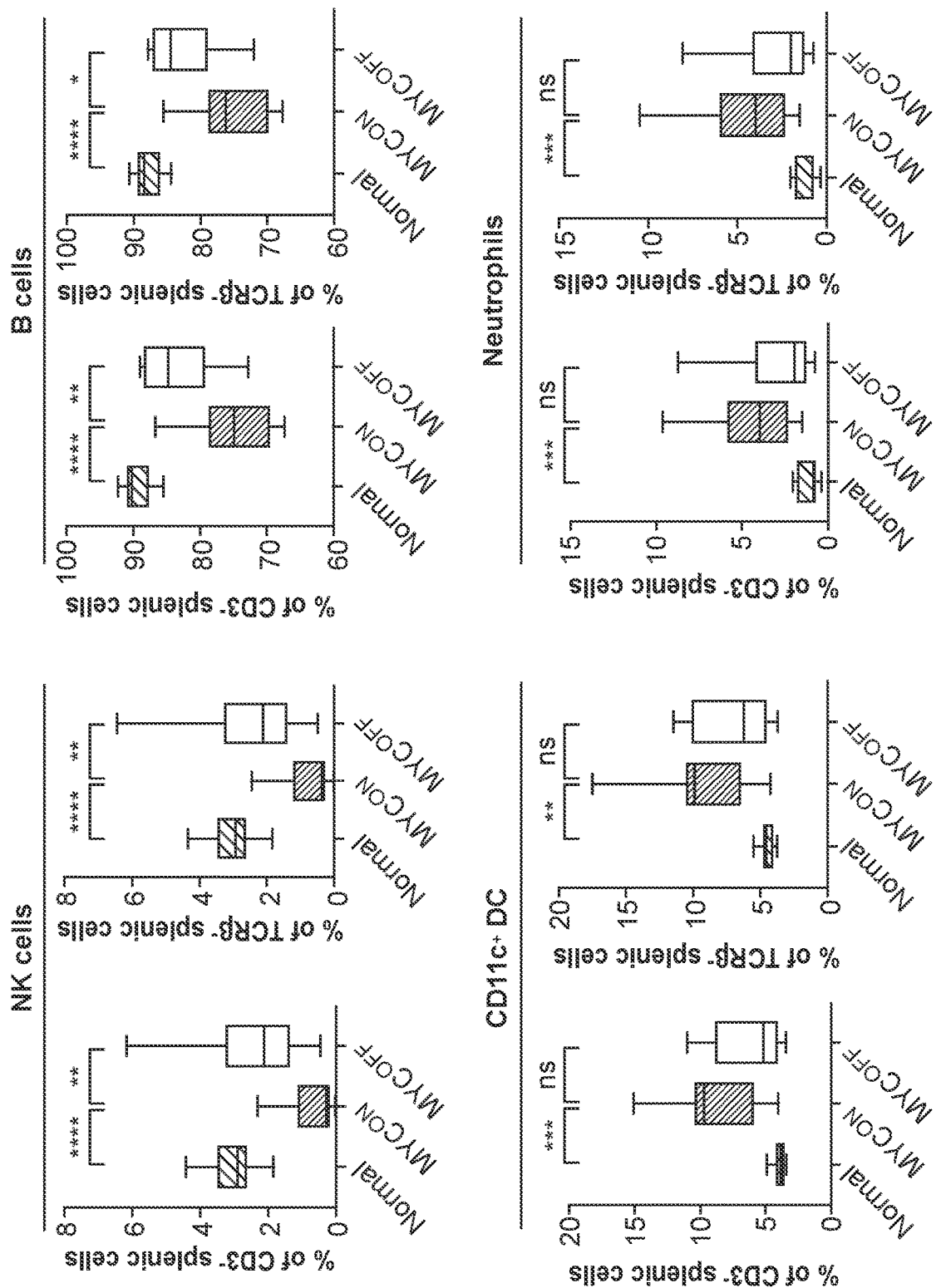
FIG. 13: Changes in percentages of splenic immune compartments as a function of CD3$^−$ and TCRβ− cells. Quantification of percentages of immune compartments in spleens of normal (n=11), Eμ-tTA MYC$^{ON}$ (n=9), and Eμ-tTA MYC$^{OFF}$ (doxycycline 96 h, n=10) mice subjected to CyTOF after gating out splenic T cells (CD3$^+$ or TCRβ$^+$). P-values have been calculated using the Mann-Whitney test (*p<0.05, p<0.01, *p<0.001, **p<0.0001).
Figure 14H:
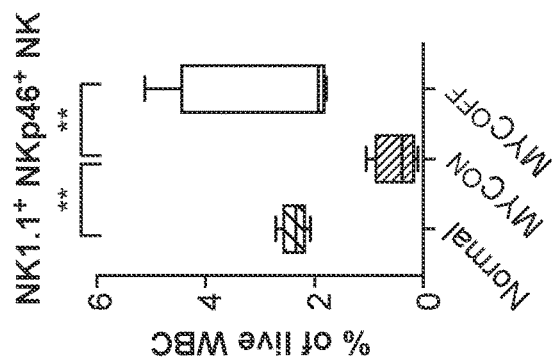
Figure 14G:
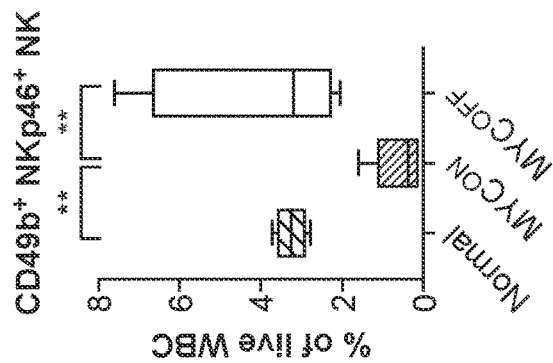
Figure 14F:
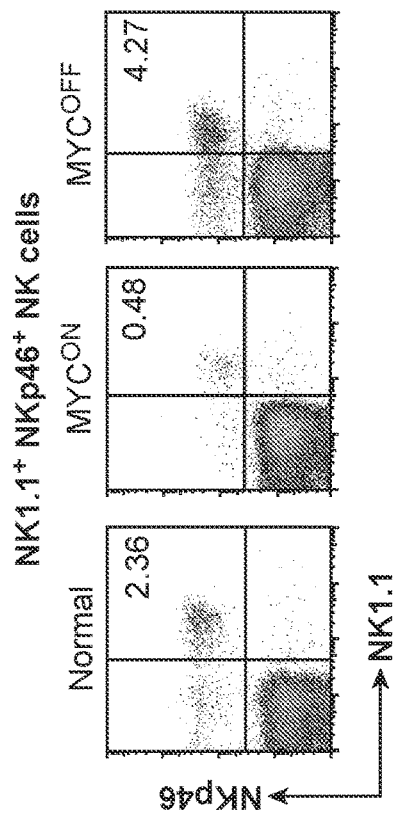
Figure 14I:
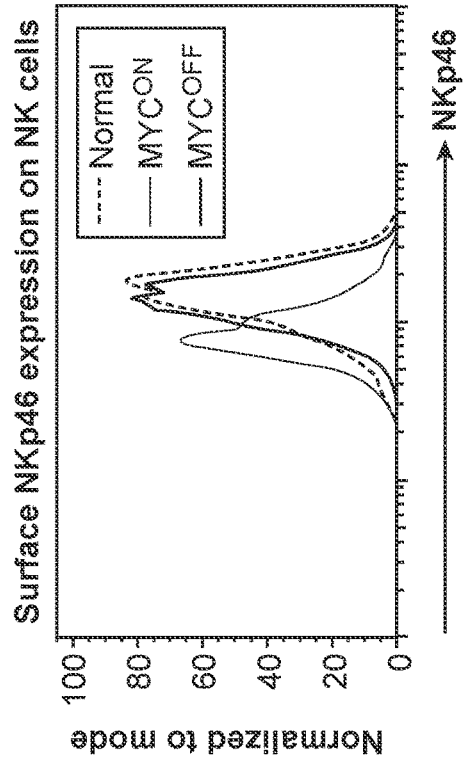

Next, using CIBERSORT, a computational method for determining immune compositions from bulk gene expression data, changes in NK composition were measured in CyTOF-matched spleens from normal (n=3), $MYC^{ON}$ (n=3) and MYC (n=3) mice. The CIBERSORT NK percentages are concordant with those obtained by CyTOF (FIG. 13). Our results further confirm the suppression of NK-mediated surveillance in MYC-driven lymphomas seen in CyTOF.

NK Suppression During MYC-Driven Lymphomagenesis is Systemic in Nature.

We examined whether the phenomenon of NK suppression occurs in other lymphoid organs where malignant T-lymphoblasts have infiltrated, including the blood and bone marrow. Circulating NK cell percentages (FIGS. 2a-c, FIG. 16), numbers per µl of blood (FIG. 2d), and cytotoxicity/activity (NKp46 MFI, FIG. 2e) were reduced in overt lymphoma mice ($MYC^{ON}$, n=6), as compared to normal (n=6) and MYC-inactivated ($MYC^{OFF}$, n=6) mice.

Figure 17G:
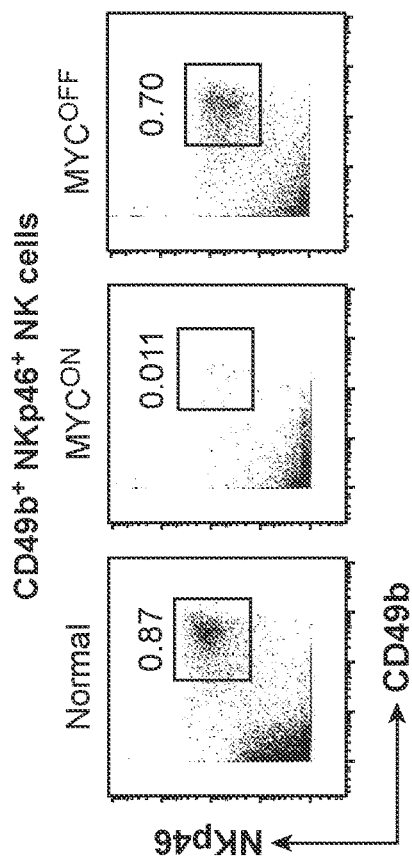
Figure 17I:
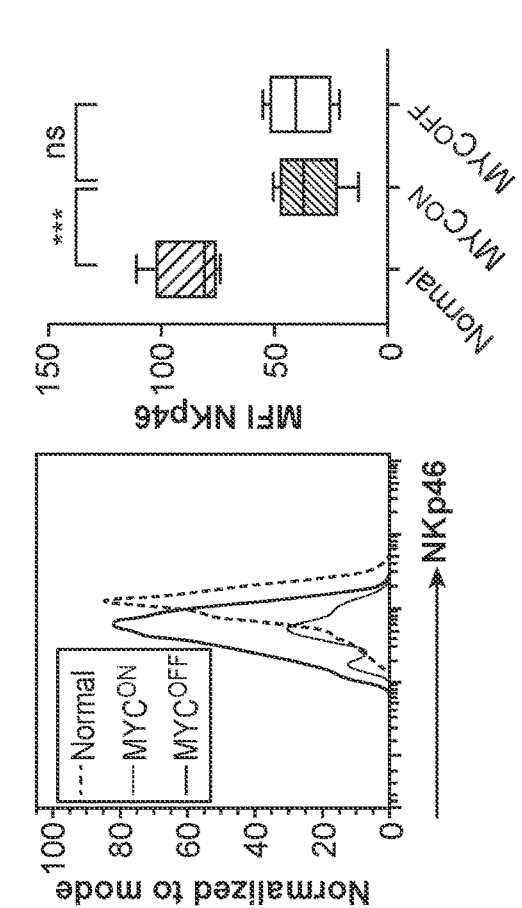
Figure 17H:
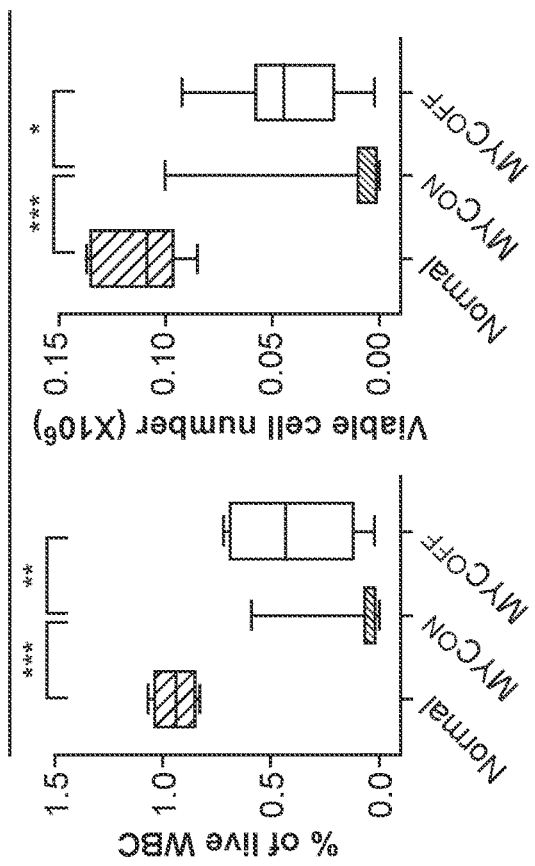

Next, we interrogated whether MYC-driven T-lymphomagenesis leads to NK suppression in the bone marrow. T cell lymphoma in our model manifests with significant bone marrow involvement (FIGS. 17a-f). Interestingly, mature NK cells were significantly suppressed in bone marrow of lymphoma-bearing mice (MYC$^{ON}$, n=7), as compared to normal (n=9) and, MYC-inactivated (MYC$^{OFF}$, n=7) mice (FIGS. 17d-i). NK percentages and numbers were significantly restored to normalcy post MYC inactivation in bone marrow (FIG. 17h). In contrast, surface expression of NKp46 was not restored (FIG. 17i). This may be because increase in NKp46 occurs during final maturation of NK cells outside the marrow. These mature NK cells may not have circulated back to the marrow within 4 days of MYC inactivation. The disappearance of NK cells in the bone marrow suggests that MYC-driven lymphomagenesis abrogates the replenishment of mature CD3-NKp46+ NK cells in spleen and blood, leading to systemic suppression of NK mediated immune surveillance.

NK Suppression During Lymphomagenesis is MYC-Dependent.

We recognize that an alternative explanation for our results is that rather than directly regulating NK suppression the MYC oncogene indirectly allows for NK expansion through creation of niche space vacated by the loss of malignant cells post MYC inactivation. Therefore, we compared percentages and NKp46 expression in splenic (FIGS. 2f-h) and, circulating (FIGS. 2i-k) NK cells in MYC$^{OFF}$ mice (with residual blasts) alongside lymphoma-bearing mice (MYC$^{ON}$) with similar blast percentages. The presence of residual lymphoblasts in MYC$^{OFF}$ mice may be attributed to (1) initial high disease burden before inactivating MYC, or (2) partial differentiation of lymphoblasts after MYC inactivation. We observed that MYC inactivation leads to increase in percentages (FIGS. 2g, j) and cytotoxicity (FIGS. 2h, k) of NK cells even in the presence of residual lymphoblasts (FIGS. 2f, i). Hence, we infer that NK suppression is MYC-dependent, and does not occur because lymphoma cells are cleared after MYC inactivation.

NK-Mediated Surveillance Delays Initiation and Relapse of MYC-Driven Lymphomas.

Figure 18:
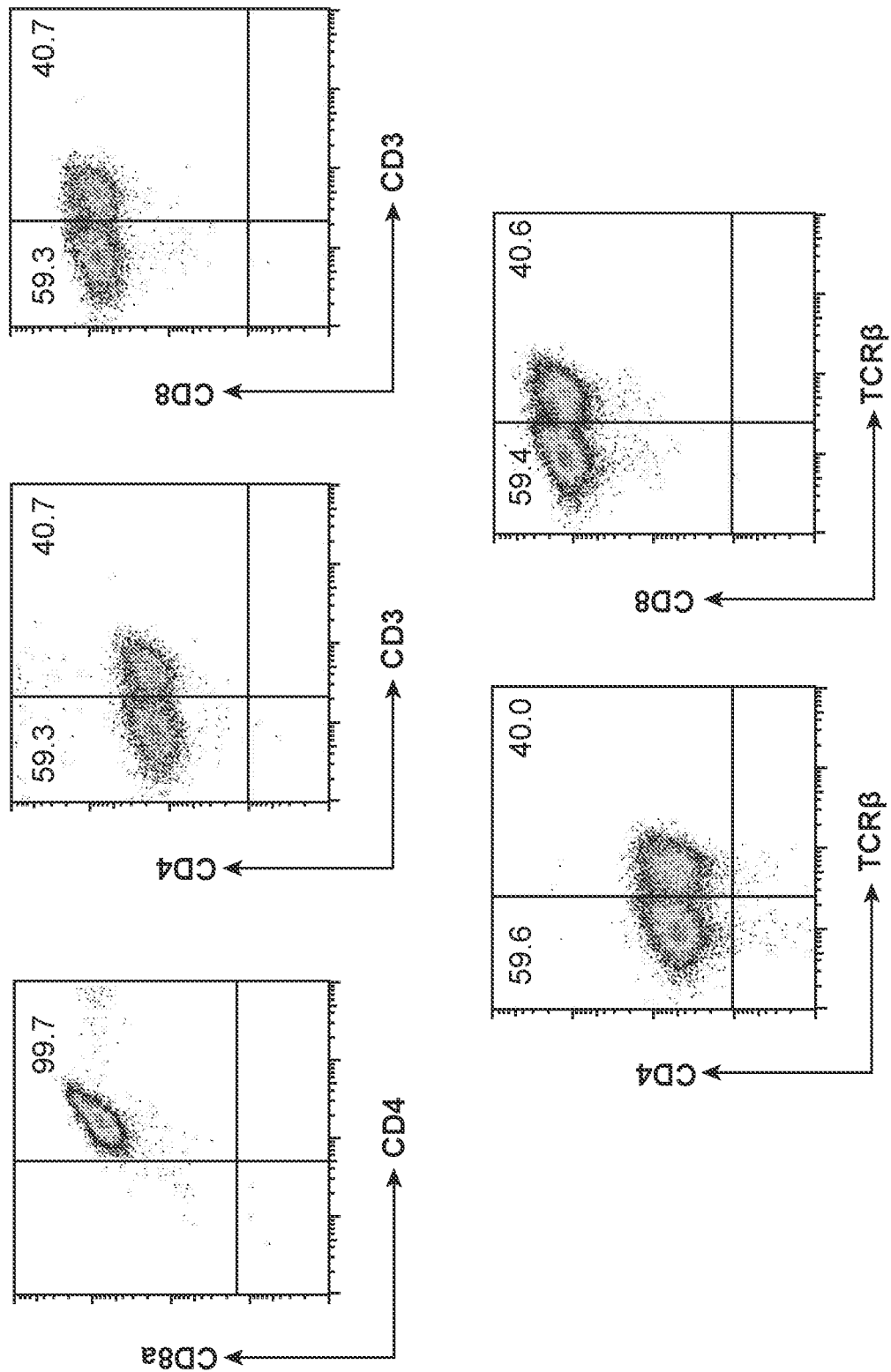
FIG. 18: Flow cytometry validation of a T-lymphoma cell line derived from an Eµ-tTA Tet O MYC mouse. Flow cytometry plots depicting the surface expression of T cell markers, such as CD3, CD4, CD8 and TCRβ in a cell line derived from Eµ-tTA Tet O MYC mice.

We examined the role of NK cells during lymphomagenesis. MYC-driven T-lymphoma cells derived from Eμ-tTA/tet-O-MYC mice (FIG. 18) were injected intravenously into mice with (NOD SCID) or without (NOD SCID IL-2Rγ$^{-/-}$) NK cells. Lymphoma onset and morbidity of mice was significantly delayed in NOD SCID transplant recipients with NK cells (day 6 for NOD SCID IL-2 Rγ$^{-/-}$ and day 18 for NOD SCID, FIG. 3ab). T-ALL cells eventually engrafted in the bone marrow of NOD SCID mice where NK cells are present (FIGS. 3a-b). We infer that while NK-mediated immune surveillance initially blocks MYC-driven lymphomagenesis, continued MYC expression eventually suppresses NK cells to establish lymphomas, as seen in primary Eμ-tTA/tet-O-MYC mice. MYC-driven lymphomas recur post MYC inactivation in immune-deficient hosts (NOD SCID IL-2R Rγ$^{-/-}$) in comparison to immune-competent hosts where MYC inactivation sustains lymphoma regression.

Figure 19:
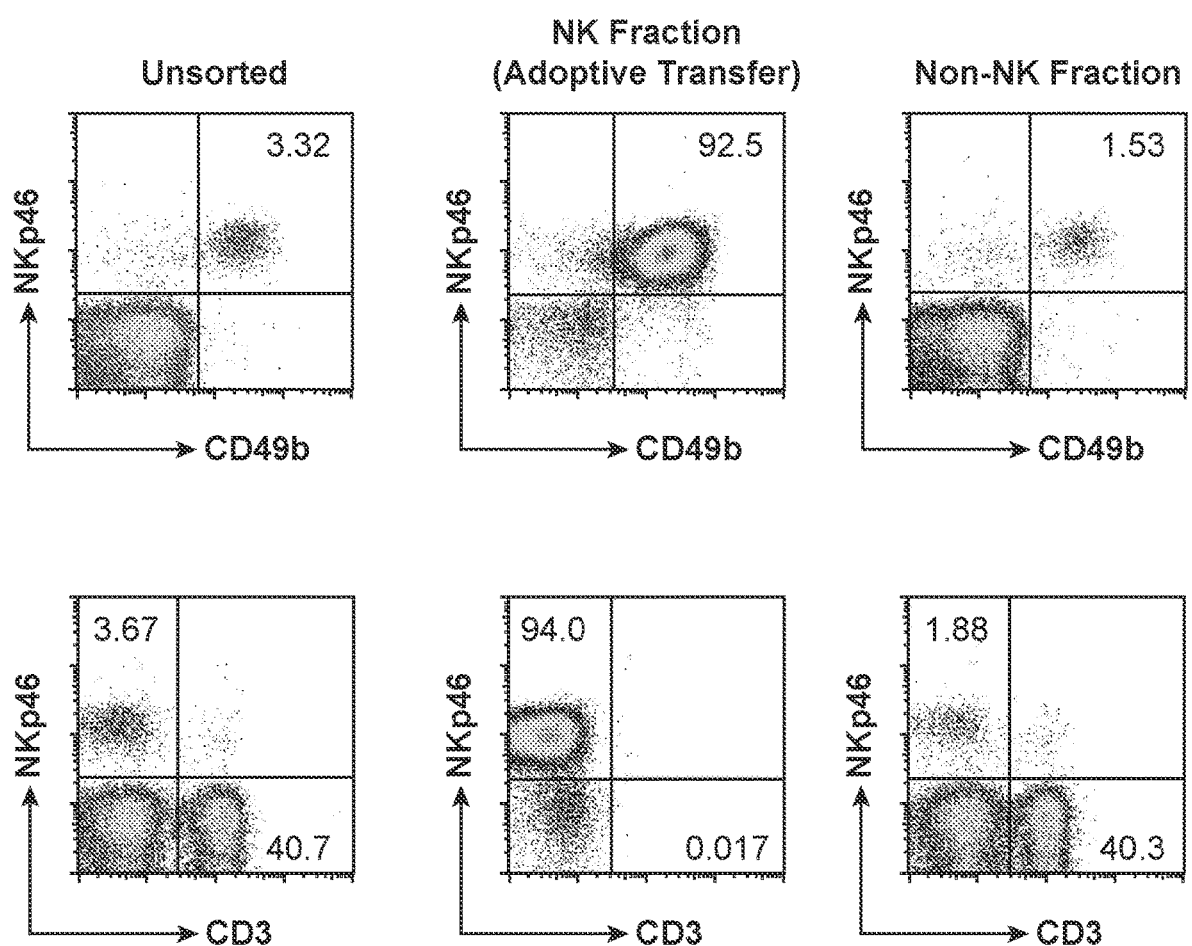
FIG. 19: Isolation and purification of NK cells for adoptive transfer into MYC-driven T-ALL bearing NSG recipients. Validation of purity of NK cells isolated by magnetic activated cell sorting (MACS) by flow cytometry for surface CD3, Nkp46 and CD49b.

We investigated whether NK cells alone can block lymphoma recurrence post MYC inactivation. Syngeneic NK cells from FVB/N mice (FIG. 19) when adoptively transferred into T cell lymphoma-bearing NOD SCID IL-2Rγ−/− recipients at the time of MYC inactivation (FIG. 3c), delayed lymphoma recurrence (FIGS. 3c-d), and prolonged overall survival (FIG. 3e) when compared to vehicle-treated controls. Thus, the NK subset represents an important immune compartment in the sustenance of lymphoma regression post MYC inactivation.

We observed that lymphomas that recurred post MYC inactivation in both vehicle and adoptive NK cell-treated groups (FIG. 3c) continued to exhibit MYC addiction, because of mutations (H100Y and E174K) acquired in the tTA element (FIG. 20) that lead to MYC reactivation. We infer that signals from MYC-reactivated lymphomas causally suppress and eliminate the adoptively transferred NK cells (FIG. 3c).

Next, we transiently depleted NK cells in 4-week old Eμ-tTA/tet-O-MYC mice using the NK1.1 antibody, before the onset of overt lymphomagenesis. The depletion of NK cells had no effect on the survival and time to overt lymphoma onset, as compared to Eμ-tTA/tet-O-MYC mice treated with control antibody (FIG. 3f). Lymphomas that arise in the control antibody-treated cohort also exhibit NK suppression (FIG. 3g). These results lead to two important conclusions: (1) Oncogenic MYC actively excludes NK cells, and (2) Signals for NK suppression may arise in a lymphoma inside-out fashion from the MYC-driven malignant lymphocytes.

Oncogenic MYC Prevents NK Surveillance by Suppressing Type I IFN Signaling.

Figure 21:
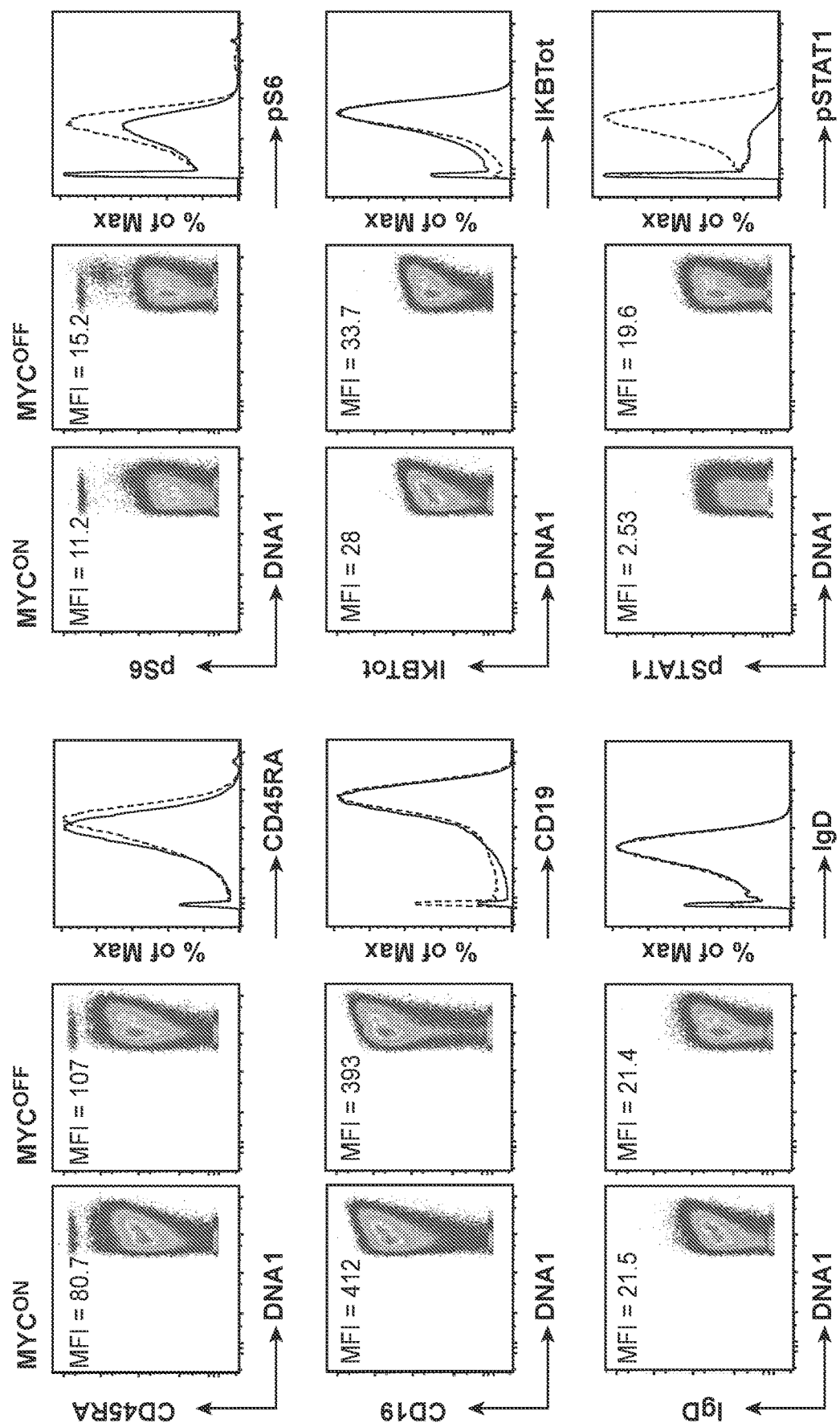
Figure 21:
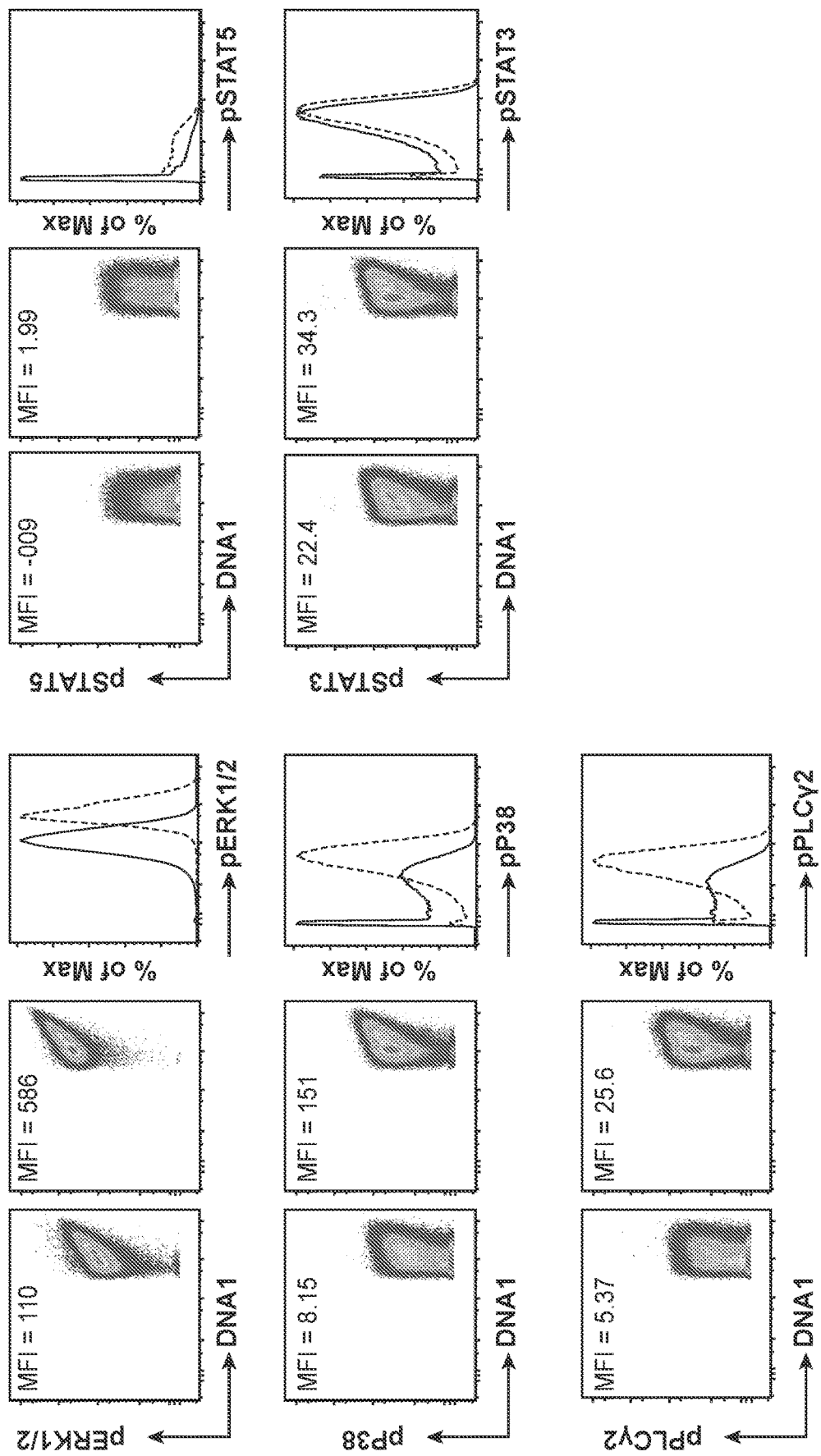

Our results (FIGS. 3f-g) show that MYC-driven lymphomagenic signaling drives NK suppression in the microenvironment. Since BL is a classic human MYC-associated lymphoid cancer, we measured global signaling changes in an EBV-transformed human B cell line that expresses MYC regulated by the Tet System (P493-6), and mimics BL. We compared global signaling changes by Phospho-CyTOF before (MYC$^{ON/HIGH}$) and after (MYC$^{OFF/LOW}$) MYC inhibition in P493-6 BL-like cells (FIG. 22). We confirmed that MYC is inducibly expressed in P493-6 cells (FIG. 4a). Phospho-CyTOF revealed an activation of Mitogen Activated Protein Kinase (MAPK) and calcium signaling including pERK1/2 (FIG. 4b), pP38 and pPLCγ2 (FIG. 4c, FIG. 21). Amongst the key cytokine signaling pathways that operate through the Janus Kinases (JAKs) and Signal Transducers and Activators of Transcription (STATs), MYC inactivation resulted in the activation of STAT1 in P493-6 cells (FIGS. 4b-e, FIG. 21). MYC inactivation increased STAT1 phosphorylation and activity (FIGS. 4b-d), STAT1 transcription (FIG. 4e, FIG. 22a) and STAT1 protein production (FIG. 4d).

Figure 23:
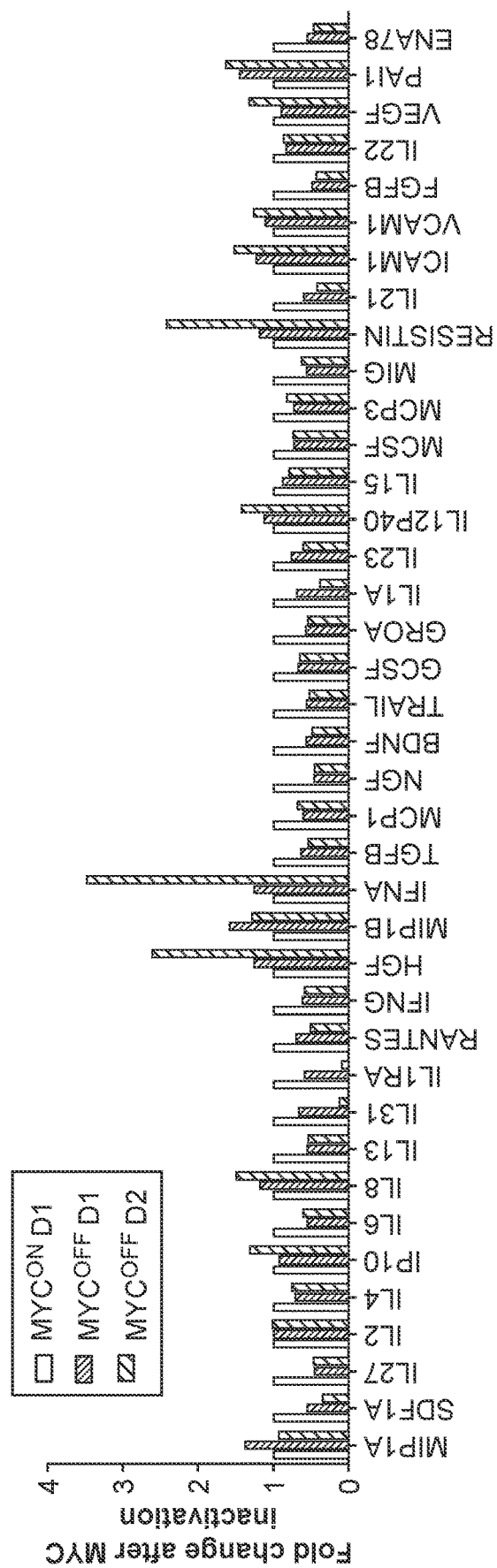
FIG. 23: MYC inactivation in BL changes the secreted cytokine profile. Luminex was used to evaluate the global changes in cytokine secretion post MYC inactivation for 24 h (D1) and 48 h (D2) in the P493-6 BL model. Each time point was carried out in duplicates. Average of these duplicates is shown.

Interestingly, STAT2, the binding partner of STAT1 was also transactivated post MYC inhibition in P493-6 cells (FIG. 4e, FIG. 22b). The activation of ERK1/2-STAT1/2 signaling post MYC inactivation resembles the antiviral NK-mediated immune response that is associated with Type I interferons (IFNs). Indeed, transcript level of Type I IFN, Ifnα2 was significantly elevated after MYC inactivation in P493-6 cells (MYC$^{OFF/LOW}$, FIG. 40. A complete cytokine profiling of the P493-6 cells pre- and post-MYC inactivation demonstrated that the secretion of IFNα is significantly upregulated in the MYC$^{OFF/LOW}$ in comparison to the MYC$^{ON/HIGH}$ (FIG. 4f, FIG. 23). MYC may modulate cytokine expression by suppressing ERK1/2-STAT1/2-Type I IFN signaling, and thereby drive NK cells away from the tumor microenvironment.

Figure 24:
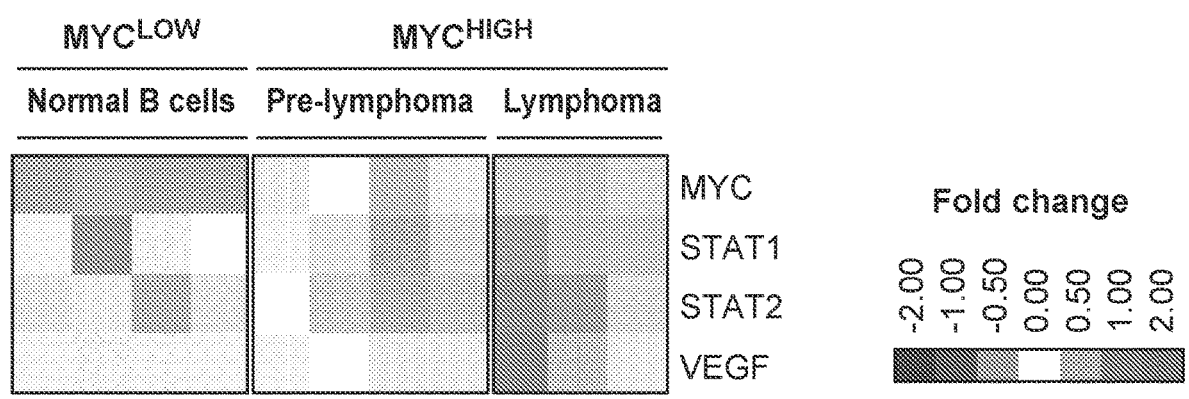
FIG. 24: Transcriptional repression of STAT1 and STAT2 during murine MYC-driven B cell lymphomagenesis. Heat map comparing transcriptional changes in Stat1 and Stat2 genes in normal B cells from healthy mice (MYCLOW, n=4), pre-lymphomagenic B cells from Eµ-MYC mice (pre-lymphoma, MYCHIGH, n=4), and in full blown primary B cell lymphomas from Eµ-MYC mice (MYCHIGH, n=3) using RNA sequencing (GSE 51008).

Tumor-intrinsic signaling changes post MYC inactivation in T-lymphoma cell line derived from Eμ-tTA/tet-O-MYC mice (FIG. 18), mirrored those observed in the human BL-like model, with MYC inactivation leading to activation of ERK1/2-STAT1/2-Type I IFN signaling (FIGS. 4h-j, FIGS. 22c-d). Next, we compared transcript levels of STAT1 and STAT2 in normal B cells (MYC$^{LOW}$, n=4), pre-lymphoma B cells from Eμ-MYC mice (MYC$^{HIGH}$, n=4), and overt B cell lymphoma from Eμ-MYC mice (MYC$^{HIGH}$, n=3). A sequential increase in MYC during stepwise B cell transformation is accompanied by transcriptional suppression of STAT1 and STAT2 (FIG. 24), suggesting that suppression of STAT1/2-Type I IFN signaling is a signature of MYC-driven lymphomagenesis.

Type I IFN Treatment Enhances NK Surveillance of MYC-Driven Lymphomas.

Figures 15A, 15B:
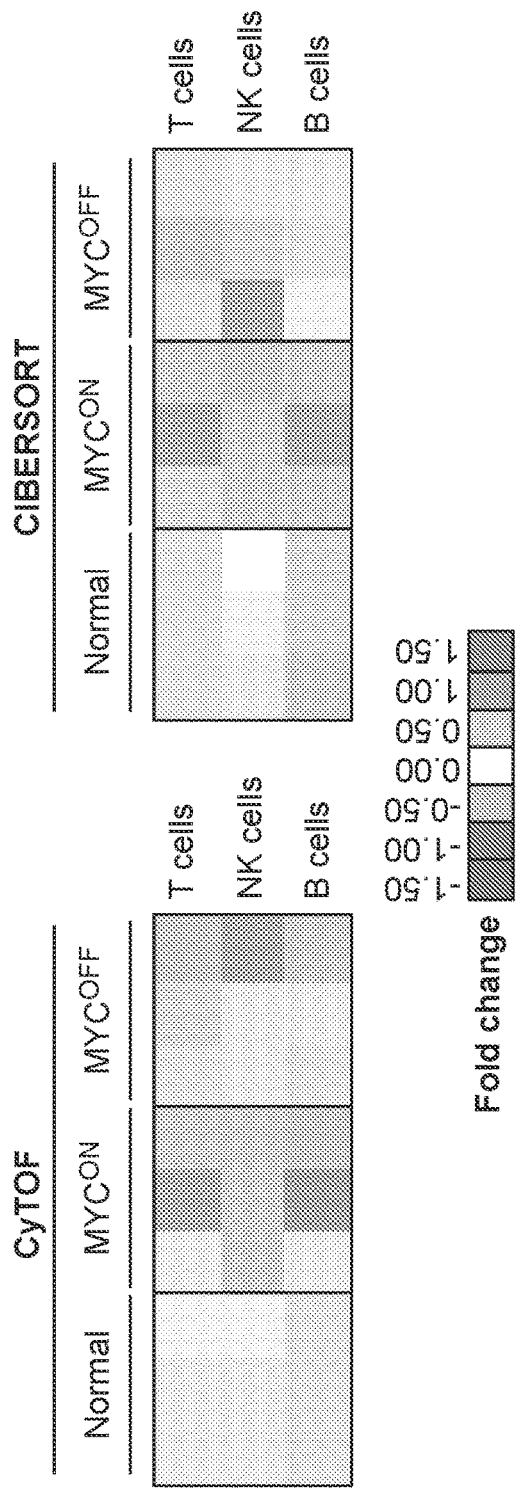
FIG. 15A-15B: CIBERSORT measuring changes in splenic NK composition during MYC-driven lymphomagenesis.
Figure 16H:
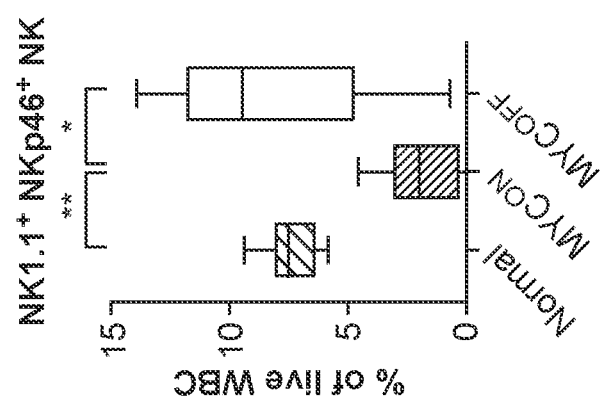
Figure 16G:
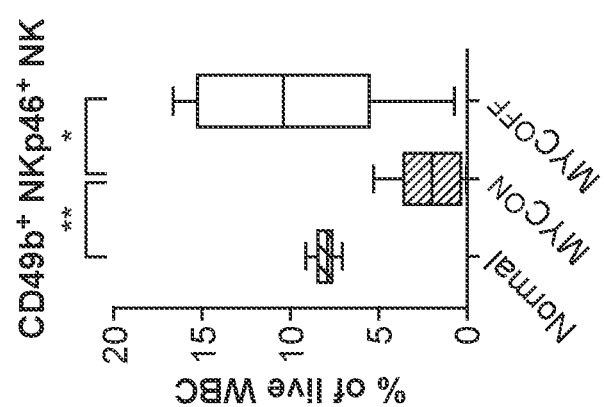

Type I IFNs are known to be required for maturation, expansion and activation of NK cells. It is of interest to note that mice deficient in Type I IFN receptors (IFNAR$^{-/-}$) show significantly lower levels of NK cells in spleens when compared to normal mice; a phenomenon we observe during MYC-driven lymphomagenesis (FIGS. 1-2, FIG. 15). RNA sequencing analyses of bulk splenic cells from normal (n=3), Eμ-tTA MYC$^{ON}$ (n=3) and Eμ-tTA MYC$^{OFF}$ (n=3) mice showed that each group had a unique gene expression signature (FIG. 5a). We also observed enrichment of JAK-STAT-Type I IFN (FIGS. 5b-e) and ERK1/2-MAPK (FIG. 25) signatures in normal and MYC$^{OFF}$ mice when compared to MYC$^{ON}$ mice. Similarly, we observed a suppression of NK signature in MYC$^{ON}$ spleens when compared to normal and MYC$^{OFF}$ spleens (FIG. 5f), suggesting a correlation between ERK1/2-STAT1/2-Type I IFN signature and splenic NK compositions in the three groups. We conclude that MYC subverts normal immunological processes of NK cell development by suppressing ERK1/2-STAT1/2 signaling cascade and Type I IFN secretion.

Figure 6A:
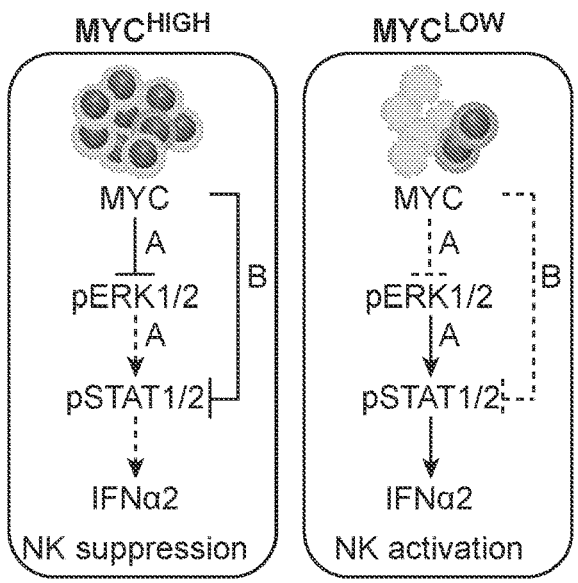
FIG. 6A-6I: MYC-mediated repression of STAT1-STAT2-IFN signaling proceeds in a MIZ1-dependent manner that is independent of ERK1/2 activation.
Figure 6B:
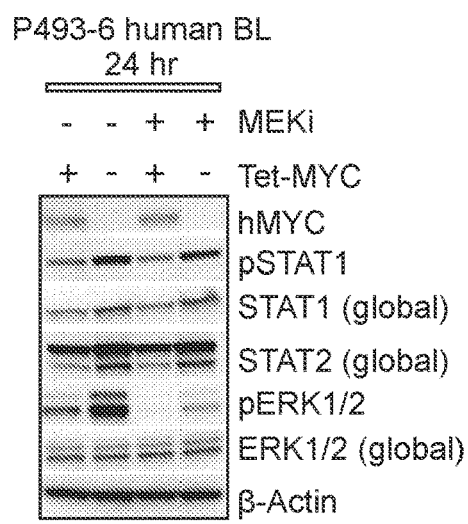
Figure 6C:
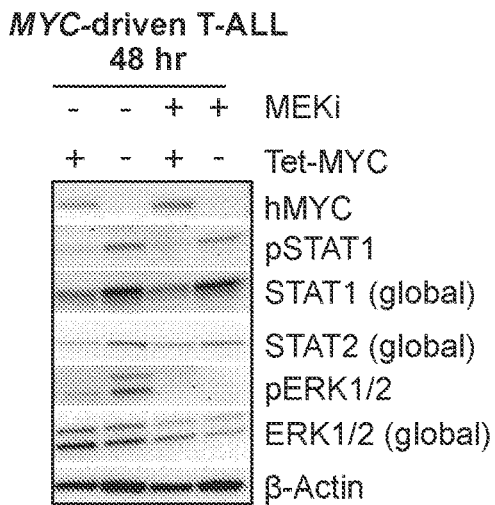
Figure 6D:
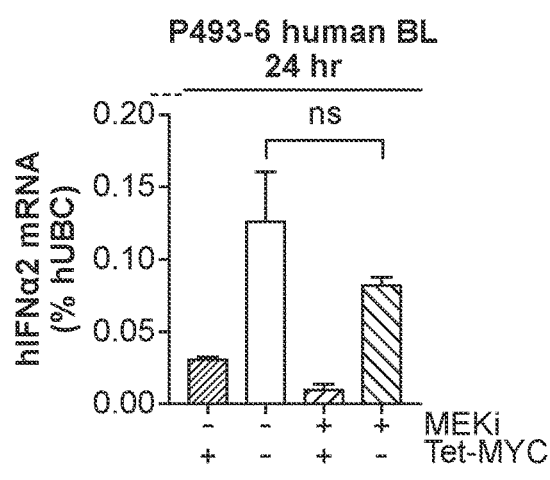
Figure 6E:
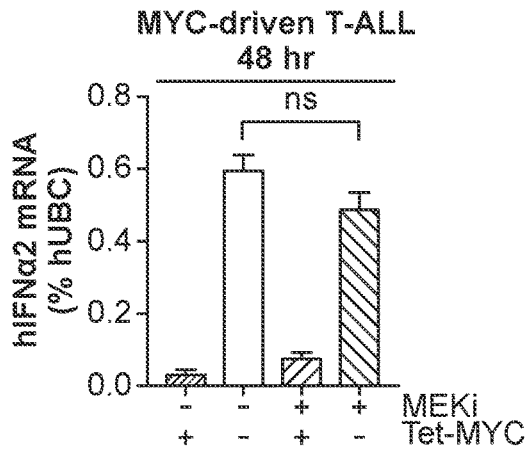
Figures 27A, 27B:
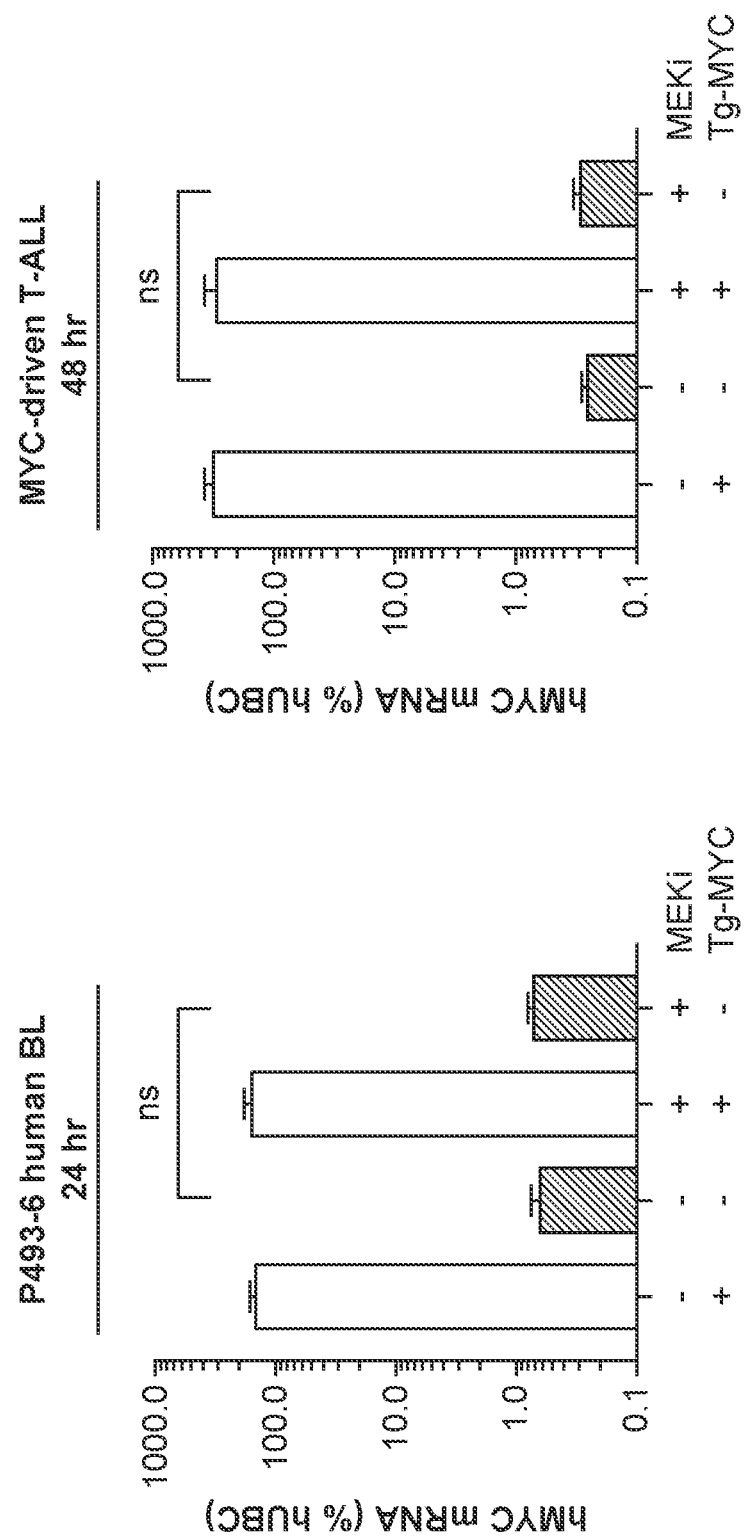
FIG. 27A-27B: MYC levels in lymphoma lines post combined inactivation of MYC and ERK.

We investigated whether administration of Type I IFN to Eμ-tTA/tet-O-MYC mice bearing overt T cell lymphoma can increase infiltration of NK cells into spleens. The percentages and numbers of CD3- Nkp46+ NK cells were significantly increased in IFNα-treated mice when compared to corresponding litter-matched lymphoma mice treated with vehicle (PBS) (FIGS. 5g-k, FIG. 26). Of note, total numbers and percentages of WBC, CD3 T cells and DP immature T cells remain unaltered between the control and the treatment groups (FIGS. 5h-j), thus highlighting the specific importance of Type I IFN levels in NK cell homeostasis. ERK1/2 activation is dispensable for induction of Type I IFN signaling post MYC inactivation We investigated the molecular mechanism by which MYC regulates Type I IFN signaling. As the first logical possibility, we evaluated whether ERK1/2 activation is required for induction of STAT1/2-Type I IFN signaling after MYC inactivation (FIG. 6a, Pathway A). To this end, we measured changes in STAT1/2-Type I IFN signaling after blocking ERK1/2 phosphorylation using a MEK inhibitor (MEKi) in P493-6 human BL (FIG. 6b, FIG. 27a) and mouse MYC-driven T-ALL (FIG. 6c, FIG. 27b) cells. Blocking ERK1/2 phosphorylation did not abrogate the activation of STAT1/2 post MYC inactivation (FIGS. 6b-c). MEKi treatment did not prevent the increase in transcript levels of Type I IFNα2 that occurs as a consequence of MYC inactivation (FIGS. 6d-e). Therefore, ERK1/2 activation is dispensable for inducing the STAT1/2-Type I IFN signaling cascade upon MYC inactivation.

MYC Transcriptionally Represses the Activaton of STAT T1/2-Type I IFN Signaling.

Figure 6F:
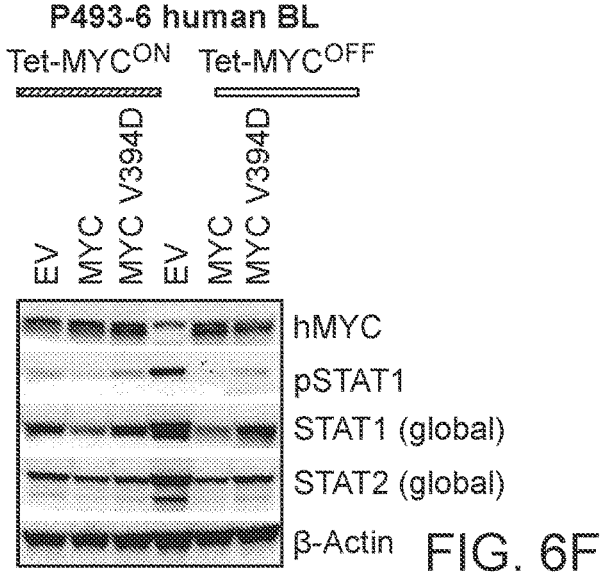
Figures 6G, 6H:
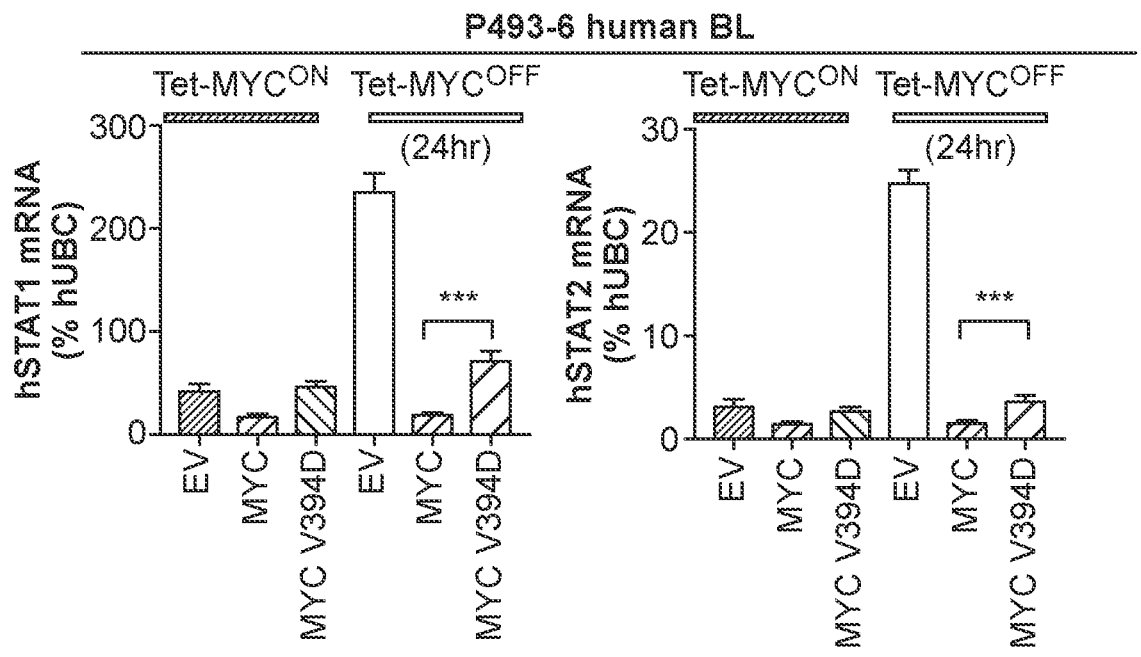
Figure 6I:
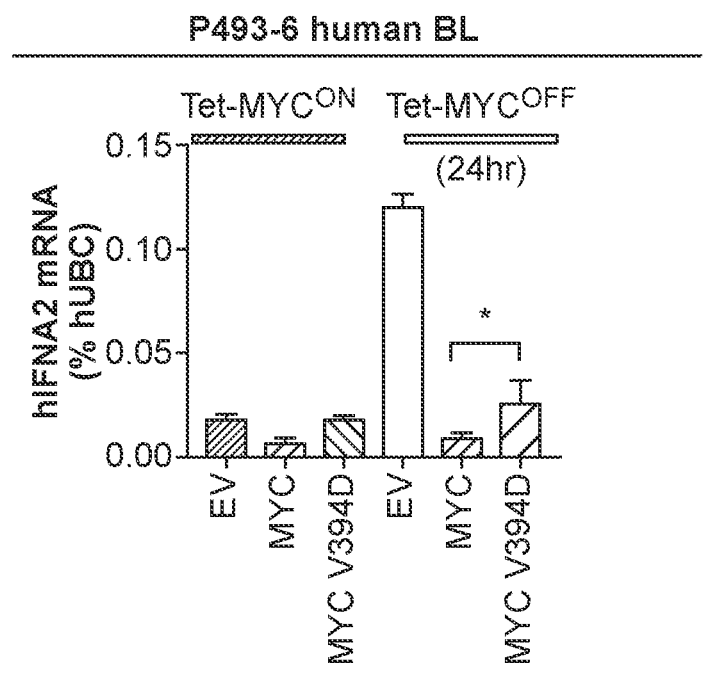

We tested the possibility of MYC transcriptionally repressing STAT1/2-Type I IFN signaling cascade (FIG. 6a, Pathway B). Although widely known as a transactivator, MYC can inhibit the transcription of genes by sequestering transactivators such as MIZ1 and Sp1/Sp3, and binding to Initiator (Inr) elements in gene promoters. For example, MYC inhibition releases MYC-MAX heterodimers from the binding sites of tumor suppressor genes such as Cdkn2b and Cdkn1b, thereby promoting MIZ1-mediated transcriptional activation of these genes. We found that MYC binds the STAT1 promoter in P493-6 human BL and mouse MYC-driven T-ALL (FIGS. 23e-f). This results is concordant with a previous study where MYC has been shown to transcriptionally repress STAT1. We evaluated changes in STAT1/2-Type I IFN signaling before and after MYC inactivation in MYC-driven lymphoma cell lines after overexpressing MYC or a MYC mutant that fails to sequester MIZ1 (MYC V394D), and the corresponding empty vector (EV) control. While MYC overexpression effectively repressed production of STAT1/2 (FIGS. 6f-h) and IFNα2 (FIG. 6i), MYCV394D mutant partially rescued the activation of STAT1/2-Type I IFN signaling in P493-6 cells. Our results are concordant with previous studies that report MYC transcriptionally represses STAT1, blocking Type I IFN production and activation. We now demonstrate that a part of this suppression occurs due to the sequestration of transactivators such as MIZ1.

In MYC-driven T-ALL cells, we observe that the mechanism of MYC-mediated suppression of Type I IFN signaling cascade is independent of MIZ1 (FIG. 28), suggesting possible involvement of other MYC binding partners such as SP1/3. We evaluated whether MYC-mediated repression of STAT1/2-Type I IFN signaling and hence, NK surveillance dependent on the cell autonomous effects of MYC on proliferation and apoptosis. To this end, we abrogated such cell autonomous effects of MYC by knocking down BIM1 and overexpressing BCLXL in MYC-driven T-lymphoma cells (FIG. 29). Both BIM1 knockdown and BCLXL overexpression are required to block apoptosis of tumor cells post MYC inactivation. Despite the blockade of the MYC-mediated cell autonomous apoptotic program after MYC inactivation, we observed an increased activation of STAT1 and STAT2 (FIG. 29), proving that MYC-mediated repression of STAT1/2-Type I IFN signaling is independent of its cell autonomous functions.

Figure 7A:
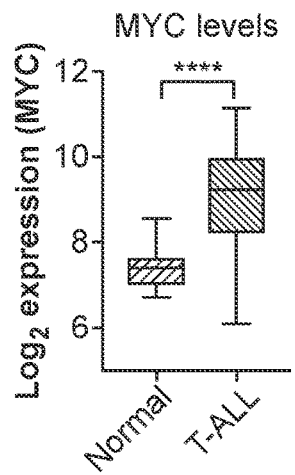
FIG. 7A-7L: Higher STAT1, STAT2 and NK cells predict favorable clinical outcome in MYCdriven human lymphomas.
Figures 7B, 7C, 7D, 7E:
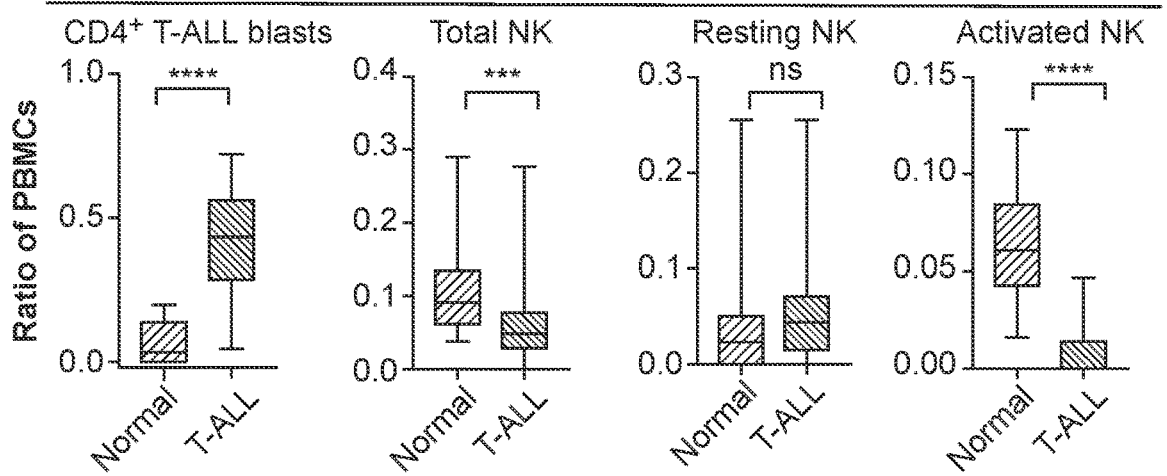
Figures 7F, 7G:
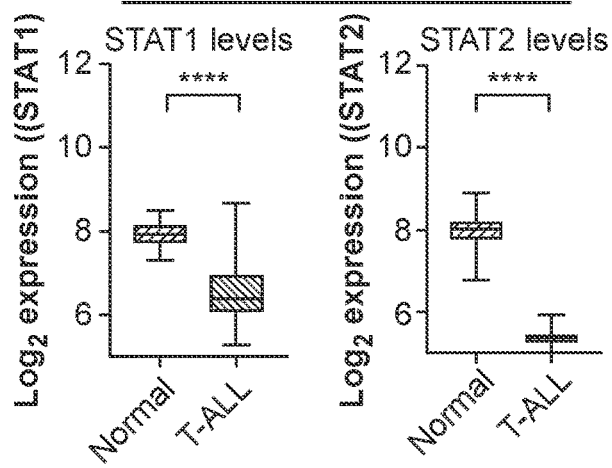
Figures 30A, 30B, 30C:
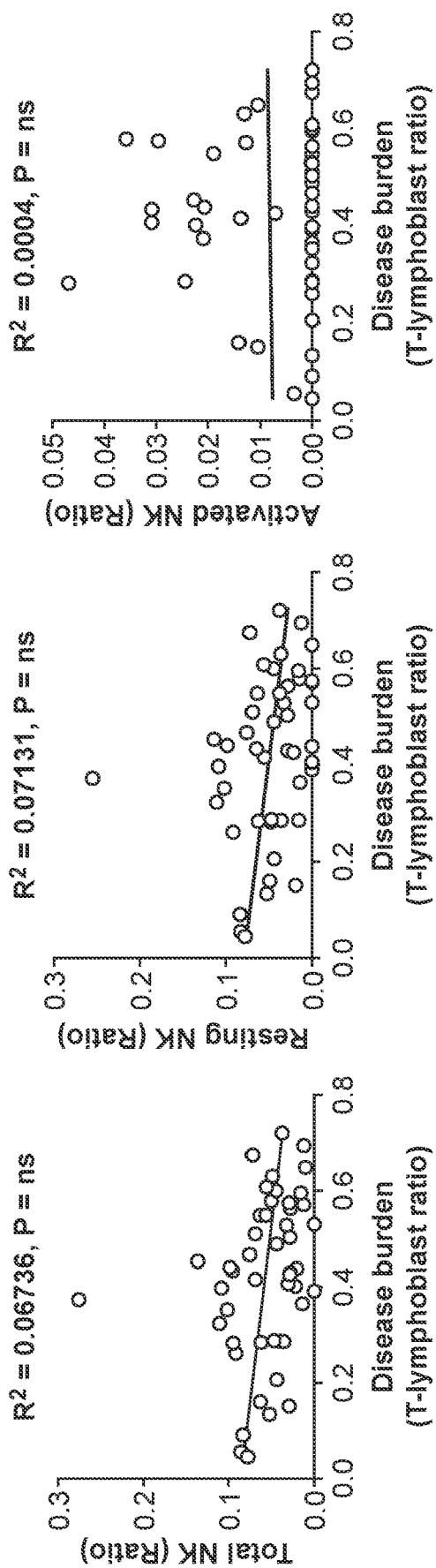
FIG. 30A-30C: Extent of disease burden in BL patients has no impact on NK profile.

MYC-Driven Human Lymphomas Block NK-Mediated Surveillance by Repressing STAT1/2. We examined MYC-driven human lymphoma samples for evidence of suppression of NK-mediated immune surveillance through repression of STAT1/2 signaling. Using CIBERSORT on bulk expression data from lymphoma patients, we compared the fractions of NK cells in mononuclear cells derived from blood of oncogene-addicted human T-lymphoma patients (n=48, GSE62156) and normal healthy individuals (n=20). Of note, MYC levels are significantly higher in T-lymphoma patients as compared to healthy individuals (FIG. 7a) because of the presence of chromosomal translocations that can potentially activate MYC. We observed a reduction of total and activated NK subsets in human T-ALL patients as compared to healthy individuals (FIGS. 7b-e). In accordance with our CIBERSORT results on bulk MYC-driven T-lymphoma, we observed a significant suppression of STAT1 and STAT2 levels in human T-lymphoma patients when compared to their normal counterparts (FIGS. 7f-g). We demonstrated that decrease in total and activated NK percentages in human T-lymphomas had no bearing on the extent of disease burden (blast percentages) in individual patients by showing the lack of correlation between disease burden and NK cell levels (FIG. 30). These findings corroborate that NK suppression occurs during both human and murine MYC-driven T cell lymphomagenesis.

Figure 7K:
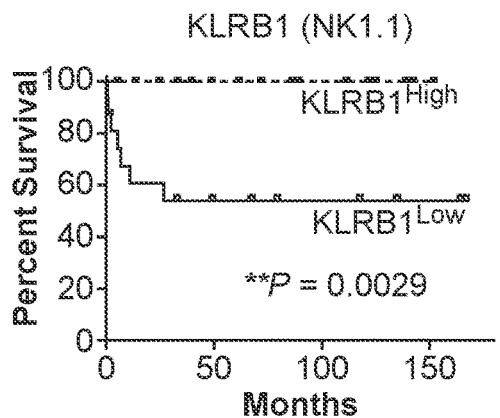
Figure 7L:
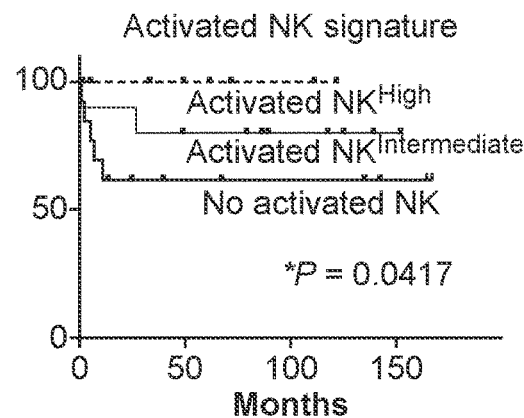
Figure 7H:
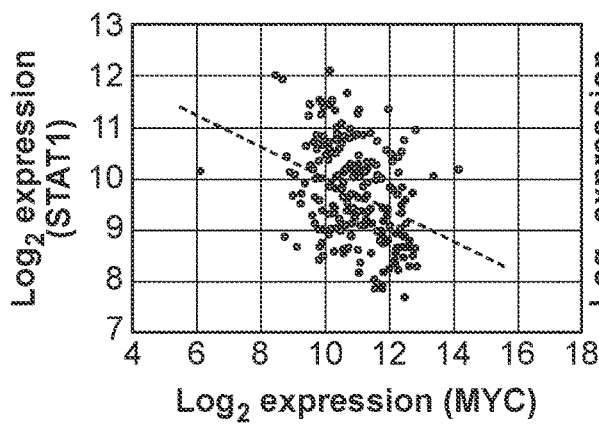
Figure 7I:
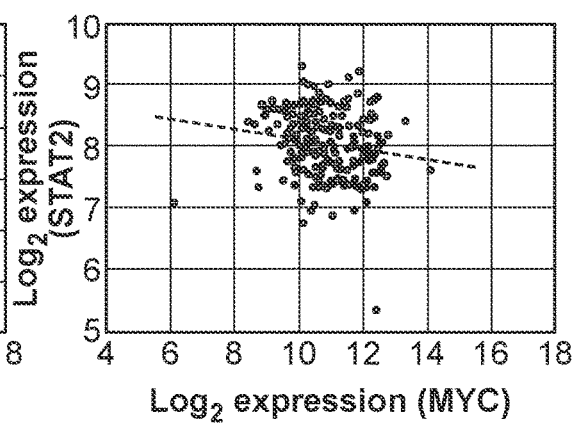

Next, we analyzed human lymphomas (BL and DLBCL) that are naturally driven by MYC. Of these, BL patients always carry a MYC translocation that leads to MYC hyperactivation. We observed that STAT1 and STAT2 levels inversely correlate with MYC levels in a panel of BL (n=34) and DLBCL (n=187) patients (FIGS. 7h-i). Of note, BL patients display the highest MYC levels in combination with lowest STAT1 and STAT2 levels (FIGS. 7h-i), thus proving that natural MYC addiction in this subgroup, leads to suppression of STAT1/2-Type I IFN signaling. We analyzed whether separation of BL patients into four groups based on their median expressions of both STAT1 and STAT2 conferred any survival advantage.

Figure 7J:
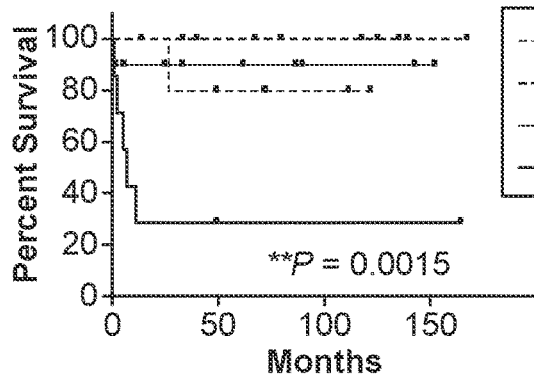
Figure 31:
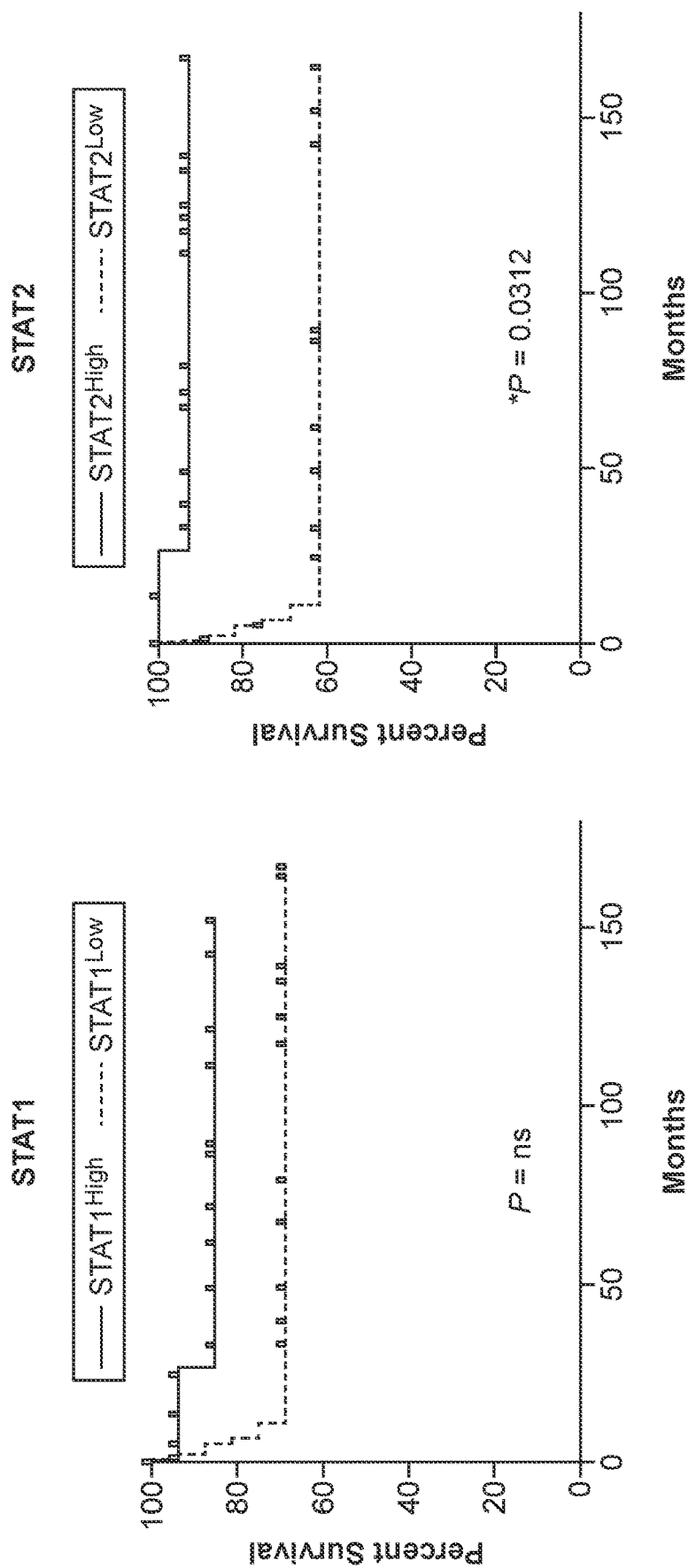
FIG. 31: Higher level of STAT1/2 signaling confers longer overall survival in BL patients. Comparison of overall survival probabilities of BL patients (n=34, GSE4475) separated based on expression of STAT1 and STAT2. P-values have been calculated using the log-rank test.

We observed that patients with lowest levels of both STAT1 and STAT2 had the most unfavorable clinical outcome (FIG. 7j, FIG. 31). Upon separating BL patients based on median expression of KLRB1 (NK1.1, FIG. 7k), and NK cell percentages (CIBERSORT, FIG. 7l), we observed that higher levels of NK cells conferred a favorable clinical outcome. Thus MYC overexpression enables human lymphomas to completely override NK-mediated immune surveillance by complete suppression of STAT1/2-Type I IFN signaling.

Figure 32A:
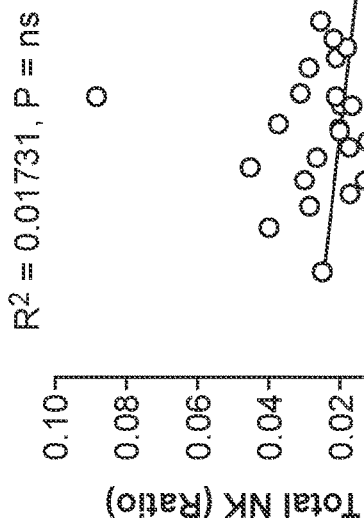
FIG. 32A-32D: Extent of disease burden in BL patients has no impact on NK profile.
Figure 32C:
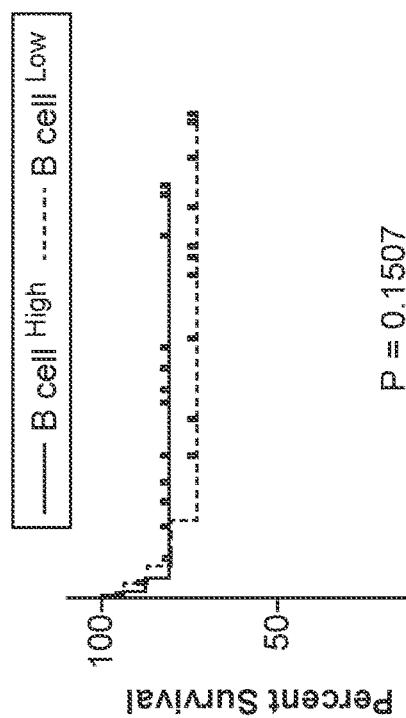
Figure 32B:
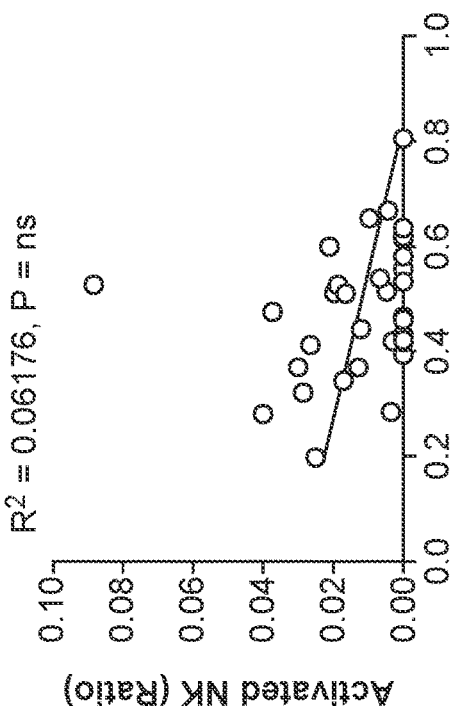
Figure 32D:
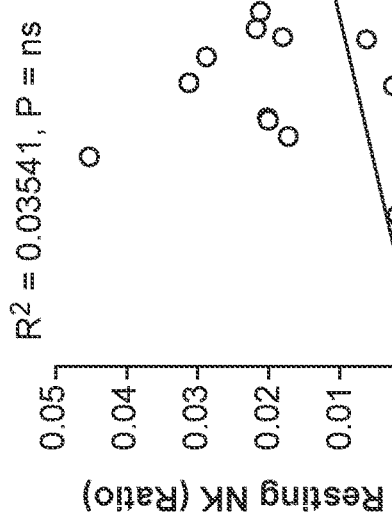

We observed no difference in survival of BL patients when separated based on disease burden (FIG. 32a), and, no correlation between disease burden (B-lymphoblast levels) and NK cell levels in BL (FIGS. 32b-d). Thus, NK suppression in human lymphomas does not passively occur due to replacement by malignant cells.

Mapping the immunobiology of each cancer is crucial to identifying potent immunotherapies for sustained cancer regression. Using CyTOF, we have for the first time mapped the immune signature of MYC-driven lymphomas. We identified a novel mechanism of coevolution of the immune system alongside the lymphoma, whereby MYC oncogene directly suppresses NK-mediated immune surveillance. We show that MYC hyperactivation during lymphomagenesis leads to systemic reduction in numbers of activated NK cells, while MYC inactivation partially reverses this effect. MYC did not globally suppress all immune subsets, so its repression of the NK compartment was specific.

We demonstrate that NK-mediated immune surveillance significantly delays overt MYC-driven lymphomagenesis, and sustains lymphoma regression post MYC inactivation. Our findings show that MYC-driven lymphomas are particularly sensitive to adoptive NK cell-based therapies when administered along with MYC inhibitors. In an animal model lymphomagenic MYC eventually suppressed NK cells that were therapeutically administered (FIGS. 3o-e).

Studies are underway to develop modes of therapy, and identify the timing and dosage of administration for therapeutic benefit. We show that MYC-driven lymphomas that arise in immune-competent hosts overcome NK-mediated immune surveillance by causally repressing the STAT1/2-Type I IFN cytokine axis that is required for NK homeostasis. MYC represses STAT1/2-Type I IFN signaling in part by sequestering transactivator MIZ1.

Aside from being anti-viral agents, Type I IFNs were used as cancer therapeutics because of their anti-proliferative effects on cancer cells. However, no studies thus far had explored two important aspects of Type I IFN therapy: (1) Is there a direct connection between driver oncogenes in cancer and Type I IFNs? (2) Are particular cancers sensitive to Type I IFN therapy because of induction of specific immune surveillance mechanisms? Our current study answers both these questions: First, we demonstrate that MYC directly abrogates the anti-cancer effects of Type I IFNs by transcriptionally suppressing STAT1 and STAT2. Second, rescue of NK cell infiltration into spleens of lymphoma-bearing mice upon Type I IFN treatment proves that MYC-mediated repression of STAT1/2-Type I IFN cascade causally blocks NK-mediated immune surveillance (Model, FIG. 33).

Specific NK receptor-ligand interactions that mediate the recognition of tumor cells by NK cells have been previously shown to block MYC-driven lymphomagenesis. Our analyses show a modest but significant differential upregulation of the NKG2D ligands (NKG2DL) on the surface of MYC-driven human P493-6 BL after MYC inactivation (FIG. 34). Of note, NKG2D ligands are expressed at very low levels in MYC-driven lymphoma cell lines in culture, which can be attributed to the lack of an immune microenvironment in vitro. Expression levels of NKG2D (KLRK1) that were reduced in vivo in our primary autochthonous model bearing overt lymphoma ($MYC^{ON}$), were restored to normal post MYC inactivation ($MYC^{OFF}$) (FIG. 50. Therefore, multiple mechanisms of MYC-mediated suppression of NK surveillance may be at play during lymphomagenesis. Interestingly, our findings suggest that an identical paradigm of MYC repressing the STAT1/2-Type I IFN pathway operates in human lymphomas naturally addicted to MYC, including BL and DLBCL.

Maturation of NK cells is arrested during MYC-driven lymphomagenesis. We investigated whether reduction in mature CD3− NKp46+ NK cells during MYC-induced lymphomagenesis occurs because of increased cell death. Surprisingly, we observed reduced death of NK cells at sites of lymphomagenesis in lymphoma-bearing MYCON mice, in comparison to normal and MYCOFF cohorts. Hence, suppression of NK subset during lymphomagenesis is not caused by increased apoptosis of NK cells induced by lymphomagenic MYC.

The disappearance of NK cells from the bone marrow of MYCON mice suggested that MYC-driven ymphomagenesis might abrogate the replenishment of mature CD3-NKp46+NK cells in the periphery possibly by blocking early NK cell development. We tested this possibility by comparing the absolute counts of NK cell precursors (NKP, CD122+ NKp46−, FIG. 35a), and the more differentiated CD122+ NKp46+ iNK (immature NK, FIG. 35b) cells in bone marrow from normal (n=8), SRα-tTA $MYC^{ON}$ (lymphoma, n=8), and SRα-tTA $MYC^{OFF}$ (regressed lymphoma, n=8) mice. While we observed no significant changes in the numbers of NKP across the three groups, the numbers of iNK cells were significantly reduced in MYCON bone marrow, in comparison to MYCOFF and normal bone marrows (FIGS. 35a-b). Consistent with these observations, the ratio of counts of NKP vs iNK were significantly enhanced in individual $MYC^{ON}$ mice in comparison to healthy and MYCOFF mice (FIG. 35c).

We infer that oncogenic MYC blocks the expression of NKp46 and hence, the transition from NKP to iNK stage of NK cell maturation in the bone marrow. The spleens of MYCON mice exhibited no changes in the CD122+ NKp46− NKP, and a significant reduction in the more differentiated CD122+ NKp46+ iNK fraction (FIGS. 35e-h), concordant with the changes observed in their corresponding bone marrows (FIGS. 35a-d). Hence, NK cells are systemically suppressed during MYC-induced lymphomagenesis because of arrested NK cell maturation in the bone marrow that translates to the periphery (FIG. 35i).

Our results suggest that other immune effectors may be critically altered during MYC-driven lymphomagenesis such as, neutrophils, B cells and DCs. Since many conventional therapies for lymphoid malignancies are significantly immune suppressive, it is essential to consider the role of the immune microenvironment in understanding and therapeutically exploiting oncogene addiction. Many investigators are currently exploring targeting MYC-driven cancers by direct inhibition. Cell-based immunological treatments such as NK cells can significantly improve the efficacy of agents that target MYC for the treatment of human cancer, particularly MYC-associated hematopoietic malignancies.

Materials and Methods

Cell Lines and Cell Culture.

Conditional MYC-driven mouse T-ALL cell lines were derived from Eµ-tTA/tet-O-MYC mice. T-ALL status of the derived cell line was measured by flow cytometry (FIG. 18). c-MYC was inhibited in Eµ-tTA/tet-O-MYC T-ALL cells by treating cell cultures with 0.02 µg/ml doxycycline (Sigma-Aldrich, T7660) for 4, 8, 24 and 48 h. BL-like human P493-6 cells were kindly provided by Chi Van Dang, University of Pennsylvania. For c-MYC inactivation in P493-6 cells, the conditional pmyc-tet construct was repressed with 0.1 µg/ml doxycycline (Sigma-Aldrich, T7660) for 24 h. Cell lines were confirmed to be negative for *mycoplasma* contamination and maintained in Roswell Park Memorial Institute 1640 medium (RPMI, Invitrogen) with GlutaMAX containing 10% fetal bovine serum, 100 IU/ml penicillin, 100 µg/ml streptomycin, 50 mM 2-mercaptoethanol at 37° C. in a humidified incubator with 5% $CO_2$.

Isolation and Processing of Immune Cells from Mice.

We used young male mice (around 8-12 weeks of age). The following strains of mice were used: Eµ-tTA/tet-O-MYC mice and the corresponding FVB/N wildtype strain. The Eµ-tTA/tet-OMYC males developed T-ALL at approximately two months of age. Diseased mice were identified based on the presence of visible symptoms of T-ALL development; namely, loss of weight and appetite, ruffled fur, shortness of breath and movement difficulties. Half the number of male littermates that developed T-ALL were subjected to doxycycline treatment to inactivate MYC. For T-ALL mice subject to MYC inactivation, one starter dose of doxycycline was given intraperitoneally, after which, the mice continuously received doxycycline for four days in their drinking water. Leukemic littermates from each cage were randomly and equally divided between MYCON/HIGH (untreated) or MYCOFF/LOW (doxycycline treated) groups. Spleens, blood and bone marrow were isolated from the three mice groups, namely, Eµ-tTA/tet-O-MYC ($MYC^{ON/HIGH}$), Eµ-tTA/tet-O-MYC+Doxycycline ($MYC^{OFF/LOW}$), and FVB/N controls. Blood was drawn by cardiac puncture after euthanizing the mice, and directly subjected to erythrocyte lysis. Bone marrow was obtained by flushing the cavities of femur and tibia with PBS. Spleen and bone marrow were homogenized using a 191/2G needle and filtered through a 70 µm filter. After depletion of erythrocytes from spleen, blood and bone marrow using RBC lysis buffer (BD PharmLyse, BD Biosciences), washed cells were cryopreserved and utilized for CyTOF or flow cytometry. No blinding was done while executing the animal experiments. All mouse experiments were approved by the Administrative Panel on Laboratory Animal Care (APLAC) at Stanford University, and were carried out in accordance with institutional and national guidelines.

Mass Cytometry (CyTOF Immunophenotyping).

This assay was performed in the Human Immune Monitoring Center at Stanford University. Mouse splenocytes were thawed in warm media, washed twice, resuspended in CyFACS buffer (PBS supplemented with 2% BSA, 2 mM EDTA, and 0.1% soium azide), and viable cells were then counted by Vicell. Cells were added to a V-bottom microtiter plate at 1 million viable cells/well and washed once by pelleting and resuspension in fresh CyFACS buffer. The cells were stained for 60 min on ice with 50 uL of the following antibody-polymer conjugate cocktail (Table 3). All antibodies were custom-ordered metal-conjugates from Fluidigm (Table 3). The cells were washed twice; by pelleting and resuspension with 500 µL FACS buffer. The cells were resuspended in 100 uL PBS buffer containing 1.7 µg/mL Live-Dead (DOTA-maleimide (Macrocyclics) containing natural-abundance indium). The cells were washed twice by pelleting and resuspension with 500 uL CyFACS buffer. The cells were resuspended in 100 uL 2% PFA in PBS and placed at 4° C. overnight. The next day, the cells were pelleted and washed by resuspension in fresh PBS. The cells were resuspended in 100 µL eBiosciences permeabilization buffer (1× in PBS) and placed on ice for 45 min before washing twice with 500 µL CyFACS buffer. The cells were resuspended in 100 µL iridium-containing DNA intercalator (1:2000 dilution in PBS; DVS Sciences) and incubated at room temperature for 20 min. The cells were washed once in CyFACS buffer, then three times in 500 uL MilliQ water. The cells were diluted to a concentration of ~800,000 cells/mL in MilliQ water containing 0.1×EQ normalization beads (Fluidigm) before injection into the CyTOF (Fluidigm).

Data analysis was performed using FlowJo v10 by gating on intact cells based on the Iridium vs Ce140 (bead), then both Iridium isotopes from the intercalator, then on singlets by Ir191 vs cell length, then on live cells (Indium-LiveDead minus population), followed by cell subset-specific gating. The data was analyzed using FlowJo X 10.0.7r2 and viSNE (Cytobank Inc.).

Phospho-CyTOF.

The harvested cells were suspended in 16% PFA and incubated for 10 minutes at room temperature. After washing with CyFACS buffer (1× CyPBS with 0.1% BSA, and 0.05% Na Azide; made in Milli-Q water), surface staining was performed by incubating the cells with the surface-staining antibody cocktail (Table 4) at room temperature for 30 minutes. The cells were then washed with CyFACS buffer and permeabilized before carrying out intracellular staining. The cells were then incubated with the intracellular antibody cocktail (FIG. 9) at room temperature for 30 minutes. After washing with CyPBS, the cells were incubated with Ir-intercalator solution on ice for 20 minutes. The samples were then washed with Milli-Q water and acquired on the CyTOF instrument using standard instrument set up procedures. The data was analyzed using FlowJo X 10.0.7r2.

Flow cytometry. All antibodies for flow cytometry measurements as well as their respective isotype controls are indicated in Table 5. Surface staining antibodies that were PE conjugated were used at a dilution of 1:10 and the ones conjugated with FITC at a dilution of 1:5. Multicolor flow cytometry staining was performed according to standard procedures. Cells were stained with Propidium Iodide (PI, Sigma-Aldrich) to gate out dead cells. Labeled cells were analyzed on a FACSCalibur (Becton Dickinson). The data was analyzed using FlowJo X 10.0.7r2.

Calculation of Absolute Immune Cell/Counts.

Viable cells were counted using a Vicell before subjecting the single cell suspensions of spleen, blood and bone marrow to CyTOF or flow cytometry, respectively. Using the percentages of the immune populations calculated by CyTOF and flow cytometry on the same day, absolute viable cell numbers of the different immune subsets were computed.

RNA Sequencing.

A part of the splenic single cell suspensions from normal (FVB/N, n=3), Eµ-tTA MYCON (n=4) and Eµ-tTA MYCOFF (n=3) mice subjected to CyTOF were used to generate RNA. RNA sequencing was performed at the Beijing Genomics Institute (BGI) using their platform. RNA sequencing data are deposited in Gene Expression Omnibus (GEO).

CIBERSORT.

Human CIBERSORT was carried out at Stanford using LM22 reference matrix of gene expression in human immune subsets. For CIBERSORT of splenic immune compositions in normal (FVB/N), Eµ-tTA MYCON and Eµ-tTA MYCOFF mice, a reference matrix was generated using ImmGen. CIBERSORT was carried out on CyTOF-matched normal (n=3), Eµ-tTA MYC$^{ON}$ (n=4) and Eµ-tTA MYC$^{OFF}$ (n=4) samples.

Transplantation of MYC-Addicted T-ALL and Bioluminescence Imaging.

A MYC-addicted T-ALL cell line derived from a male Eµ-tTA/tet-O-MYC mouse (FIG. 18) was labeled with luciferase. $3 \times 10^6$ luciferase-labeled T-ALL cells were then injected intravenously into two groups of immune-deficient hosts: NOD SCID (The Jackson Laboratory) and NOD-SCIDIL-2R$\gamma^{-/-}$ (NSG). Male transplant recipients used were between 4-5 weeks of age. Leukemic engraftment and progression were tracked by bioluminescence imaging (BLI) of the transplant recipients using an in vivo IVIS 100 bioluminescence/optical imaging system (Xenogen). D-Luciferin (Promega) dissolved in PBS was injected intraperitoneally at a dose of 2.5 mg per mouse 15 min before measuring the luminescence signal. General anesthesia was induced with 3% isoflurane and continued during the procedure with 2% isoflurane introduced through a nose cone. No blinding was done while executing the animal experiments. All mouse experiments were approved by the Administrative Panel on Laboratory Animal Care (APLAC) at Stanford University, and were carried out in accordance with institutional and national guidelines.

Adoptive Transfer of NK Cells into T-ALL-Bearing Recipient Mice.

$3 \times 10^6$ luciferase-labeled T-ALL cells were injected intravenously into 4-8 week old NSG mice (n=19). Post verification of T-ALL engraftment by BLI, all mice were treated with doxycycline to inactivate MYC. 10 of the 19 mice were subjected to adoptive transfer of NK cells isolated from spleens of 4-8 week old FVB/N mice by magnetic activated cell sorting (MACS, NK Cell Isolation Kit II, Miltenyi Biotech). Flow cytometry was performed to confirm the purity of the isolated NK cells. $1 \times 10^6$ MACS purified NK cells were injected per mouse into NSG transplant recipients bearing regressed T-ALL (on doxycycline, MYC$^{OFF}$).

NK Cell Depletion in Primary Eµ-tTA/Tet-O-MYC Mice.

To study the role of NK cell depletion on MYC-driven lymphomagenesis, 4-week-old male Eµ-tTA/tet-O-MYC mice (n=24) were treated intravenously every 10 days with either 100 µg of anti-NK1.1 (n=12) or control IgG2a (n=12) antibodies (PK136, BioXCell). Time to overt lymphomagenesis was compared between the two groups. Spleens were isolated from moribund mice in each group. Splenic suspensions were subjected to flow cytometry to verify T cell lymphoma as the cause of death.

Type I IFN Treatment of Primary Eµ-tTA/tet-O-MYC Mice.

20,000U of Type I IFN((R&D systems) was administered to Eµ-tTA/tet-O-MYC mice bearing overt lymphoma for 3 days. On day 3, spleens from treated mice were collected, and subjected to flow cytometry for NK and T cells. PBS-treated mice were used as controls. Absolute cell counts were obtained as described previously.

Immunoblotting.

Cells were lysed in CelLytic buffer (Sigma) supplemented with 1% protease inhibitor 'cocktail' (Pierce). Protein samples were subsequently separated by electrophoresis through NuPAGE (Invitrogen) 4-12% Bis-Tris gradient gels and were transferred to PVDF membranes (Immobilon; Millipore). For the detection of mouse and human proteins by immunoblot analysis, we used primary antibodies together with the WesternBreeze immunodetection system (Invitrogen). All antibodies used for immunoblotting and their corresponding dilutions are given in Table 6.

Quantitative RT-PCR.

Quantitative real-time PCR carried out with the SYBR-GreenER mix from Invitrogen according to standard PCR conditions and an ABI7900HT real-time PCR system (Applied Biosystems). Primers for quantitative RT-PCR are in Table 7.

Retrovirus Production and Transduction

Transfection of retroviral constructs was performed using Lipofectamine 2000 (Invitrogen) with Opti-MEM media (Invitrogen). Retroviral supernatants for infection of cells were generated after co-transfection of Phoenix cells containing the plasmids pHIT60 (gag-pol) and pHIT123 (ecotropic envelope) (provided by G.P. Nolan), with the retroviral constructs. Cells were cultured in high-glucose DMEM (Invitrogen) with GlutaMAX containing 10% FBS, 100 IU/ml penicillin, 100 µg/ml streptomycin, 25 mM HEPES, pH 7.2, 1 mM sodium pyruvate and 0.1 mM nonessential amino acids. Serum-free medium was replaced after 16 h with growth medium containing 10 mM sodium butyrate. After 8 h of incubation, the medium was changed back to growth medium without sodium butyrate. 24 h later, we harvested the viral supernatants, passed them through a 0.45-µm filter, and centrifuged them twice at 2,000 g for 90 min at 32° C. on 50 µg/ml RetroNectin-coated non-tissue-culture-treated six-well plates. Pre-B cells ($2 \times 10^6$ to $3 \times 10^8$ cells per well) were transduced by centrifugation at 600 g for 30 min and were maintained overnight at 37° C. with 5% $CO_2$ before transfer into culture flasks.

Lentivirus Production and Transduction

Lentiviral transfections were performed using Lipofectamine 2000 (Invitrogen) with Opti-MEM media (Invitrogen). We produced lentiviral supernatants to infect murine cells by cotransfecting HEK 293FT cells with the plasmids psPAX2 (gag-pol; Didier Trono, Addgene 12260) and pMD2.G (VSV-G envelope; Didier Trono, Addgene 12259). Cells were cultivated in high-glucose DMEM (Invitrogen) with GlutaMAX as described above. Culture supernatants were concentrated with Lenti-X™ Concentrator (Clontech) according to the manufactures recommendation. The concentrated viruses were incubated with the cells for 50 µg/ml RetroNectin-coated non-tissue culture treated 6-well plates. Immunohistochemistry Spleens and thymuses obtained from experimental mice were immersed in 20 ml of formalin (VWR) for 24 h and transferred to PBS. Paraffin embedding was carried out using standard procedures on a Tissue-TEK VIP processor (Miles Scientific), and 4 µm sections were mounted on Apex superior adhesive slides (Leica Microsystems) and stained on a Ventana BenchMark automated IHC stainer). Immunohistochemistry sections were mounted with mounting medium, antifade reagent (Pro-Long Gold; Invitrogen) was applied, and coverslips were sealed before acquisition of images at 25° C. on a Zeiss Axiovert 200M inverted confocal microscope with a 40 Plan Neofluor objective using IP Lab 4.0 software (Scanalytics).

ChIP-sequencing analysis. Raw files of ChIP-sequencing of Eµ-tTA/tet-O-MYC T-ALL cells (GSE44672) were downloaded from Gene Expression Omnibus (GEO). The FASTQ Groomer in Galaxy Software was used to generate files that were mapped to RefSeq database for mouse genes (mm9). The resulting bigWig files processed from Galaxy were visualized in Integrated Genome Viewer (IGV_2.3.72).

Statistical analysis. CyTOF, flow cytometry and CIBERSORT results are shown as box plots and comparisons between any two groups were made using the Mann-Whitney U test (not assuming normal distributions) with Graphpad Prism software. All remaining data are presented as mean±s.d. The comparisons for the mean values between two sample groups were made using the twotailed Student's t-test after calculating variances for each group with Graphpad Prism software. For experiments involving transplantation of cells into mice, the minimal number of mice in each group was calculated through the use of the 'cpower' function in the R/Hmisc package (R Development Core Team 2009; http://www.r-project.org). The Kaplan-Meier method was used for estimation of overall survival and relapse-free survival. For all survival analyses, the log-rank test was used to compare groups of transplanted mice or human patients. The R package 'survival' version 2.35-8 was used for the survival analysis. All p-values are two-tailed. The level of significance was set at $P<0.05$. P-values: ns=non-significant; *$p<0.05$; $p<0.01$; *$p<0.001$; ****$p<0.0001$.

TABLE 1

Antibodies used for CyTOF immunophenotyping (mouse)

| Antigen | Metal Tag | Source |
|---|---|---|
| Live-Dead | In115 | HIMC, Stanford University |
| Ly6G | Pr141 | Fluidigm Corporation |
| CD11c | Nd142 | Fluidigm Corporation |
| CD11b | Nd143 | Fluidigm Corporation |
| CD115 | Nd144 | Fluidigm Corporation |
| CD4 | Nd145 | Fluidigm Corporation |
| F4/80 | Nd146 | Fluidigm Corporation |
| CD45.2 | Sm147 | Fluidigm Corporation |
| CD19 | Sm149 | Fluidigm Corporation |
| CD25 | Nd150 | Fluidigm Corporation |
| IgM | Eu151 | Fluidigm Corporation |
| CD3 | Sm152 | Fluidigm Corporation |
| NKp46 | Eu153 | Fluidigm Corporation |
| Ter119 | Sm154 | Fluidigm Corporation |
| TCRγδ | Tb159 | Fluidigm Corporation |
| CD5 | Gd160 | Fluidigm Corporation |
| Ly6C | Dy162 | Fluidigm Corporation |
| CCR7 | Dy164 | Fluidigm Corporation |
| cKit | Er166 | Fluidigm Corporation |
| CD150 | Er167 | Fluidigm Corporation |
| CD8a | Er168 | Fluidigm Corporation |
| TCRβ | Tm169 | Fluidigm Corporation |
| CD49b | Er170 | Fluidigm Corporation |
| MHCII | Yb174 | Fluidigm Corporation |
| FCεRa | Yb175 | Fluidigm Corporation |

TABLE 2

Antibodies used for Phospho-CyTOF (human)

| Antigen | Metal Tag |
|---|---|
| Live-Dead | In115 |
| Ly6G | Pr141 |
| CD19 | Nd142 |
| CD117 | Nd143 |
| CD11b | Nd144 |
| CD4 | Nd145 |
| CD20 | Sm147 |
| CD7/CD45RO | Sm149 |
| CD123 | Eu151 |
| CD27 | Sm152 |
| CD45RA | Eu153 |
| CD45 | Sm154 |
| pP38 | Gd156 |
| CD24 | Gd157 |
| pSTAT3 | Gd158 |
| CD11c | Tb159 |
| CD14 | Gd160 |
| IgD | Dy161 |
| pERK1/2 | Dy162 |
| IκBtot | Dy163 |
| CD25 | Dy164 |
| pS6 | Ho165 |
| CD16 | Er166 |
| CD38 | Er167 |
| CD8 | Er168 |
| pSTAT1 | Tm169 |
| CD3 | Er170 |
| pSTAT5 | Yb172 |
| pPLCγ2 | Yb173 |
| HLADR | Yb174 |
| CD56 | Lu175 |
| Cd127 | Yb176 |

TABLE 3

Antibodies used for flow cytometry

| Surface Antigen | Clone ID/ Catalog No. | Reactivity | Source |
|---|---|---|---|
| CD3e | 145-2C11 | Mouse | BD Pharmingen |
| CD4 | RM4-5 | Mouse | BD Pharmingen |
| CD8a | 53-6.7 | Mouse | BD Pharmingen |
| CD49b | DX5 | Mouse | eBioscience |
| CD335 (NKp46) | 29A1.4 | Mouse | BioLegend |
| Nk1.1 | PK136 | Mouse | BD Pharmingen |
| CD16/CD32 (Fc block) | 2.4G2 | Mouse | BD Pharmingen |
| CD20 | 2H7 | Human | BioLegend |
| Human Fc block | 564219 | Human | BD Pharmingen |

TABLE 4

Antibodies used for immunoblotting

| Antigen | Clone ID | Dilution | Source |
|---|---|---|---|
| MYC | N-262 | 1:1000 | Santa Cruz Biotechnology |
| ACTB | ab8227 | 1:10,000 | Abcam |
| ERK1/2 | 9102 | 1:1000 | Cell Signaling Technology |
| Phospho T202/Y204 ERK1/2 | 9101 | 1:1000 | Cell Signaling Technology |
| STAT1 | 9172 | 1:1000 | Cell Signaling Technology |
| Phospho S727 STAT1 | 9177 | 1:1000 | Cell Signaling Technology |
| STAT2 | D9J7L | 1:1000 | Cell Signaling Technology |

TABLE 5

Lentiviral and retroviral vectors used in the study

| Vector | Type |
|---|---|
| pMSCV Luciferase IRES-puro | Retroviral |
| pRRL | Lentiviral |
| pRRL hMYC | Lentiviral |
| pRRL hMYC V394D | Lentiviral |

TABLE 6

Sequences of oligonucleotide primers used for quantitative PCR

Mouse primers

| | |
|---|---|
| mVEGFA_F | 5'-GTAACGATGAAGCCCTGGAG-3' |
| mVEGFA_R | 5'-AAATGCTTTCTCCGCTCTGA-3' |
| mVEGFB_F | 5'-CAGCCAATGTGAATGCAGAC-3' |
| mVEGFB_R | 5'-GGAGTGGGATGGATGATGTC-3' |
| mIFNB1_F | 5'-GCTCCAAGAAAGGACGAACA-3' |
| mIFNB1_R | 5'-CCCAGTGCTGGAGAAATTGT-3' |
| mIFNA2_F | 5'-AAGGTCCTGGCACAGATGAG-3' |
| mIFNA2_R | 5'-GGAGGGTTGTATTCCAAGCA-3' |
| mSTAT1_F | 5'-TGGTGAAATTGCAAGAGCTG-3' |
| mSTAT1_R | 5'-CAGACTTCCGTTGGTGGATT-3' |
| mSTAT2_F | 5'-GCCTCCATTCTCTGGTTCAA-3' |
| mSTAT2_R | 5'-TCCTCCATCTTGCAGCTCTT-3' |
| mMYC_F | 5'-TCTCCATCCTATGTTGCGGTC-3' |
| mMYC_R | 5'-TCCAAGTAACTCGGTCATCATCT-3' |
| mUBC_F | 5'-AGCCCAGTGTTACCACCAAG-3' |
| mUBC_R | 5'-ACCCAAGAACAAGCACAAGG-3' |

Human primers

| | |
|---|---|
| hMS4A1_F | 5'-GGGGCTGTCCAGATTATGAA-3' |
| hMS4A1_R | 5'-CCAGGAGTGATCCGGAAATA-3' |
| hIFNB1_F | 5'-GCCTCAAGGACAGGATGAAC-3' |
| hIFNB1_R | 5'-TCTCATTCCAGCCAGTGCTA-3' |
| hIFNA1_F | 5'-CTCTCTGGGCTGTGATCTCC-3' |
| hIFNA1_R | 5'-ACTGGTTGCCATCAAACTCC-3' |
| hIFNA2_F | 5'-GCAAGTCAAGCTGCTCTGTG-3' |
| hIFNA2_R | 5'-CAAACTCCTCCTGGGGAAAT-3' |
| hVEGFA_F | 5'-AAGGAGGAGGGCAGAATCAT-3' |
| hVEGFA_R | 5'-CACACAGGATGGCTTGAAGA-3' |
| hVEGFB_F | 5'-AACACAGCCAGTGTGAATGC-3' |
| hVEGFB_R | 5'-AGTGGGATGGGTGATGTCAG-3' |
| hSTAT1_F | 5'-CCGTTTTCATGACCTCCTGT-3' |
| hSTAT1_R | 5'-TGAATATTCCCCGACTGAGC-3' |

TABLE 6-continued

Sequences of oligonucleotide primers used for quantitative PCR

| | |
|---|---|
| hSTAT2_F | 5'-GGAACAGCTGGAGACATGGT-3' |
| hSTAT2_R | 5'-GGCTGGGITTCTACCACAAA-3' |
| hMYC_F | 5'-CTGCGACGAGGAGGAGAACT-3' |

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

For further elaboration of general techniques useful in the practice of this invention, the practitioner can refer to standard textbooks and reviews in cell biology, tissue culture, and embryology. With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998).

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and Clon-Tech.

What is claimed is:

1. A method for treating a patient having a cancer suspected of being associated with MYC activation, the method comprising:
   determining the MYC status of the cancer, and in a cancer that is determined to be driven by MYC activation, administering a composition of an effective dose of one or both of activated NK cells and a type 1 interferon, wherein determining the MYC status comprises:
   obtaining a patient sample comprising hematopoietic cells,
   determining the proportion of mature and activated NK cells among lymphocytes;
   wherein decreased levels of mature and activated NK cells relative to a counterpart normal sample is indicative of MYC association.

2. The method of claim 1, wherein the activated NK cells are positive for expression of NKp46.

3. The method of claim 1, wherein the activated NK cells are administered in combination with the type 1 interferon.

4. The method of claim 1, wherein the type 1 interferon is human interferon alpha (IFNα).

5. The method of claim 1, wherein the administered NK cells are autologous.

6. The method of claim 1, wherein the administered NK cells are allogeneic.

7. The method of claim 1, wherein the NK cells are activated with cytokines in vitro prior to administration.

8. The method of claim 1, where the cancer is a hematologic cancer.

9. The method of claim 8, wherein the cancer is a non-Hodgkins lymphoma (NHL).

10. The method of claim 9, where the cancer is Burkitt's lymphoma.

11. The method of claim 9, wherein the cancer is diffuse large B cell lymphoma.

12. The method of claim 9, where the cancer of T cell acute lymphocytic leukemia.

* * * * *

UNITED STATES PATENT AND TRADEMARK OFFICE
CERTIFICATE OF CORRECTION

| | | |
|---|---|---|
| PATENT NO. | : 11,648,275 B2 | Page 1 of 1 |
| APPLICATION NO. | : 16/771617 | |
| DATED | : May 16, 2023 | |
| INVENTOR(S) | : Srividya Swaminathan et al. | |

It is certified that error appears in the above-identified patent and that said Letters Patent is hereby corrected as shown below:

In the Specification

In Column 1, immediately after Line 12, please insert the STATEMENT OF GOVERNMENT SUPPORT section with the following:
-- GOVERNMENT SUPPORT RESEARCH
This invention was made with Government support under contracts CA170378 and CA188383 awarded by the National Institutes of Health. The Government has certain rights in the invention. --

Signed and Sealed this
Sixth Day of January, 2026

John A. Squires
*Director of the United States Patent and Trademark Office*